US010335481B2

(12) United States Patent
Kai et al.

(10) Patent No.: US 10,335,481 B2
(45) Date of Patent: Jul. 2, 2019

(54) GENE-MODIFIED MEASLES VIRUS FOR TUMOR TREATMENT USE

(71) Applicant: THE UNIVERSITY OF TOKYO, Tokyo (JP)

(72) Inventors: Chieko Kai, Tokyo (JP); Misako Yoneda, Tokyo (JP)

(73) Assignee: THE UNIVERSITY OF TOKYO, Tokyo (JP)

( * ) Notice: Subject to any disclaimer, the term of this patent is extended or adjusted under 35 U.S.C. 154(b) by 0 days.

(21) Appl. No.: 15/512,242

(22) PCT Filed: Sep. 19, 2015

(86) PCT No.: PCT/JP2015/076817
§ 371 (c)(1),
(2) Date: Jul. 14, 2017

(87) PCT Pub. No.: WO2016/047645
PCT Pub. Date: Mar. 31, 2016

(65) Prior Publication Data
US 2017/0340726 A1    Nov. 30, 2017

(30) Foreign Application Priority Data

Sep. 22, 2014 (JP) ................................. 2014-193156

(51) Int. Cl.
| | |
|---|---|
| *A61K 39/165* | (2006.01) |
| *C12N 7/00* | (2006.01) |
| *A61K 39/00* | (2006.01) |
| *C12N 15/09* | (2006.01) |
| *A61K 35/768* | (2015.01) |

(52) U.S. Cl.
CPC .......... *A61K 39/165* (2013.01); *A61K 35/768* (2013.01); *C12N 7/00* (2013.01); *C12N 15/09* (2013.01); *A61K 2039/5254* (2013.01); *A61K 2039/54* (2013.01); *A61K 2039/552* (2013.01); *A61K 2039/572* (2013.01); *A61K 2039/585* (2013.01); *C12N 2760/18421* (2013.01); *C12N 2760/18422* (2013.01); *C12N 2760/18433* (2013.01); *C12N 2760/18434* (2013.01); *C12N 2760/18471* (2013.01)

(58) Field of Classification Search
None
See application file for complete search history.

(56) References Cited

U.S. PATENT DOCUMENTS

2013/0295114 A1    11/2013  Richardson
2017/0340726 A1*  11/2017  Kai ...................... A61K 39/165

FOREIGN PATENT DOCUMENTS

JP        2013-216609 A     10/2013

OTHER PUBLICATIONS

Vongpunsawad et al. (Journal of Virology. Jan. 2004; 78 (1): 302-313).Sugiyama.*
Haralambieva et al. (Molecular Therapy. 2007; 15 (3): 588-597).*
Sugiyama et al., "Kumikae Mashin Virus o Mochiita Nyugan Chiryoho Kaihatsu no Kisoteki Kenkyu" (Basic studies regarding development of therapeutic method for breast cancer using recombinant measles virus), Dai 58, The Japanese Society of Virology, Gakujutsu Shukai Program Shoroku-shu, 2010, P2-019. Cited in ISR. With partial Translation. (2 pages).
Kai et al., "Gan Chiryo-yo Kumikae Mashin Virus no Kaihatsu", Gan Chiryo-yo Kumikae Mashin Virus no Kaihatsu ni Kansuru Kenkyu (Development of recombinant measles virus for treatment of cancer), Heisei 25 Nendo Sokatsu, Buntan Kenkyu Hokokusho, May 2014. Cited in ISR. With partial Translation. (11 pages).
Delpeut et al., "The Tumor-Associated Marker", PVRL4 (Nectin-4), is the Epithelial Receptor for Morbilliviruses, Viruses, (2014) 6, vol. 6, pp. 2268-2286, Cited in ISR. (19 pages).
Tahara et al., "Rensai Virus no Konnichiteki Imi 5-Kiso Virus-gaku no Kanten kara (3)—Virus no Reverse Genetics", Antibiotics & Chemotherapy, (2010) vol. 26, No. 7. Cited in ISR. With partial Translation. (9 pages).
Inoue et al., "Haigan Kansaibo o Hyoteki to shita Shinki Idenshi Kaihen Mashin Shuyo Yokaisei Virus Ryoho", Annals of The Japanese Respiratory Society, Mar. 10, 2013, p. 266, PP685. Cited in ISR. With partial Translation. (2 pages).
Shoji et al., "Inu Nyugan ni Taisuru Kumikae Mashin Virus o Mochiita Shinki Chiryoho no Kaihatsu", Dai 157 Kai Japanese Society of Veterinary Science Gakujutsu Shukai Koen Yoshishu, Aug. 11, 2014, p. 482, HSO-21. Cited in ISR. With English Translation. (3 pages).
Fujiyuki et al., "Kumikae Mashin Virus no Haigan Saibokabu ni Taisuru Koshuyo Koka", Dai 62 Kai, The Japanese Society of Virololgy Gakujutsu Shukai Program Shoroku-shu, Oct. 31, 2014, p. 143, O1-01-03. Cited in ISR. With English Translation. (3 pages).
Shoji et al., "Shuyo Yokaisei Kumikae Mashin Virus no Inu Nyugan Saibo ni Taisuru Yukosei", Dai 62 Kai,The Japanese Society of Virology Gakujutsu Shukai Program Shoroku-shu, Oct. 31, 2014, p. 144, O1-1-05. Cited in ISR. With English Translation. (3 pages).
Fujiyuki et al., "A measles virus blind to signaling lymphocytic activation molecule is an oncolytic agent for lung cancer treatment", Presentation, The Institute of Medical Science, The University of Tokyo, Japan. Published Jul. 25, 2014, presentation Jul. 28, 2014. (15 pages).
Fujiyuki et al., "Oncolytic effect of measles virus blind to signaling lymphocytic activation molecule is an oncolytic agent for lung cancer treatment," Japanese Cancer Association, Tumor Immunology (1), Abstract J-3363, Sep. 10, 2014. (2 pages).

(Continued)

Primary Examiner — Shanon A. Foley
(74) Attorney, Agent, or Firm — Westerman, Hattori, Daniels & Adrian, LLP

(57) ABSTRACT

It is an object of the present invention to provide a medicament or a pharmaceutical composition, which is effective for the treatment of various cancers.
More specifically, the present invention relates to a pharmaceutical composition for use in the treatment of cancers, which comprises rMV-SLAM-blind or rMV-V(−)-SLAM-blind. The pharmaceutical composition has the effect of causing the regression of tumor, even if it is intravenously administered, and it also exhibits effects on cancer metastasized from a primary lesion.

14 Claims, 16 Drawing Sheets

Specification includes a Sequence Listing.

(56) References Cited

OTHER PUBLICATIONS

Shoji et al., "Development of Novel Therapy of Using Recombinant Measles Virus to Dog Breast Cancer", Presentation, Japanese Society of Veterinary Science, Sep. 10, 2014, with English Translation. (21 pages).
Grote et al., "Live attenuated measles virus induces regression of human lymphoma xenografts in immunodeficient mice", Blood 97, (2001) vol. 97, No. 12, pp. 3746-3754. Cited in Specification. (10 pages).
Galanis et al., "Phase I Trial of Intraperitoneal Administration of an Oncolytic Measles Virus Strain Engineered to Express Carcinoembryonic Antigen for Recurrent Ovarian Cancer", Cancer Research (2010), 70(3): pp. 875-882. Cited in Specification. (15 pages).
Dorig et al., "The Human CD46 Molecule is a Receptor for Measles Virus (Edmonston Strain)", Cell (1993), vol. 75, pp. 295-305, Cited in Specification. (11 pages).
Naniche et al., "Human Membrane Cofactor Protein (CD46) Acts as a Cellular Receptor for Measles Virus", Journal of Virology, (1993) vol. 67, No. 10, pp. 6025-6032, Cited in Specification. (8 pages).
Tatsuo et al., "SLAM (CDw150) is a cellular receptor for measles virus", Nature (2000) vol. 406, pp. 893-897. Cited in Specification. (5 pages).
Mühlebach et al., "Adherens junction protein nectin-4 (PVRL4) is the epithelial receptor for measles viru", Nature (2012) vol. 480, (7378), pp. 530-533. Cited in Specification. (15 pages).
Noyce et al., "Tumor Cell Marker PVRL4 (Nectin 4) Is an Epithelial Cell Receptor for Measles Virus", PATHOGENS (2011), vol. 7, issue 8, e1002240. Cited in Specification. (24 pages).
Liszewski et al., "Membrane Cofactor Protein (MCP or CD46): Newest Member of the Regulators of complement Activation Gene Cluster", Annual Review of Immunology (1991), vol. 9, pp. 431-455. Cited in Specification. (25 pages).
Fishelson et al., "Obstacles to cancer immunotherapy: expression of membrane complement regulatory proteins (mCRPs) in tumors", Molecular Immunology (2003), vol. 40, pp. 109-123. Cited in Specification. (15 pages).
Takano et al., "Identification of Nectin-4 Oncoprotein as a Diagnostic and Therapeutic Target for Lung Cancer", Cancer Research (2009) vol. 69, pp. 6694-6703. Cited in Specification. (11 pages).
Fabre-Lafay et al., "Nectin-4 is a new histological and serological tumor associated marker for breast cancer", BMC Cancer (2009), vol. 69, 6694-6703. Cited in Specification. (16 pages).
Fabre-Lafay et al., "Nectin-4, a New Serological Breast Cancer Marker, Is a Substrate for Tumor Necrosis Factor-alpha-converting Enzyme (TACE)/ADAM-17", The Journal of Biological Chemistry, (2005) vol. 280, No. 20, pp. 19543-19550. Cited in Specification. (9 pages).
Derycke et al., "Nectin 4 Overexpression in Ovarian Cancer Tissues and Serum", American Society for Clinical Pathology, (2010) vol. 134, pp. 835-845. Cited in Specification. (17 pages).
Raymond et al., "Nectin4/PRR4, a New Afadin-associated Member of the Nectin Family That Trans-interacts with Nectin1/PRR1 Through V Domain Interaction", The Journal of Biological Chemistry, (2001) vol. 276, No. 46, pp. 43205-43215. Cited in Specification. (12 pages).
Delpeut et al., "Host factors and measles virus replication", Current Opinion in Virology (2012), vol. 2, pp. 773-783. Cited in Specification. (11 pages).
Sugiyama et al., "Measles virus selectively blind to signaling lymphocyte activiation molecule as a novel oncolytic virus for breast cancer treatment", Gene Therapy (2013), vol. 20, pp. 338-347. Cited in Specification. (10 pages).
International Search Report dated Dec. 8, 2015, issued in counterpart of International Application No. PCT/JP2015/076817. (2 pages).

* cited by examiner

[Figure 1]
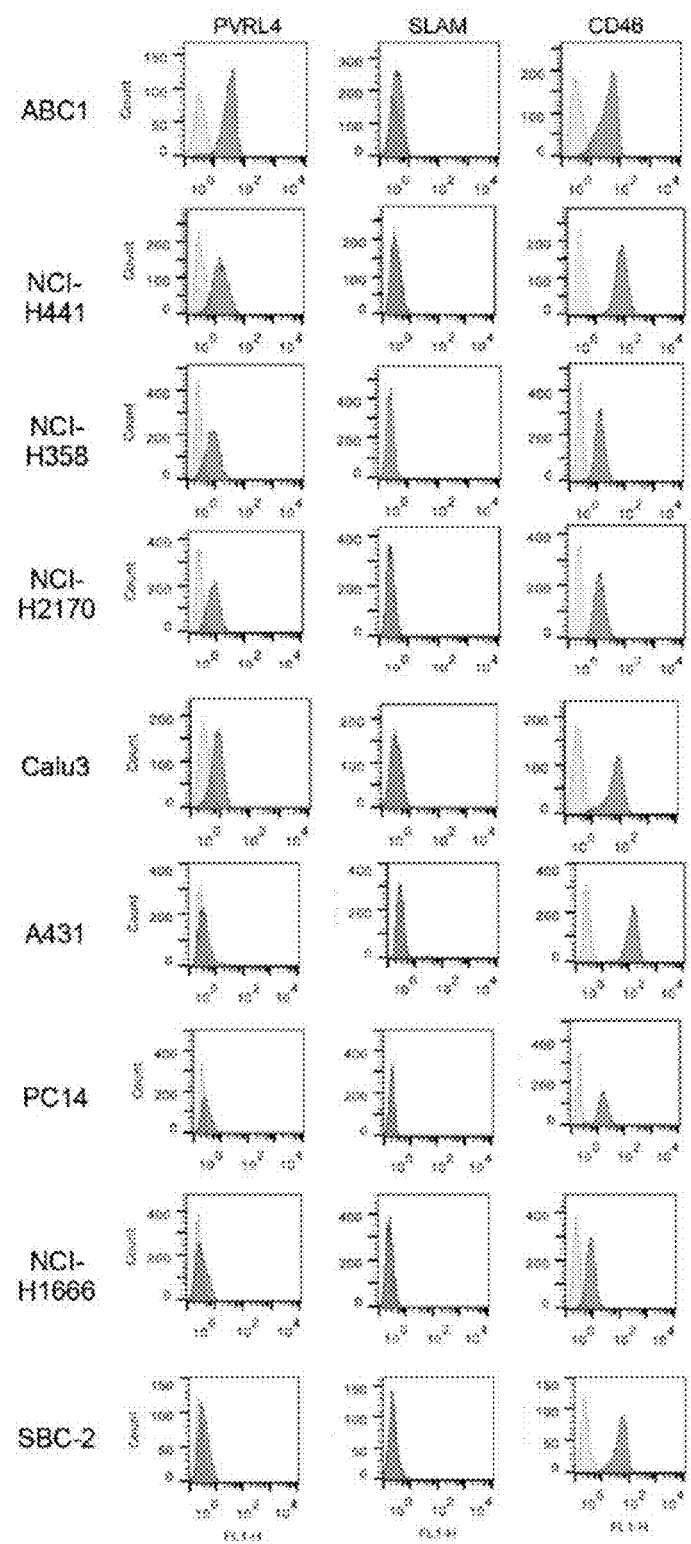

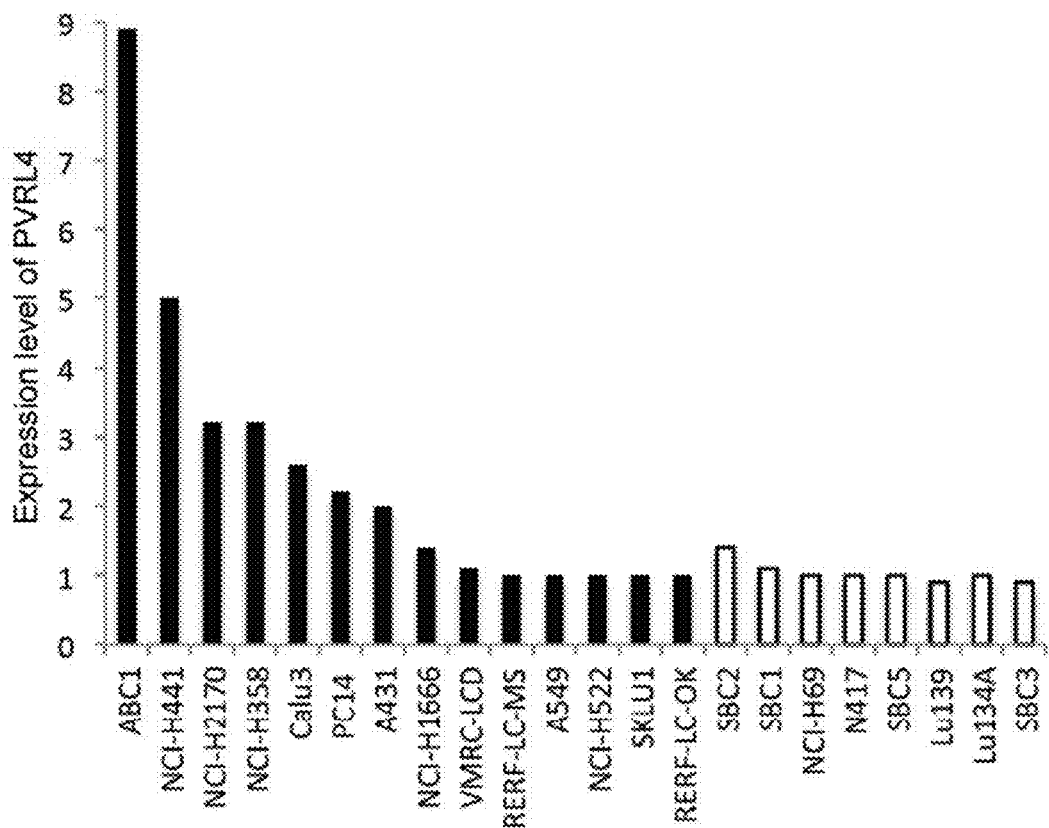
[Figure 2]

[Figure 3]
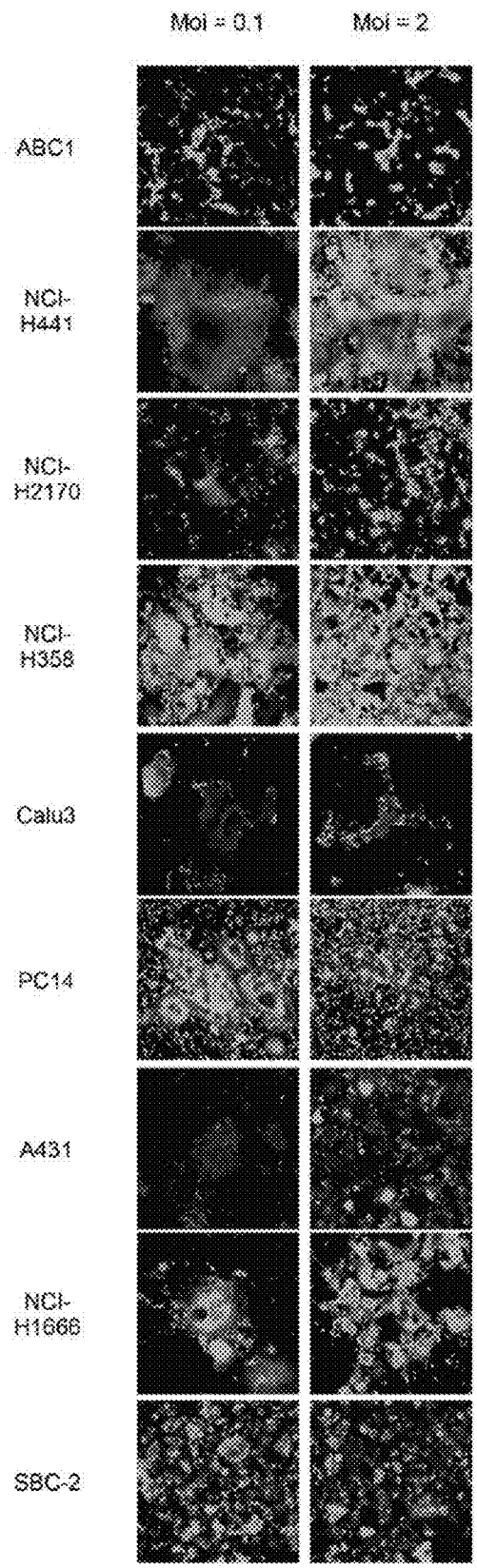

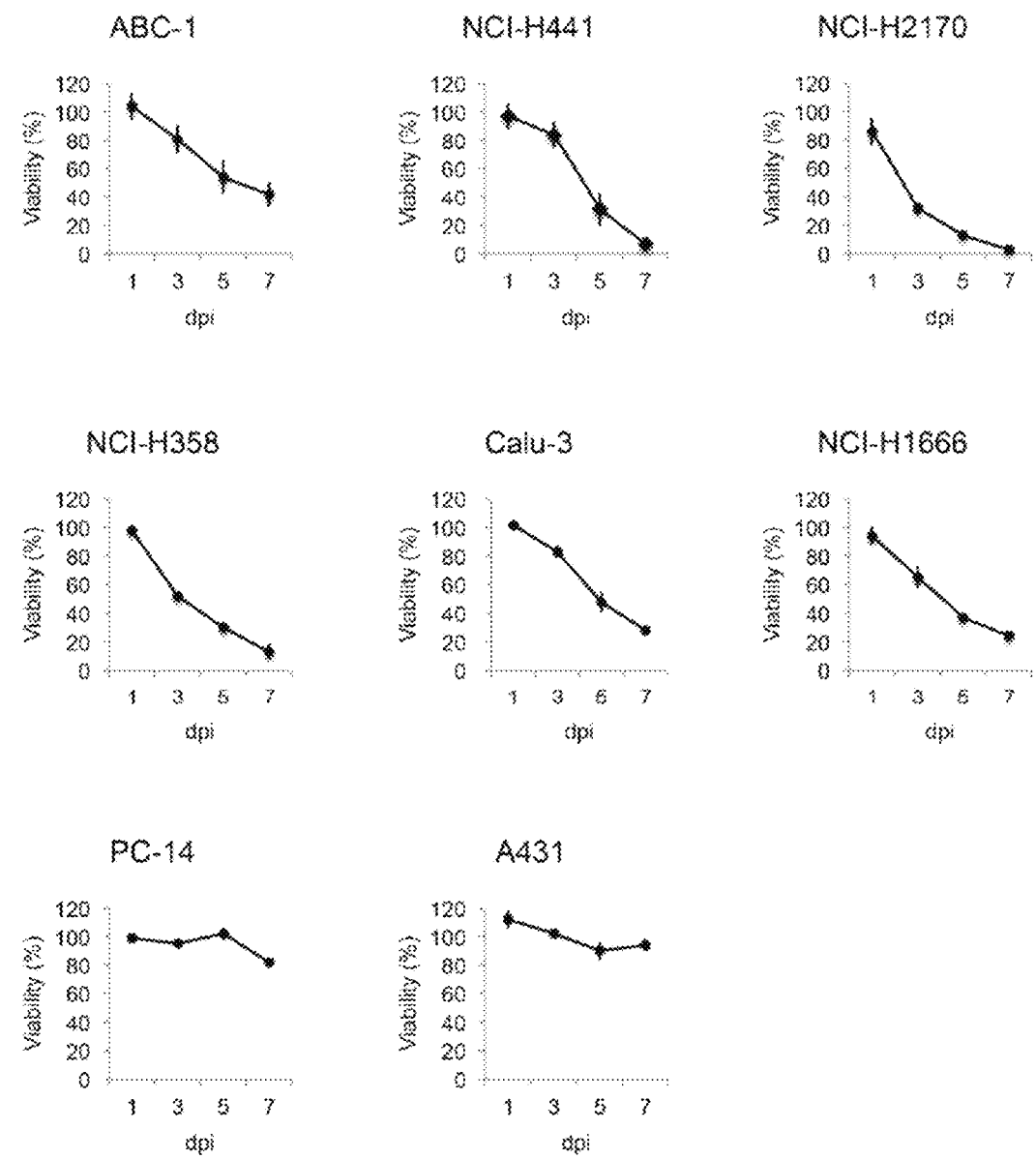
[Figure 4]

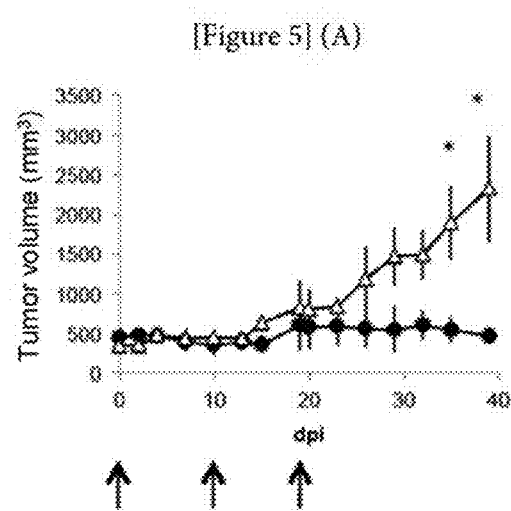
[Figure 5] (A)
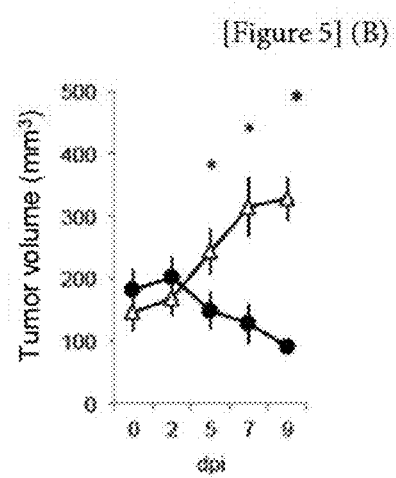
[Figure 5] (B)
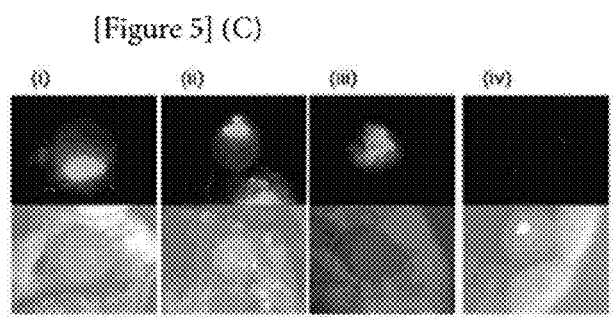
[Figure 5] (C)
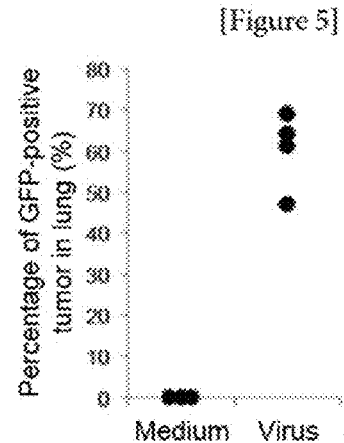
[Figure 5] (D)

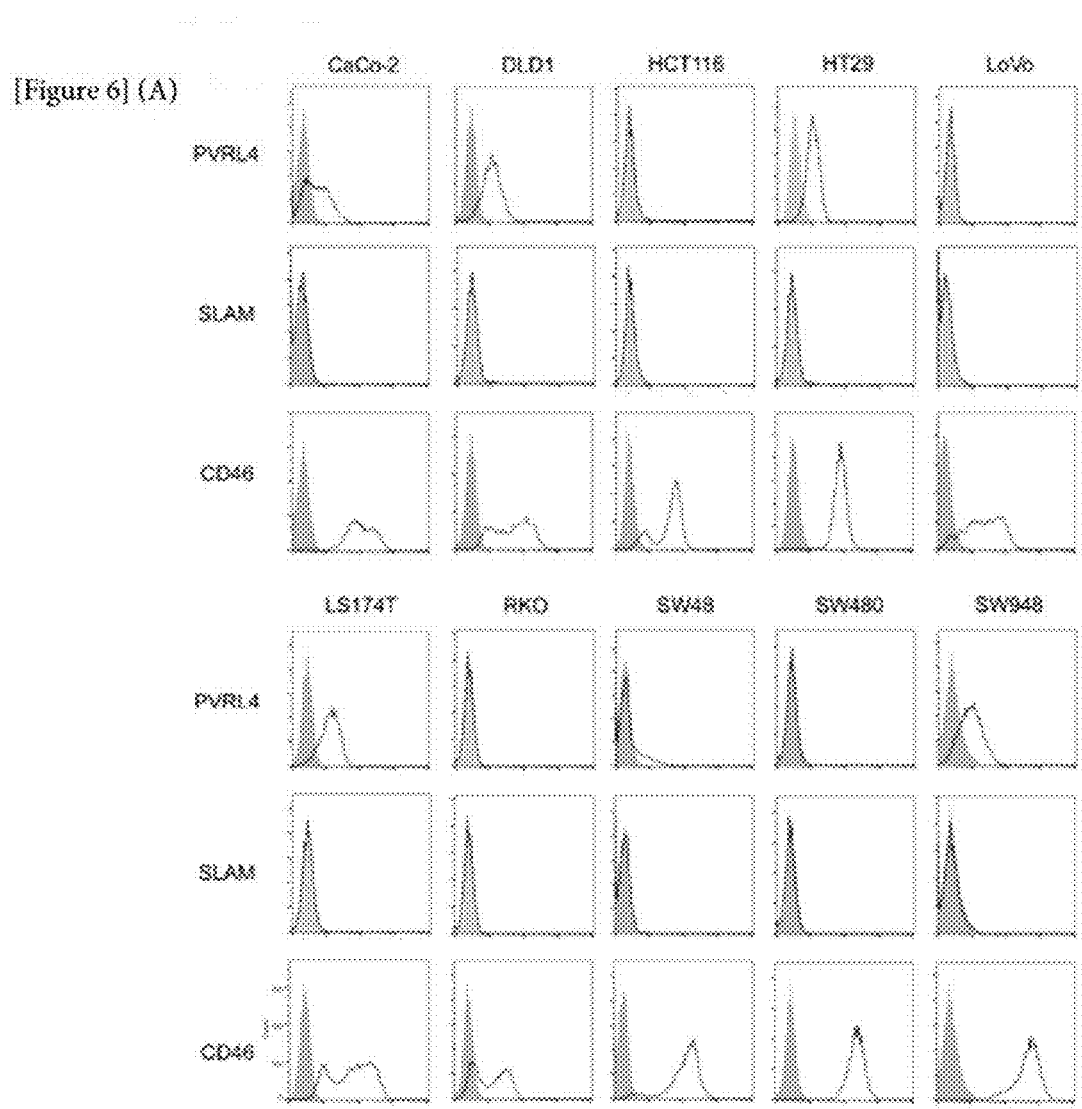
[Figure 6] (A)
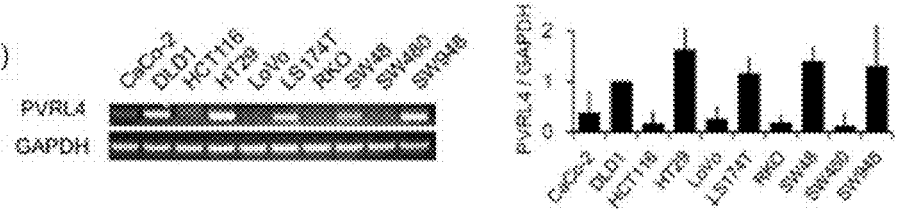
[Figure 6] (B)

[Figure 7] (A)
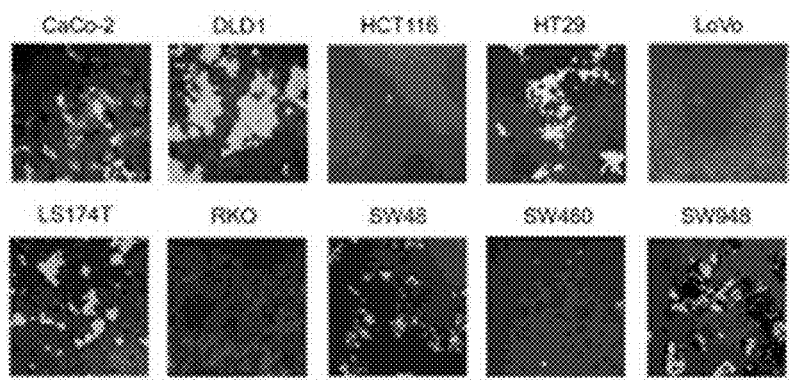
[Figure 7] (B)
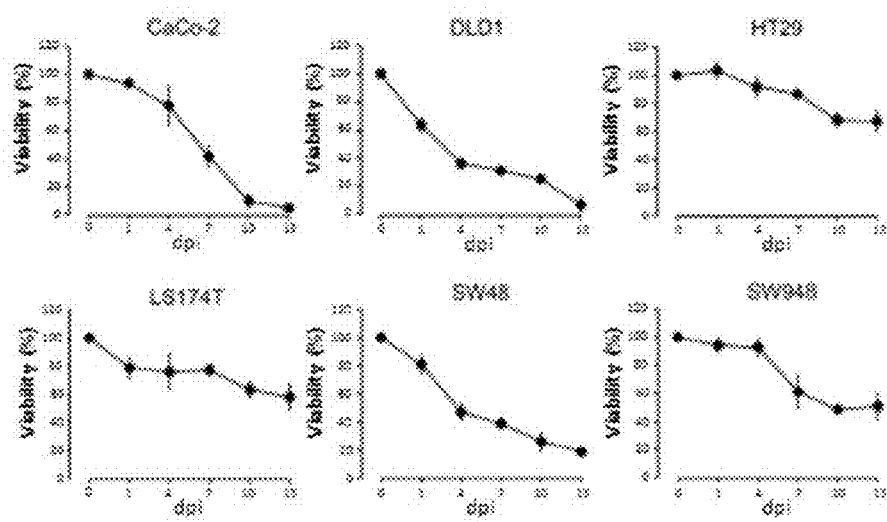
[Figure 7] (C)
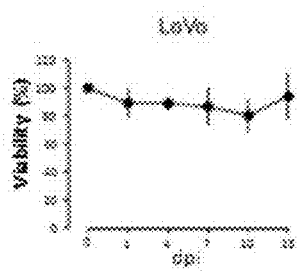

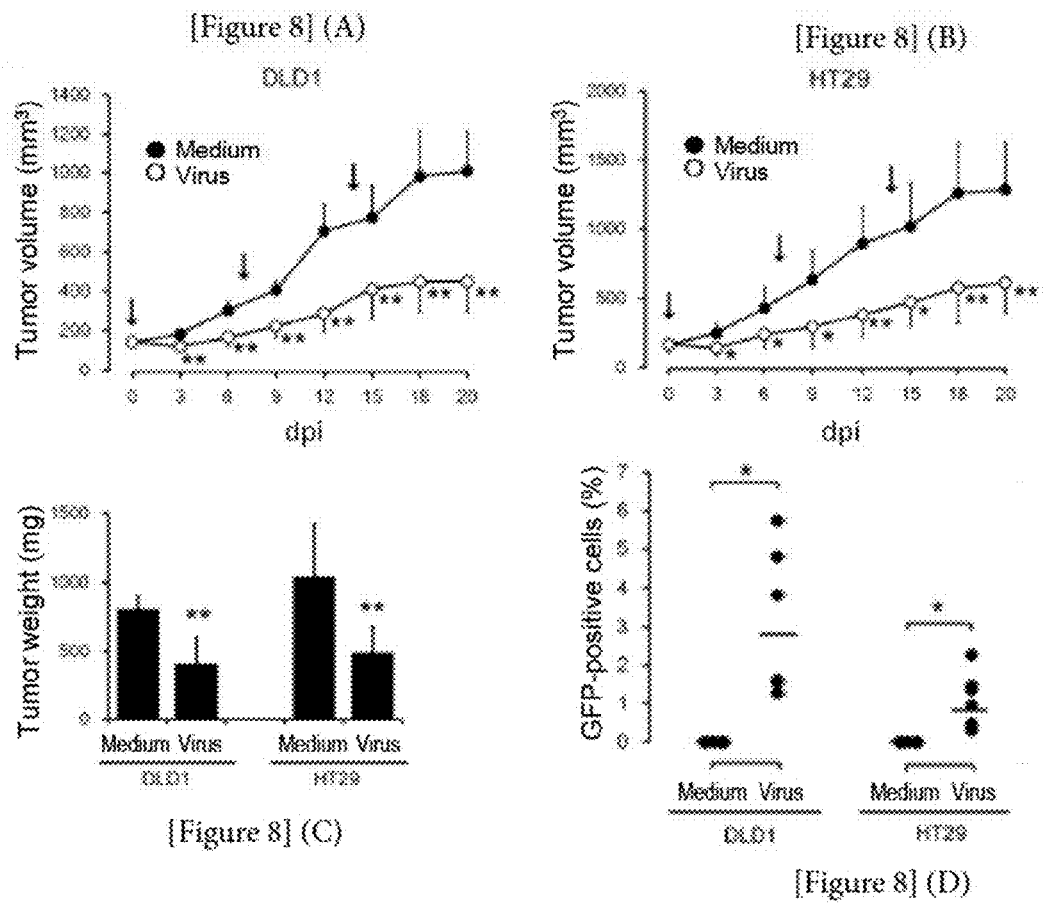
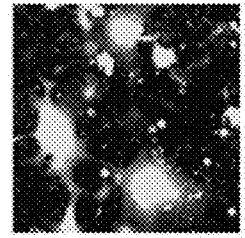

[Figure 10] (A) HCC70

[Figure 10] (B) B95a

[Figure 11] HCC70

1×10⁶TCID₅₀/dose

[Figure 12]
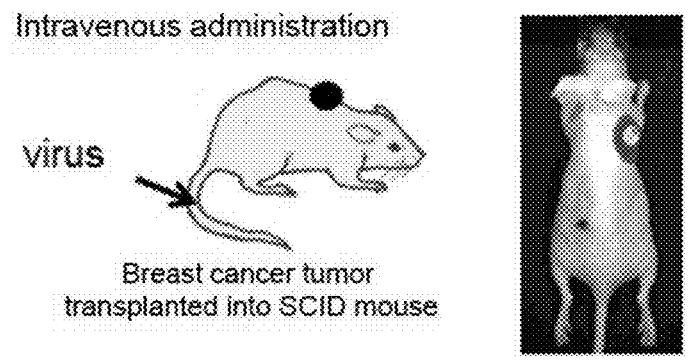
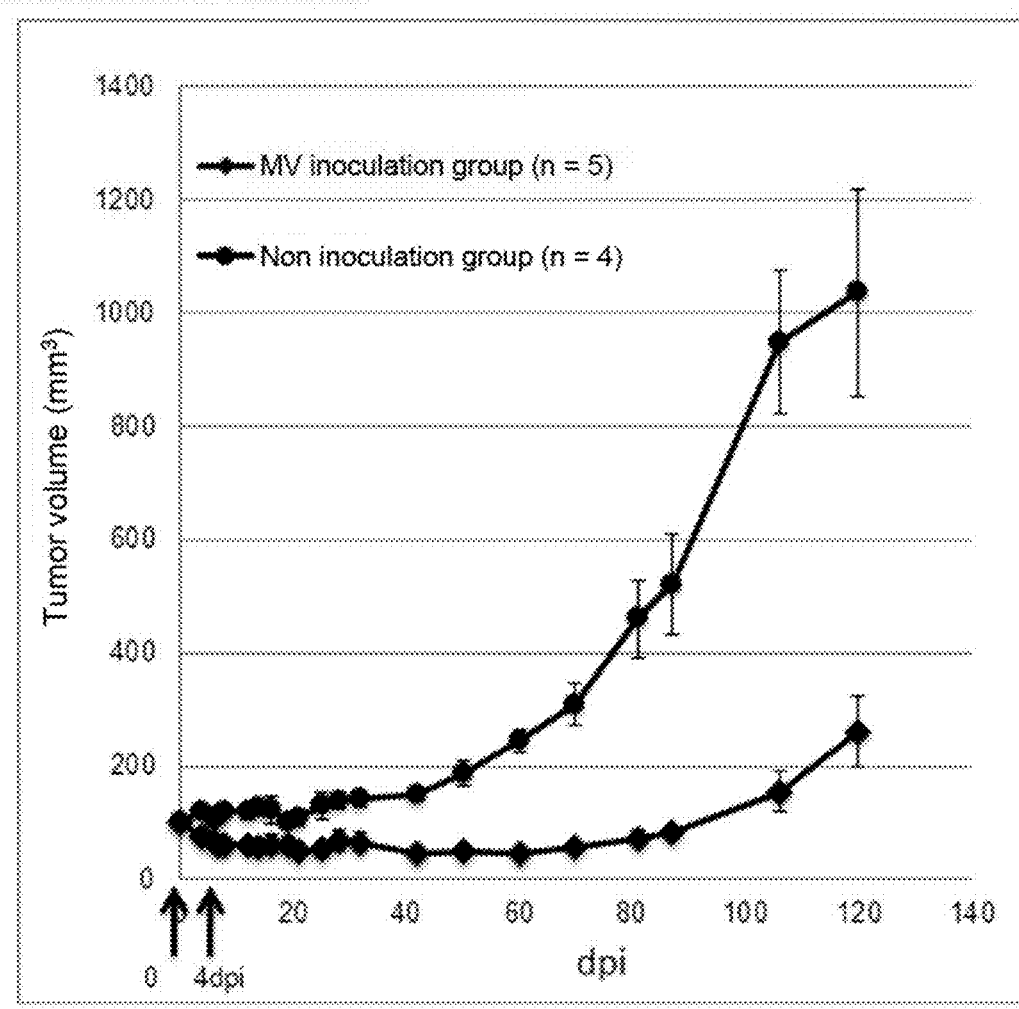

[Figure 13] (A)
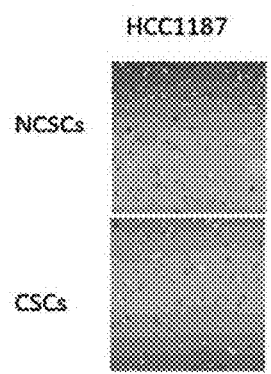
[Figure 13] (B)
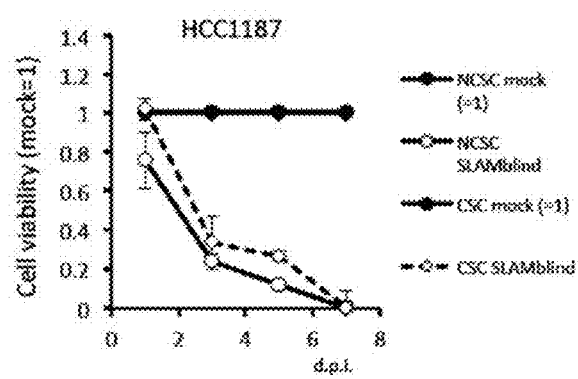
[Figure 14] (A)
Searching for PVRL 4-expressing cells
| Cell | Expression level of PVRL4 |
|---|---|
| 1 | CF33 | ++ |
| 2 | CTBp | ++ |
| 3 | CTBm | ++ |
| 4 | CHMm | ++ |
| 5 | AZACB | − |
| 6 | CHMp | − |
| 7 | CiPp | − |
| 8 | CiPm | − |
| 9 | CbrC | − |
[Figure 14] (B)
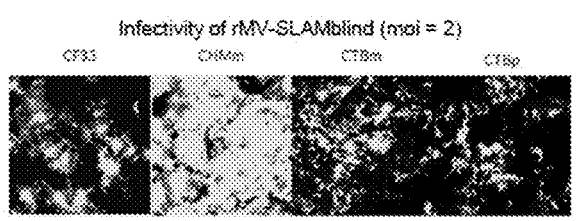
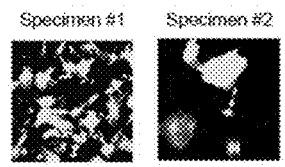
[Figure 14] (C)

[Figure 15] (A)
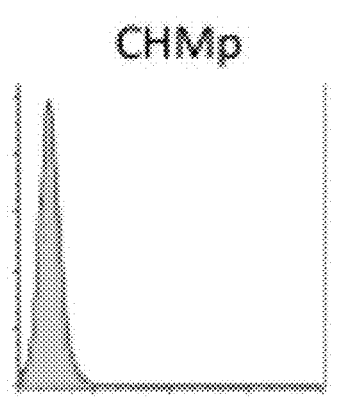
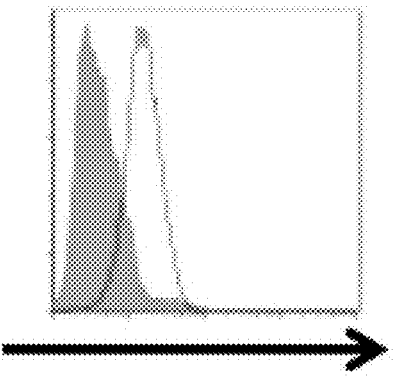
PBRL4-Alexa488
[Figure 15] (B)
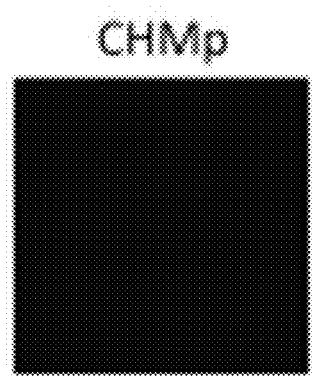
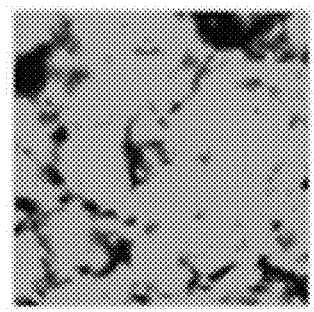

[Figure 16]
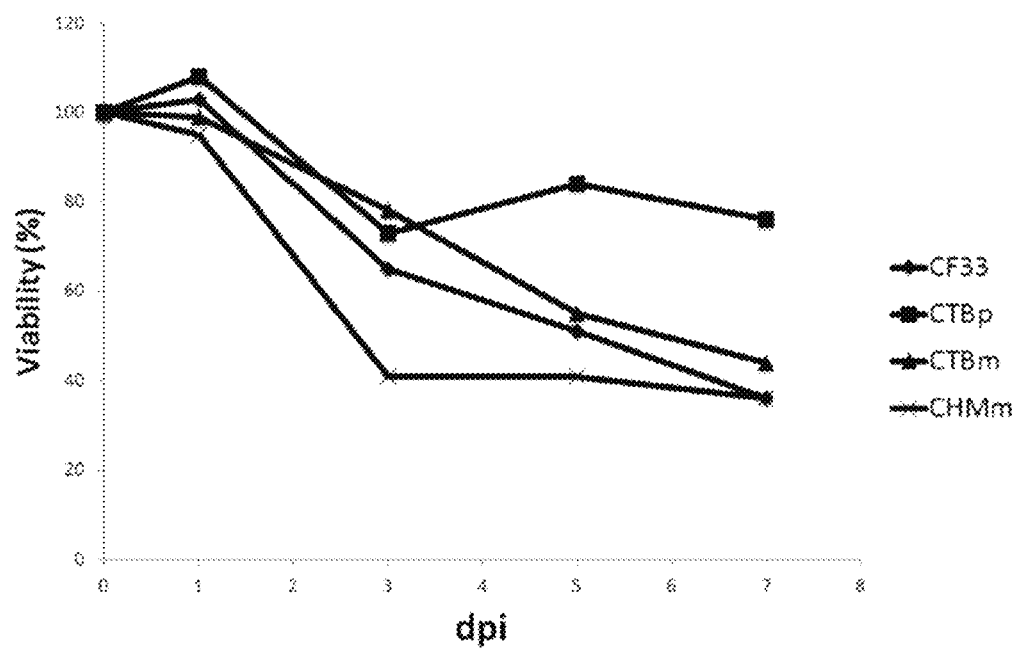

[Figure 17] (A)
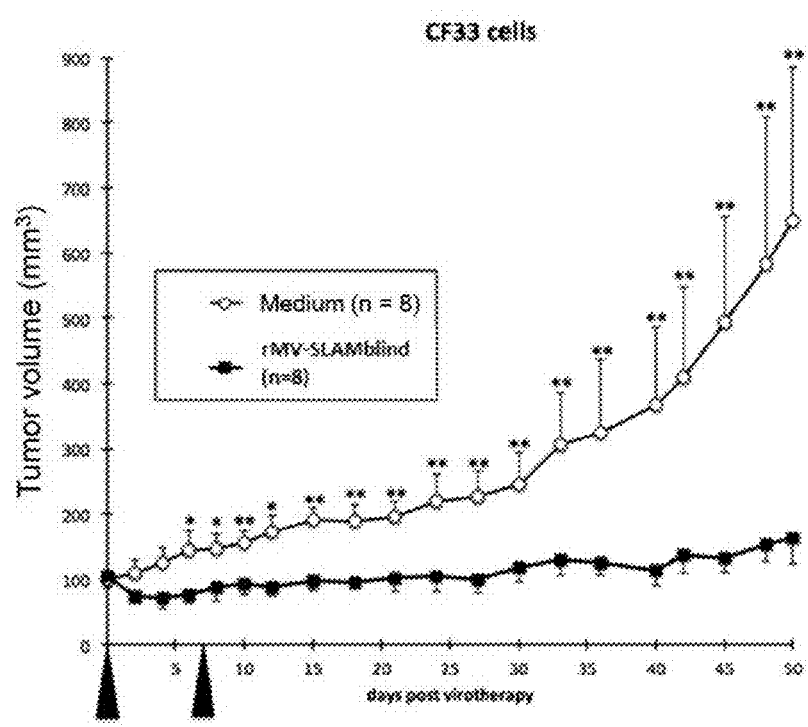
[Figure 17] (B)
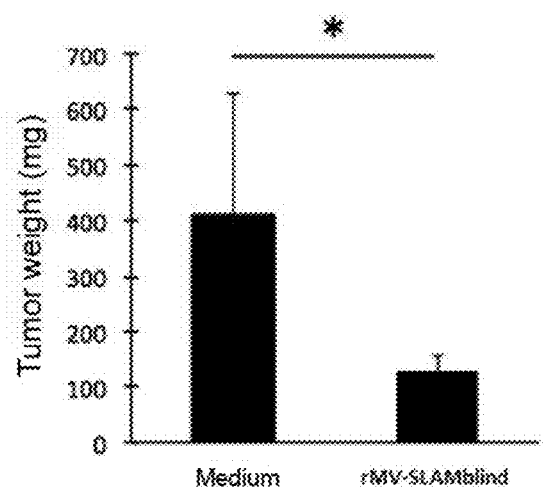

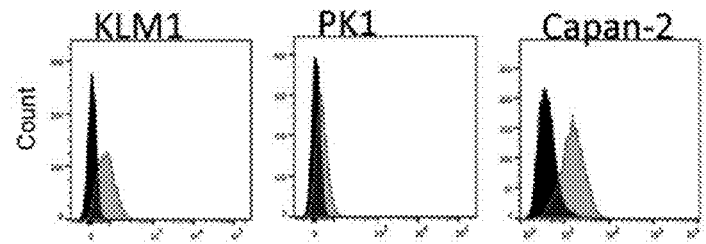
[Figure 18] (A)
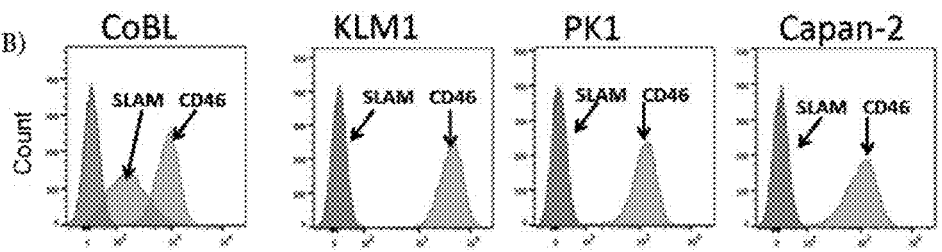
[Figure 18] (B)
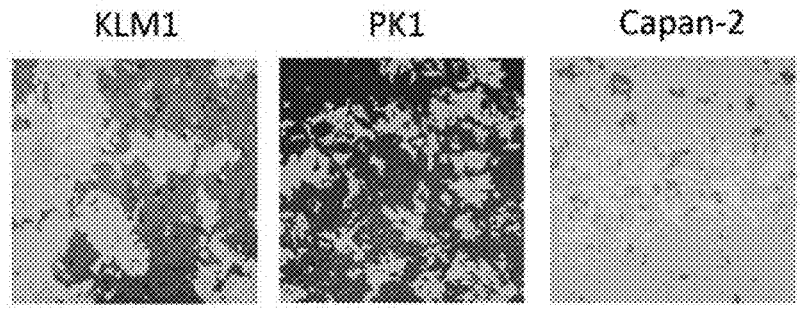
[Figure 19] (A)
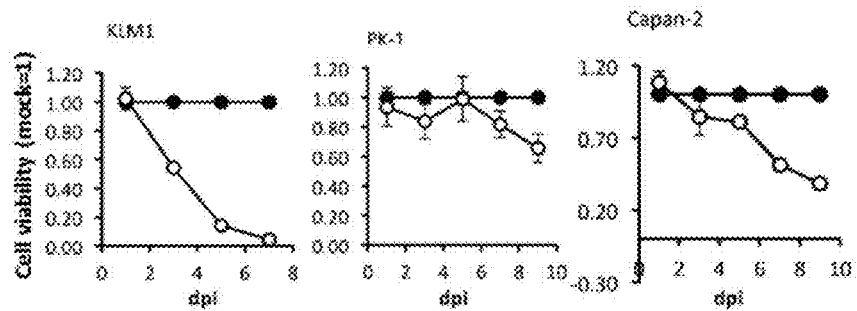
[Figure 19] (B)

[Figure 20] (A)
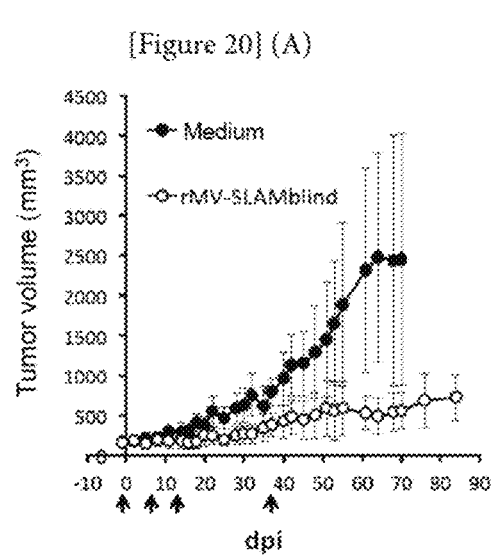
[Figure 20] (B)
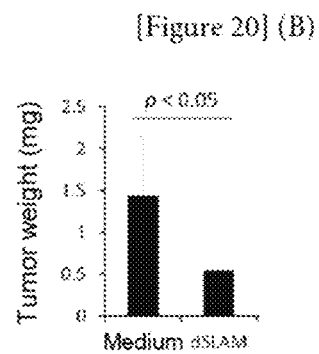
[Figure 20] (D)
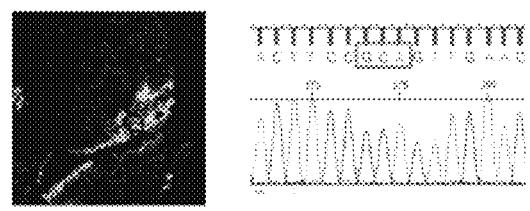
[Figure 20] (C)

GENE-MODIFIED MEASLES VIRUS FOR TUMOR TREATMENT USE

TECHNICAL FIELD

The present invention relates to an oncolytic measles virus, a pharmaceutical composition for use in the treatment of cancer, which comprises the oncolytic measles virus, and a method for treating cancer, which comprises the oncolytic measles virus.

BACKGROUND ART

Measles virus (MV) is a pathogenic virus of the family Paramyxoviridae, genus *Morbillivirus*, which causes immunosuppression or respiratory symptoms to a human who has been infected as a natural host. Since a mechanism whereby tumor cells are infected with the measles virus so that the virus induces regression of the tumor has been revealed (Non Patent Literature 1), the measles virus has attracted attention as a tool used in the virotherapy for cancer. To date, clinical studies regarding the virotherapy of using the measles virus based on vaccine strains have been conducted for ovary cancer and myeloma (Non Patent Literature 2).

Upon infection of host cells with the measles virus, this virus uses three molecules as receptors. These molecules are CD46 (Non Patent Literature 3 and Non Patent Literature 4), SLAM (signaling lymphocyte activation molecule) (Non Patent Literature 5), and PVRL4 (Poliovirus receptor related 4, which is also referred to as "Nectin-4") (Non Patent Literature 6 and Non Patent Literature 7). Vaccine strains of the measles virus can use all of these three molecules as receptors. However, wild-type measles virus strains can use PVRL4 and SLAM, but they cannot use CD46. CD46 is ubiquitously present in human nucleated cells, and in particular, the expression of CD46 is increased in tumor cells (Non Patent Literature 8 and Non Patent Literature 9). Thus, some virotherapy development studies using measles virus vaccine strains have targeted a principal receptor CD46. However, since CD46 is also expressed in normal cells, it has been problematic in terms of side effects and an influence on the infection rate to target tumor cells. Moreover, in the case of subjects who received vaccination, early stage elimination caused by immunity is also concerned.

The expression of PVRL4 is selectively increased in tumor cells including breast cancer cells, ovary cancer cells, and lung cancer cells (Non Patent Literature 10 to Non Patent Literature 13). In general, PVRL4 is expressed in human placenta, and the expression thereof is hardly observed in other tissues (Non Patent Literature 14).

The present inventors have conceived of using a wild-type measles virus strain to selectively target PVRL4. The receptor for the wild-type measles virus exhibiting pathogenicity is SLAM. SLAM is selectively expressed in immune cells, and enables serious immunosuppression by the measles virus and diffusion of the virus to the entire body (Non Patent Literature 15). Hence, the inventors have produced a recombinant measles virus that does not recognize SLAM (rMV-SLAMblind), based on the wild-type measles virus strain HL (Non Patent Literature 16 and Patent Literature 1). When breast cancer cells are infected with rMV-SLAMblind in vitro or in vivo, the cancer cells can be killed. The antitumor activity of rMV-SLAMblind is higher than that of conventional measles virus vaccine strains. In addition, rMV-SLAMblind has been completely attenuated, and thus, it has been confirmed that rMV-SLAMblind does not cause the typical clinical symptoms of measles, when it is subcutaneously inoculated into a monkey, and thus that this recombinant virus is highly safe (Non Patent Literature 16 and Patent Literature 1).

As stated above, a recombinant measles virus that does not recognize SLAM, rMV-SLAMblind, is expected to be an extremely effective tool for cancer therapy. In particular, rMV-SLAMblind is greatly expected for the treatment of, not only primary cancer, but also metastatic cancer, and it is also greatly expected to have cytotoxic effects on cancer stein cells.

CITATION LIST

Patent Literature

Patent Literature 1: JP Patent Publication (Kokai) No. 2013-216609 A

Non Patent Literature

Non Patent Literature 1: Grote et al., Blood 97: 3746-3754 2001.
Non Patent Literature 2: Galanis et al., Cancer research 70: 875-882 2010.
Non Patent Literature 3: Dorig et al., Cell 75: 295-305 1993
Non Patent Literature 4: Naniche et al., Journal of virology 67: 6025-6032 1993
Non Patent Literature 5: Tatsuo et al., Nature 406: 893-897 2000
Non Patent Literature 6: Muhlebach et al., Nature 480: 530-533 2011
Non Patent Literature 7: Noyce et al., PLoS pathogens 7: e1002240 2011
Non Patent Literature 8: Liszewski et al., Annual review of immunology 9: 431-455 1991
Non Patent Literature 9: Fishelson et al., Molecular immunology 40: 109-123 2003
Non Patent Literature 10: Takano et al., Cancer research 69: 6694-6703 2009
Non Patent Literature 11: Fabre-Lafay et al., BMC cancer 7: 73 2007
Non Patent Literature 12: Fabre-Lafay et al., The Journal of biological chemistry 280: 19543-19550 2005
Non Patent Literature 13: Derycke et al., American journal of clinical pathology 134: 835-845 2010
Non Patent Literature 14: Reymond et al., The Journal of biological chemistry 276: 43205-43215 2001
Non Patent Literature 15: Delpeut et al., Current opinion in virology 2: 773-783 2012
Non Patent Literature 16: Sugiyama et al., Gene therapy 20: 338-347 2013

SUMMARY OF INVENTION

Technical Problem

Under the aforementioned circumstances, the present inventors have conducted more detailed studies regarding whether or not the recombinant measles virus that does not recognize SLAM exhibits effects on various cancers other than breast cancer and whether or not the recombinant measles virus exhibits therapeutic effects on difficult-to-treat cancers (e.g., metastatic cancer, triple-negative breast cancer, etc.).

Hence, it is an object of the present invention to provide a medicament or a pharmaceutical composition, which is effective for the treatment of various cancers.

Solution to Problem

The present inventors have conducted various studies regarding cancers as therapeutic targets of a medicament or a pharmaceutical composition comprising a recombinant measles virus that does not recognize SLAM, by using rMV-SLAMblind or rMV-V(−)-SLAMblind as such a recombinant measles virus that does not recognize SLAM. As a result, the inventors have found that triple-negative breast cancer, which is considered to be extremely difficult to be treated, and metastatic cancer, can be treated using such a medicament or a pharmaceutical composition. Moreover, the present inventors have also found for the first time that such a medicament or a pharmaceutical composition comprising a recombinant measles virus that does not recognize SLAM exhibits tumor regression effects not only by intratumoral administration but also by intravenous administration, and that the medicament or the pharmaceutical composition exhibits tumor regression effects even at a lower dose than those of conventional viral drugs.

Based on the aforementioned findings, the present invention has been completed.

Specifically, the present invention includes the following (1) to (6):
(1) A pharmaceutical composition for use in the treatment of cancer, comprising rMV-SLAM-blind or rMV-V(−)-SLAM-blind.
(2) The pharmaceutical composition according to claim 1, which wounds and kills cancer stem cells.
(3) The pharmaceutical composition according to claim 1, wherein the cancer is refractory cancer.
(4) The pharmaceutical composition according to any one of the above (1) to (3), wherein the cancer is metastatic cancer.
(5) The pharmaceutical composition according to any one of the above (1) to (4), wherein the cancer is triple-negative breast cancer, pancreatic cancer, lung cancer, or colon cancer.
(6) The pharmaceutical composition according to any one of the above (1) to (5), which is characterized in that it is used by intravenous administration of the rMV-SLAM-blind or the rMV-V(−)-SLAM-blind.
(7) The pharmaceutical composition according to any one of the above (1) to (6), which is characterized in that the therapeutic target is a dog.

Advantageous Effects of Invention

According to the present invention, it becomes possible to develop a medicament or a pharmaceutical composition for use in the treatment of difficult-to-treat cancer. In addition, according to the present invention, it becomes possible to treat various types of cancers.

BRIEF DESCRIPTION OF DRAWINGS

FIG. 1 shows the expression states of measles virus receptors in lung cancer cell lines. This figure shows the results obtained by analyzing the expression status of each measles virus receptor on the cell surface, using flow cytometry (measles virus receptor: dark gray graph; isotype control: gray graph).

FIG. 2 shows the expression states of PVRL4 in lung cancer cell lines. The expression of PVRL4 in lung cancer cell lines is indicated as the ratio of MFI (Mean Fluorescent Intensity). The black graphs show the results of non-small cell lung cancer lines, whereas the white graphs show the results of small cell lung cancer lines.

FIG. 3 shows the results obtained by analyzing the infectivity of rMV-SLAMblind to PVRL4-expressing lung cancer cell lines.

Various types of cells were infected with rMV-EGFP-SLAMblind at moi=0.1 or 2. Representative photographs of cells are shown.

FIG. 4 shows the results obtained by analyzing the cytotoxicity of rMV-SLAMblind on lung cancer cells in vitro. Various types of lung cancer cells were infected with rMV-EGFP-SLAMblind at moi=1. The viability of the cells was measured by a WST-1 assay at time points of 1 dpi, 3 dpi, 5 dpi and 7 dpi. The numerical value is shown as a mean value±SD of the values obtained from three times of experiments. Viability: survival rate; and dpi: days post first inoculation.

FIG. 5 shows the antitumor effects of rMV-SLAMblind on xenograft models transplanted with a lung cancer cell line. (FIGS. 5A and 5B) The size of the subcutaneously administered NCI-H441 tumor was measured after the intratumoral administration of rMV-EGFP-SLAMblind. The numerical value is shown as a mean value±SD of the experimental values. *: $p<0.05$. FIG. 5(A): The virus (●) or the medium (△) was further administered at time points of 10 days and 19 days after the initial administration (Day 0) (n=4). FIG. 5(B): The virus (●) or the medium (△) was administered once (n=8 for mock (medium), and n=9 for viral administration). FIG. 5(C): NCI-H441/CMV-Luc cells were transplanted into mice by intravenous administration. The rMV-EGFP-SLAMblind was intravenously administered over several administrations. FIG. 5(C): The lung and tumor of the mice, to which the virus (i-iii) or the medium (iv) had been administered, were observed under a fluorescence microscope. FIG. 5(D): The percentage of tumor cells emitting fluorescence in the lung was shown. Each dot indicates the data of each mouse.

FIG. 6 shows the expression states of measles virus receptors in colon cancer cell lines. FIG. 6(A): The expression of the measles virus receptors on the cell surface was analyzed by flow cytometry (measles virus receptor: white graph; and isotype control: gray graph). FIG. 6(B) shows the results of the RT-PCR analysis performed on individual colon cancer cell lines. The left view shows the results obtained by electrophoresing the PCR products. The right view shows the ratio of the expression level of PVRL4 to the expression level of GAPDH. The value is shown as a PVRL4/GAPDH±SD value from three times of experiments. The PVRL4/GAPDH value in DLD1 cells is set at 1.

FIG. 7 shows the results obtained by analyzing the infectivity of rMV-SLAMblind to colon cancer cell lines. FIG. 7(A): The cells were infected with rMV-EGFP-SLAM-blind at moi=2. Representative fluorescence microscopic photographs of cells are shown. FIG. 7(B) shows the viability of PVRL4-positive cells. Viability: survival rate; and dpi: days post first inoculation. FIG. 7(C) shows the viability of PVRL4-negative cells. Regarding FIGS. 7(B) and 7(C), the cells were infected with rMV-EGFP-SLAMblind at moi=2, and a WST assay was then carried out for the dpi shown in the graph. The numerical value is shown as a mean value±SD of the values obtained from three times of experiments.

FIG. 8 shows the antitumor effects of rMV-SLAMblind on xenograft models transplanted with colon cancer cell lines. (FIGS. 8A and 8B) The volume of the graft of each of subcutaneously administered DLD1 cells (FIG. 8A) and HT29 cells (FIG. 8B) was a value measured after the intratumoral administration of rMV-EGFP-SLAMblind. The numerical value is shown as a mean value±SD of the experimental values. *, **p<0.05, p<0.01. The virus (○) or the medium (●) was further administered at time points of 7 days and 14 days after the initial administration (Day 0) (n=7). dpi: days post first inoculation. FIG. 8(C): On the 20th day after the first infection, the mice were euthanized, and the weight of the tumor derived from each of the DLD1 cells and the HT29 cells was then measured. FIG. 8(D) shows the percentage of cells emitting fluorescence. Each dot indicates the data of each mouse (n=7 in each group). *, p<0.05.

FIG. 9 shows the expression states of PVRL4 in triple-negative breast cancer cell lines. FIG. 9(A) shows the results demonstrating the presence or absence of the expression of PVRL4 on the cell surface. FIG. 9(B) shows the results obtained by analyzing the infectivity of rMV-EGFP-SLAM-blind to the triple-negative breast cancer cell line. A representative photograph of cells is shown.

FIG. 10 shows the results obtained by analyzing the cytotoxicity of rMV-SLAMblind to triple-negative breast cancer cells in vitro. Triple-negative breast cancer cells were infected with rMV-EGFP-SLAMblind and rMV-V(−)-EGFP-SLAMblind. FIG. 10(A): The viability of the triple-negative breast cancer cells HCC70 was measured at time points of 1 dpi, 3 dpi, 5 dpi, 7 dpi and 9 dpi according to a WST-1 assay. FIG. 10(B) shows the results obtained by measuring the viability of the control cells B95a that did not express PVRL4. The numerical value is shown as a mean value±SD of the values obtained from three times of experiments. Viability: survival rate; and dpi: days post first inoculation.

FIG. 11 shows the antitumor effects of rMV-SLAMblind and rMV-V(−)-SLAMblind on xenograft models transplanted with a triple-negative breast cancer cell line. The volume of a tumor in which the subcutaneously administered HCC70 had grown (Tumor volume) was measured. The numerical value is shown as a mean value±SD of the experimental values. $1 \times 10^6$ $TCID_{50}$ of rMV-SLAMblind, rMV-V(−)-SLAMblind or medium (control) was further administered at time points of 7 days and 17 days after the initial administration (Day 0). Days after first viral administration: the number of days after the initial viral administration.

FIG. 12 shows the results obtained by examining the effects of the intravenous administration of rMV-SLAMblind to a breast cancer cell-derived tumor. rMV-SLAMblind was further administered at a time point of 4 days after the initial administration (Day 0).

FIG. 13 shows the results obtained by analyzing the cytotoxicity of rMV-SLAMblind on breast cancer-derived cancer stem cells. FIG. 13(A) shows the results obtained by analyzing the infectivity of rMV-EGFP-SLAMblind to cancer stem cells. FIG. 13(B): The viability of HCC1187 cells, which had been infected with rMV-SLAMblind, was measured at time points of 1 dpi, 3 dpi, 5 dpi and 7 dpi according to a WST-1 assay. In the figure, the terms "NCSC mock" and "CSC mock" mean the viability of non-cancer stem cells (NCSC) and cancer stem cells (CSC), when treated with the medium, respectively. The terms "NCSC SLAM blind" and "CSC SLAM blind" mean the viability of non-cancer stem cells (NCSC) and cancer stem cells (CSC), when treated with rMV-SLAM blind, respectively. The cell viability is shown, while the value of mock (medium) is set at 1. Cell viability: the survival rate of cells; and d.p.i.: days post first inoculation.

FIG. 14 shows the expression status of PVRL4 in dog breast cancer cells. FIG. 14(A) shows the results demonstrating the presence or absence of the expression of PVRL4 on the cell surface. FIGS. 14(B) and 14(C) show the results obtained by analyzing the infectivity of rMV-EGFP-SLAMblind to dog breast cancer cell lines (FIG. 14B) and to primary culture cell lines (FIG. 14C). Representative photographs of cells are shown.

FIG. 15 shows a comparison between the infectivity of rMV-SLAMblind to a primary cancer-derived dog breast cancer cell line and the infectivity of rMV-SLAMblind to a metastatic cancer-derived dog breast cancer cell line. FIG. 15(A) shows the results demonstrating the presence or absence of the expression of PVRL4 on the surface of CHMp cells (derived from a primary cancer) and on the surface of CHMm cells (derived from a metastatic cancer). FIG. 15(B) shows the results obtained by analyzing the infectivity of rMV-EGFP-SLAMblind to the CHMp cells and the CHMm cells.

FIG. 16 shows the results obtained by analyzing the cytotoxicity of rMV-SLAMblind on dog breast cancer cell lines in vitro. Various types of cells were infected with rMV-EGFP-SLAMblind, and the viability was then measured at time points of 1 dpi, 3 dpi, 5 dpi and 7 dpi according to a WST-1 assay. Viability: survival rate; and dpi: days post first inoculation.

FIG. 17 shows the antitumor effects of rMV-SLAMblind on xenograft models transplanted with a dog breast cancer cell line. FIG. 17(A): The volume of a tumor, in which a dog breast cancer-derived cell line CF33 subcutaneously transplanted into an immunodeficient mouse had grown, was measured. The numerical value is shown as a mean value±SD of the experimental values. $1 \times 10^6$ $TCID_{50}$ of rMV-SLAMblind (n=8) or medium (n=8) was further administered at a time point of 6 days after the initial administration (Day 0). FIG. 17(B) shows the weight of a tumor collected on the 50th day after the initial viral administration in the experiment of FIG. 17(A). The numerical value is shown as a mean value±SD of the experimental values.

FIG. 18 shows the expression states of PVRL4 on the surface of human pancreatic cancer cells. FIG. 18(A) shows the results demonstrating the presence or absence of the expression of PVRL4 on the surface of cells (KLM1, PK1 and Capan-2). FIG. 18(B) shows the results demonstrating the presence or absence of the expression of SLAM and CD46 on the surface of cells (KLM1, PK1 and Capan-2). The CoBL cells are cells in which SLAM and CD46 are expressed. As a positive control, the results of the CoBL cells are shown.

FIG. 19 shows the results obtained by analyzing the infectivity and cytotoxicity of rMV-SLAMblind to human pancreatic cancer cell lines in vitro. FIG. 19(A) shows the results obtained by analyzing the infectivity of rMV-EGFP-SLAMblind to the cell lines KLM1, PK1 and Capan-2. FIG. 19(B) shows the results obtained by infecting the cell lines KLM1, PK1 and Capan-2 with rMV-EGFP-SLAMblind, and then measuring the viability of individual cell lines at time points of 1 dpi, 3 dpi, 5 dpi, 7 dpi and 9 dpi according to a WST-1 assay. (○) indicates the results obtained by treating the cells with the virus, and (●) indicates the results obtained by treating the cells with the medium. Cell viability: the survival rate of the cells; and dpi: days post first inoculation.

FIG. 20 shows the antitumor effects of rMV-SLAMblind on xenograft models transplanted with a human pancreatic cancer cell line. FIG. 20(A): The volume of a tumor, in which a human pancreatic cancer-derived cell line KLM1 subcutaneously transplanted into an immunodeficient mouse had grown, was measured. The numerical value is shown as a mean value±SD of the experimental values. 1×10⁶ TCID₅₀ of rMV-SLAMblind (n=7) or medium (control) (n=7) was further administered at time points of 8 days, 14 days and 37 days after the initial administration (Day 0). FIG. 20(B) shows the weight of a tumor collected on the 84th day after the initial viral administration in the experiment of FIG. 20(A). The numerical value is shown as a mean value±SD of the experimental values. FIG. 20(C) shows the results obtained by observing under a fluorescence microscope a frozen section of a tumor excised from a mouse, to which rMV-SLAMblind had been administered. FIG. 20(D) shows the results obtained by analyzing the sequence of the H gene of the virus isolated, on the 47th day after inoculation, from a tumor excised from a mouse, to which rMV-SLAMblind had been administered.

DESCRIPTION OF EMBODIMENTS

One embodiment of the present invention is a medicament or a pharmaceutical composition for use in the treatment of cancers, wherein the medicament or the pharmaceutical composition comprises rMV-SLAMblind or rMV-V(−)-SLAMblind.

The present inventors have confirmed that rMV-SLAMblind and rMV-V(−)-SLAMblind efficiently causes cell death to difficult-to-treat human triple-negative breast cancer cells, other than previously reported breast cancers, and also human lung cancer cells, human colon cancer cells, and further, dog breast cancer cells. Such rMV-SLAMblind and rMV-V(−)-SLAMblind have lost infectivity to SLAM-positive cells, and also, they do not originally exhibit infectivity to CD46-positive cells and do not induce cytotoxic action thereon. On the other hand, since such rMV-SLAMblind and rMV-V(−)-SLAMblind use PVRL4/Nectin-4 (which is principally referred to as "PVRL4" in the present description) as a receptor for infection to cells, they specifically exhibit infectivity to PVRL4-positive cancer cells and induce the cell death thereof. In the cells infected with rMV-SLAMblind or rMV-V(−)-SLAMblind, these viruses grow, destroy the cells, and are then released from the cells, so that cell death can be induced.

The rMV-SLAMblind is a recombinant measles virus generated by substituting the amino acid residue at position 533 in the amino acid sequence of H protein of a measles virus strain, that is, the arginine in a wild-type strain thereof, with alanine. On the other hand, the rMV-V(−)-SLAMblind is a recombinant measles virus generated by substituting the amino acid residue at position 533, arginine, with alanine and further substituting the nucleotides at positions 687 and 690, U and C, in a P gene with C and U, respectively.

The rMV-SLAMblind can be produced, for example, by using a plasmid pMV-HL(7+) encoding the full-length antigenomic cDNA of a wild-type measles virus strain HL, substituting the amino acid residue at position 533, arginine, of the H protein thereof with alanine, to prepare a vector (pMV-SLAMblind), and then applying a reverse genetic method using this vector. The used full-length antigenomic cDNA of a wild-type measles virus strain HL, in which the amino acid residue at position 533, arginine, is substituted with alanine, comprises the nucleotide sequence shown in SEQ ID NO: 1. With regard to the proteins encoded by this nucleotide sequence, the N protein consists of the amino acid sequence shown in SEQ ID NO: 2, the P protein consists of the amino acid sequence shown in SEQ ID NO: 3, the M protein consists of the amino acid sequence shown in SEQ ID NO: 4, the F protein consists of the amino acid sequence shown in SEQ ID NO: 5, the H protein consists of the amino acid sequence shown in SEQ ID NO: 6, and the L protein consists of the amino acid sequence shown in SEQ ID NO: 7. The virus is composed of these proteins.

On the other hand, the rMV-V(−)-SLAMblind can be produced, for example, by using a plasmid pMV-HL(7+) encoding the full-length antigenomic cDNA of a wild-type measles virus strain HL, substituting the amino acid residue at position 533, arginine, of the H protein thereof with alanine, to prepare a vector (pMV-SLAMblind), further inserting two mutations into the P gene of the vector pMV-SLAMblind (i.e., substituting the U at position 687 with C, and the C at position 690 with U) to prepare a vector (pMV-V(−)SLAMblind), and then applying a reverse genetic method using this vector. It is to be noted that the amino acid sequence of a protein encoded by pMV-V(−)SLAMblind is completely the same as that encoded by rMV-SLAMblind.

The original virus strain used to produce such rMV-SLAMblind or rMV-V(−)-SLAMblind may also be another virus strain than the wild-type MV-HL strain. Accordingly, the rMV-SLAMblind or rMV-V(−)-SLAMblind of the present invention is not limited to those in which the above-described pMV-SLAMblind vector or pMV-V(−)SLAMblind vector is utilized.

The medicament and pharmaceutical composition of the present invention effectively exhibit therapeutic effects even on cancers that have metastasized from a primary lesion to other tissues (which are referred to as metastatic cancers). Cancer cells often separate from a site in which they have originally developed, and then invade blood vessels or lymphatic vessels. With the flow of blood or lymph, cancer cells transfer to other organs, and grow therein in some cases. Thus, with regard to metastatic cancers generated in a site different from the primary lesion, it is difficult to predict tissues or organs in a body, at which such metastatic cancers will develop. Hence, there may be a case where it is too late to start treatments when metastasis has been found. Accordingly, in order to kill cancer cells that have metastasized to some tissues in a body, it is necessary to develop a pharmaceutical composition or the like that exhibits killing effects on the cancer cells, not only by intratumoral administration, but also by intravenous administration.

The present inventors have confirmed that the expression level of PVRL4 in metastatic cancer-derived cancer cells is higher than the expression level of PVRL4 in primary lesion-derived cancer cells, and that the efficiency of rMV-SLAMblind to such metastatic cancer-derived cancer cells is increased. In general, it is difficult for the conventional chemotherapy to kill only cancer cells that have systemically metastasized, without affecting normal cells. It is considered that the medicament and pharmaceutical composition of the present invention comprising rMV-SLAMblind or rMV-V(−)-SLAMblind as an active ingredient have higher killing ability, rather, on metastatic cancer-derived cancer cells, than on primary lesion-derived cancer cells, and that the present medicament and pharmaceutical composition exhibit extremely high therapeutic effects on metastatic cancer cells. These effects of rMV-SLAMblind (and rMV-V(−)-SLAMblind) on metastatic cancers have been discovered for the first time by the present inventors.

Moreover, as described in the Examples, the medicament and pharmaceutical composition of the present invention exhibit the effect of killing cancer cells also by intravenous administration. Therefore, the medicament and pharmaceutical composition of the present invention are extremely effective for the treatment of metastatic cancers.

The medicament and pharmaceutical composition of the present invention are able to kill any cancer cells, as long as the cancer cells express PVRL4 on the surface thereof. Regarding the expression of PVRL4 on the surface of cancer cells, PVRL4 does not need to be constantly expressed thereon, and the abundance of PVRL4 on the cell surface may be increased or decreased, depending on a change in the abundance ratio thereof between in the cytoplasm and on the cell surface.

The type of a cancer that can be the therapeutic target of the medicament and pharmaceutical composition of the present invention is not particularly limited. Examples of the cancer as a therapeutic target include colon cancer, lung cancer, pancreatic cancer, and further, reportedly difficult-to-treat breast cancer referred to as "triple-negative breast cancer," among breast cancers. The triple-negative breast cancer means any breast cancer in which receptors for two hormones associated with the onset and growth of breast cancer (i.e., estrogen and progesterone) and one protein (HER2) are negative. Since currently effective hormone therapy and treatments involving anti-HER2 (trastuzumab, etc.) therapy do not exhibit therapeutic effects on the triple-negative breast cancer, this breast cancer is considered to be a difficult-to-treat cancer. The triple-negative breast cancer accounts for 10% to 15% of all of breast cancers, and it results in extremely poor prognosis. In addition, the medicament and pharmaceutical composition of the present invention exhibit effective antitumor effects even on refractory cancers that are resistant to conventional molecular targeted drugs (e.g., DLD1 cell line-derived cancer, etc.). Accordingly, the medicament and pharmaceutical composition of the present invention also have refractory cancers as therapeutic targets (wherein the "refractory cancer" means a cancer whose remission cannot be achieved by chemotherapy and molecular targeted therapy, or a cancer resistant to chemotherapy and molecular targeted therapy).

Moreover, the medicament and pharmaceutical composition of the present invention exhibit excellent killing effects also on cancer stem cells. Cancer stem cells are considered to play an important role in metastasis and the growth of a metastatic cancer at a metastasized site. The cancer stem cells are undifferentiated cells with high malignancy, which have a slow mitotic rate and pluripotency and are resistant to chemotherapy such as anticancer agents or radiotherapy. As such, in order to suppress the metastasis of cancer and the growth of cancer cells at a metastasized site, it is important to effectively kill cancer stem cells. Accordingly, the medicament and pharmaceutical composition of the present invention kill such cancer stem cells, so that they can suppress the metastasis of cancer and the growth of metastatic cancer at a metastasized site.

With regard to the medicament of the present invention, it may be possible to administer to a subject only rMV-SLAMblind and/or rMV-V(−)-SLAMblind as active ingredients of the present medicament. However, in general, it is desired to administer the medicament of the present invention to a subject in the form of a pharmaceutical composition comprising one or two or more pharmaceutical additives with the aforementioned viruses as active ingredients. Furthermore, in addition to such pharmaceutical additives, the pharmaceutical composition of the present invention may also comprise oncolytic viruses, anticancer agents or auxiliary components (e.g., immune checkpoint inhibitors such as CTLA-4 blockers or PD-1 antibodies, inmmunostimulants such as GM-CSF, etc.) with rMV-SLAMblind or rMV-V(−)-SLAMblind as an active ingredient of the present medicament. The type of the present pharmaceutical composition is not particularly limited. The dosage form is not particularly limited, either, and any dosage form can be applied as long as it is suitable for administration of oncolytic virus. The pharmaceutical composition of the present invention can be used, for example, as a liquid agent.

The types of pharmaceutical additives used in the production of the pharmaceutical composition, the ratio of pharmaceutical additives to the active ingredient, and a method for producing the pharmaceutical composition can be appropriately determined by a person skilled in the art, depending on the form of the composition. As such pharmaceutical additives, inorganic or organic substances, or solid or liquid substances can be used. In general, such pharmaceutical additives can be mixed into the pharmaceutical composition in an amount of 1% to 90% by weight based on the weight of the active ingredient. Specific examples of such substances include lactose, glucose, mannit, dextrin, cyclodextrin, starch, sucrose, magnesium aluminometasilicate, synthetic aluminum silicate, carboxymethyl cellulose sodium, hydroxypropyl starch, carboxymethyl cellulose calcium, ion exchange resin, methyl cellulose, gelatin, gum Arabic, hydroxypropyl cellulose, hydroxypropylmethyl cellulose, polyvinyl pyrrolidone, polyvinyl alcohol, light anhydrous silicic acid, magnesium stearate, talc, tragacanth, bentonite, veegum, titanium oxide, sorbitan fatty acid ester, sodium lauryl sulfate, glycerin, fatty acid glycerin ester, purified lanolin, glycerogelatin, polysorbate, macrogol, vegetable oil, wax, liquid paraffin, white petrolatum, fluorocarbon, nonionic surfactant, propylene glycol, and water.

When the pharmaceutical composition of the present invention is produced in the form of an injection, the active ingredient may be dissolved in distilled water for injection, as necessary, together with pH adjusters such as hydrochloric acid, sodium hydroxide, lactose, lactic acid, sodium, sodium monohydrogen phosphate or sodium dihydrogen phosphate, and tonicity agents such as sodium chloride or glucose, and thereafter, the obtained solution may be subjected to aseptic filtration and may be then filled into an ampule. Otherwise, mannitol, dextrin, cyclodextrin, gelatin and the like may also be added to the reaction solution, and the obtained mixture may be then subjected to vacuum-freeze drying, so as to prepare a use-time dissolution type injection. Alternatively, lecithin, polysorbate 80, polyoxyethylene hydrogenated castor oil, and the like are added to the active ingredient, and the obtained mixture is then emulsified in water, so as to prepare an emulsion for injection.

The medicament or pharmaceutical composition of the present invention may be administered to a subject by any administration route, as long as it is an administration route capable of exhibiting oncolytic effects. Examples of the administration route applied herein may include intratumoral administration and intravenous administration.

The applied dose of the medicament or pharmaceutical composition of the present invention and the number of administrations thereof are not particularly limited, and these conditions can be determined, as appropriate, by a physician's discretion, depending on conditions such as therapeutic purpose, the type of cancer, the body weight and age of a patient, and the severity of disease.

Moreover, when the medicament or pharmaceutical composition of the present invention is administered to a subject, it may include various unit dosages. The unit dosage means the content of a predetermined amount of the recombinant measles virus of the present invention, and this unit dosage may be administered to a subject as a single injection, or it may also be continuous injection over a determined period of time. The unit dosage of the present invention has the effect of suppressing tumor enlargement, at a dose smaller than the previously reported effective dose of oncolytic virus (the dose for exhibiting the effect of suppressing tumor enlargement) (Russell et al., Mayo Clin Proceedings, 89(7): 926-33, 2014). When the measles virus of the present invention is administered to a subject by intratumoral administration, the applied dose is, for example, $10^3 TCDID_{50}$ or greater (50% tissue culture infectious dose; see, for example, Reed-Muench method, Reed et al., Am J Hyg 1938, 27: 493-497), $10^4 TCDID_{50}$ or greater, 10 $TCDID_{50}$ or greater, and preferably $10^6 TCDID_{50}$ or greater. From the results of an experiment regarding intratumoral emission intensity (see the after-mentioned Examples), it can be anticipated that the measles virus of the present invention will provide a sufficient effect of suppressing tumor enlargement at a dose of approximately $10^7 TCDID_{50}$.

Furthermore, the present invention includes a therapeutic method, which comprises administering the medicament or pharmaceutical composition of the present invention to a patient and the like (including mammals other than humans) to treat cancer (regression of tumor, etc.). The method for treating cancer of the present invention includes a treatment for the purpose of the regression of the previously developed tumor and a treatment for the purpose of killing metastatic cancer cells when metastasis is predicted. The therapeutic method of the present invention also includes adjunctive therapy performed before or after surgical operations.

The "mammal" as a therapeutic target means any given animal classified into Mammalia. The type of the mammal is not particularly limited, and any mammals may be used. Examples of the mammal used herein include humans, pet animals such as a dog, a cat or a rabbit, and livestock animals such as a bovine, a swine, sheep or a horse. The mammal used herein is preferably a human, a dog, or the like.

Hereinafter, the present invention will be described in more detail in the following examples. However, these examples are not intended to limit the scope of the present invention.

EXAMPLES

Materials and Methods
1. Cells
1-1. Human Lung Cancer Cell Lines
NCI-H358, NCI-H1666 and NCI-H2170 were purchased from ATCC (American Type Culture Collection) (Rockville, Md. USA). NCI-H441/CMV-Luc was purchased from The National Institute of Biomedical Innovation (Osaka, Japan). Cells were maintained in accordance with instruction manuals. ABC-1, Calu-3, A431, PC14, NCI-H441, VMRC-LCD, RERF-LC-MS, NCI-H522, SKLU1, RERF-LC-OK, SBC-1, SBC-2, SBC-3, SBC-5, NCI-H69, N417, Lu139, and Lu134A were maintained by the previously disclosed method (Kikuchi et al., Clinical cancer research 11: 2954-2961 2005). Specifically. ABC-1, Calu-3, RERF-LC-MS, RERF-LC-OK, VMRC-LCD, SK-LU-1, SBC1, SBC2, SBC3 and SBC5 were maintained in MEM (Minimum Essential Medium) containing 10% FCS, 1 mM sodium pyruvate and non-essential amino acid. On the other hand, NCI-H441, NCI-H522, PC-14, NCI-H69, N417, Lu134A and Lu139 were maintained in RPMI 1640 containing 10% FCS.
1-2. Human Colon Cancer Cell Lines
CaCo-2, DLD1, HCT116, HT29, LoVo, LS174, RKO, SW48, SW480 and SW948 were purchased from ATCC (American Type Culture Collection) (Rockville, Md., USA). DLD1, HT29 and SW48 cells were maintained in RPMI 1640 containing 10% FCS. Other cells were maintained in DMEM (Dulbecco's Modified Eagle's medium) (Life Technologies) containing 10% FCS.
1-3. Human Breast Cancer Cell Lines
Triple-negative breast cancer cells, HCC1599, HCC1187, HCC70, MDA-MB-468, HCC38, HCC1143, HCC1937, BT-20, HCC1806, DU4475 and BT549C were purchased from ATCC. BT-20 was maintained in EMEM containing 10% FCS, and other cells were maintained in RPMI containing 10% FCS.

Human breast cancer cells MCF7 (The Cell Resource Center for the Biomedical Research Institute of Development, Aging and Cancer, Tohoku University, Miyagi, Japan) were maintained by a conventional method (Sugiyama et al., Gene therapy 20: 338-347 2013).
1-4. Human Pancreatic Cancer Cell Lines
Capan-2 was obtained from ATCC (ATCC, HTB-80). KLM1 and PK1 were furnished from Dr. Yoichi FURUKAWA, Division of Clinical Genome Research, The Institute of Medical Science, The University of Tokyo.
1-5. Dog Breast Cancer Cell Lines
CF33 was furnished from Department of Veterinary Medicine, College of Bioresource Sciences, Nihon University. On the other hand, CTBp, CTBm, CHMp and CHMm were furnished from Graduate School of Agricultural and Life Sciences, The University of Tokyo, CF33 was maintained in DMEM containing 10% FCS, whereas CTBp, CTBm and CHMmC were maintained in RPMI containing 10% FCS.
2. Viruses
rMV-SLAMblind that retains an EGFP gene (rMV-EGFP-SLAMblind) was prepared by the previously reported method (JP Patent Publication (Kokai) No. 2013-216609 A; Sugiyama et al., Gene therapy 20: 338-347 2013; the disclosures of this application are all incorporated herein by reference). On the other hand, rMV-V(−)-SLAM-blind was prepared by introducing two mutations into the P gene of the genome of rMV-SLAMblind (i.e., the nucleotides at positions 687 and 690, namely, U and C were substituted with C and U, respectively).

MCF7 cells were infected with each of the aforementioned viruses, and the virus-infected cells were harvested with a culture supernatant. Thereafter, an ultrasonic treatment was performed for 8 seconds on the harvested product in three cycles, so that the virus was released. After completion of the ultrasonic treatment, the harvested product was centrifuged at 3,000 rpm (1,940×g) at 4° C. for 10 minutes, so that the virus was recovered in a supernatant. In order to obtain high-titer virus for in vivo administration, the viral solution was concentrated. 200 ml of the viral suspension was centrifuged at 19 k rpm at 4° C. for 2 hours. After completion of the centrifugation, pellets were recovered and were then suspended again in approximately 1 ml of medium, and the obtained suspension was preserved at −70° C. The virus titer was determined as TCID50/ml (50% tissue culture infectious dose) using MCF7 cells, as previously reported (JP Patent Publication (Kokai) No. 2013-216609 A; Sugiyama et al., Gene therapy 20: 338-347 2013).
3. Infection of Cells with Virus
3-1. Infection of Lung Cancer Cell Lines with Virus
Lung cancer cell lines were cultured on a 24-well plate, and were then infected with rMV-EGFP-SLAMblind at moi=0.1 or 2. After completion of the infection, fluorescent signals were observed over time, using a confocal microscope (FV1000, Olympus).

3-2. Infection of Colon Cancer Cell Lines with Virus

Colon cancer cell lines were cultured on a 96-well plate, and were then infected with rMV-EGFP-SLAMblind at moi=2. Three days after the infection, fluorescent signals were observed using a confocal microscope (FV1000, Olympus).

3-3. Infection of Breast Cancer Cell Lines with Viruses

Triple-negative breast cancer cell lines were cultured on a 24-well-plate, and were then infected with rMV-EGFP-SLAMblind at moi=2, or with rMV-V(−)-EGFP-SLAMblind at moi=2. After completion of the infection, fluorescent signals were observed over time, using a confocal microscope (FV1000, Olympus).

Dog breast cancer cell lines were cultured on a 24-well-plate, and were then infected with rMV-EGFP-SLAMblind at moi=2. Moreover, a primary culture cell line, which had been derived from a dog with breast cancer, was cultured on a 24-well-plate, and was then infected with rMV-EGFP-SLAMblind at moi=0.1 or 0.01. After completion of the infection, fluorescent signals were observed over time, using a confocal microscope (FV1000, Olympus).

3-4. Infection of Pancreatic Cancer Cell Lines with Virus

Pancreatic cancer cell lines were infected with rMV-EGFP-SLAMblind at moi=1. Two days after the infection, fluorescent signals were observed using a confocal microscope (FV1000, Olympus).

4. RT-PCR and Sequence Analysis

Colon cancer cells were lyzed with a TRIzol LS reagent (Life Technologies), and total RNA was then extracted in accordance with the instruction manual. cDNA was synthesized using an RT-PCR kit (PrimeScript; Takara). PCR was performed on human PVRL-4 and GAPDH (glyceraldehyde-3-phosphate dehydrogenase), using AmpliTaq polymerase (Life Technologies). The following primers were used in the PCR.

```
PVRL4-specific forward primer;
                            (SEQ ID NO: 8)
5'-ACATCCTCCACGTGTCCTTC-3'

PVRL4-specific reverse primer;
                            (SEQ ID NO: 9)
5'-CAAAGTGTCCCCATCCACTC-3'

GAPDH-specific forward primer;
                            (SEQ ID NO: 10)
5'-CACCCACTCCTCCACCTTTGAC-3'

GAPDH-specific reverse primer;
                            (SEQ ID NO: 11)
5'-GTCCACCACCCTGTTGCTGTAG-3'
```

In order to eliminate the entire coding region of PVRL4, PCR was carried out using LA Taq (Takara). The following primers were used in the PCR.

```
KIT-specific forward primer;
                            (SEQ ID NO: 12)
5'-GGTCAGTTCCTTATTCAAGTCTGC-3'

KIT-specific reverse primer;
                            (SEQ ID NO: 13)
5'-GCTAAAATCTCCCATGTCAACAG-3'
```

The PCR product was cloned into a TA cloning vector (pGEM-T; Promega), and the sequence was then determined. The determined sequence was compared with the sequence registered in GenBank (Accession No. NM030916.2).

5. Flow Cytometry 5-1. Cell Lines

The cells were washed with PBS, and were then removed from the culture plate, using 0.025% trypsin and 0.24 mM EDTA. The recovered cells were centrifuged, and the obtained cell pellets were re-suspended in HBSS (Hank's Balanced Salt Solution) (Life Technologies) containing 2% FCS. The cell suspension was incubated on ice, together with an anti-human Nectin-4 monoclonal antibody (Clone 337516, R&D Systems), anti-PVRL4 mAB (Clone N4.61; Millipore), anti-human SLAM antibody [A12 (7D4) BioLegend, San Diego, Calif.], an anti-CD46 antibody (M177. HyCult Biotech, Uden, Netherland) or mouse IgG (R & D Systems). After completion of the incubation, the cells were washed with PBS containing 2% FCS, and were then incubated on ice together with anti-mouse IgG-Alexa 488 (Life Technologies). Thereafter, the cells were washed with PBS containing 2% FCS, and the fluorescent intensity thereof was then measured using FACSCalibur (BD Biosciences). The mean fluorescent intensity (MFI) of the cells stained with various types of antibodies was divided by the value of an isotype control, and the thus obtained values were then shown to be the relative expression levels of PVRL4/Nectin-4, SLAM and CD46.

5-2. Tumor Cells

A colon cancer cell-derived tumor excised from a mouse was treated with HBSS containing 5 mM HEPES, 2% FCS, 1 mg/mL collagenase (Wako Pure Chemical Industries, Ltd.) and 0.1% DNase I (Life Technologies). Cells collected from the tumor were stained with 7AAD (7-amino-actinomycin D) and anti-mouse H2Kd-PE-Cy7 Ab (clone SF 1-1.1; BD Biosciences), and were then immobilized with 4% paraformaldehyde. Thereafter, the cells were analyzed using BD FACS Verse analyzer (BD Biosciences).

6. Viability of Cells

The viability of the cells was measured using a WST-1 cell growth kit (Takara). The cells of each type were infected with virus at a suitable moi, and were then cultured. At time points of several dpi (days post first inoculation; and so on), the viability of the cells was measured in accordance with the instruction manual included with the WST-1 cell growth kit.

7. Xenograft Models

All of animal experiments were carried out under the approval of the Laboratory Animal Committee, The Institute of Medical Science, The University of Tokyo.

In the case of subcutaneous transplantation, after the transplanted tumor cells had adhered to a transplantation recipient and had grown to a sufficient size (100 mm$^3$ to 250 mm$^3$, and in some cases, 500 mm$^3$), virus was administered thereto to examine the therapeutic effects of the virus. A period of time necessary for the growth of a tumor mass to a sufficient size is different depending on the type of cancer cells and a growth rate thereof.

7-1. Lung Cancer Cell Line

Five-week-old female SCID (severe combined immune deficiency) mice were purchased from CLEA Japan, inc. NCI-H441 cells (lung cancer cell line) were suspended in HBSS containing 2% FCS to result in a cell density of 1×10$^8$ cells/ml, and the obtained suspension was then mixed with an equal volume of Matrigel (BD Biosciences). Thereafter, 100 μl of the cell suspension (5×10$^7$ cells) was subcutaneously injected into SCID mice (5×10$^7$ cells/1 mouse). After completion of the transplantation, at a time point at which a tumor mass had grown to a size of 400 to 500 mm$^3$, viral administration was initiated. A total of three times, namely, on Day 0, Day 10 and Day 19, 10$^6$ TCID$_{50}$ of rMV-EGFP-SLAMblind was administered to the mice by intratumoral administration. The volume of the tumor was calculated by the formula: (width×width×length)/2. Using JMP software (JMP Pro 10.0.2, SAS Institute Inc., Cary, N.C.), the tumor volume was analyzed according to a Wilcoxon-log-rank test. Also, an experiment was carried out at a time point at which the tumor mass was small (150 to 200 mm$^3$), and the same virus as described above was intratumorally administered to the mice once.

In order to analyze whether or not the intravenously administered lung cancer cells would grow in the lung, and whether or not the intravenously administered rMV-EGFP-SLAMblind would be accumulated in the tumor, NCI-H441/CMV-Luc cells ($1\times10^5$ cells in 100 µl) were intravenously administered to the mice. Thereafter, 200 µl of D-luciferin (10 mg/ml, Gold Biotechnology, Inc.) was subcutaneously administered to the mice. To monitor the growth of the tumor, luminescence was measured using Xenogen IVIS Imaging System 100 (Xenogen/Caliper Life Sciences). As imaging parameters, exposure was set at 1 minute and binning was set at 8, and the measurement was carried out in the visual field of 15 cm. At a time point at which a tumor mass has grown to a sufficient size after transplantation of the lung cancer cells, $10^6$ TCID$_{50}$ of rMV-EGFP-SLAMblind (100 µl) was intravenously administered to the mice. Moreover, also at time points of 14, 41 and 48 days after the initial administration of rMV-EGFP-SLAMblind, 250 µl of rMV-EGFP-SLAMblind was intravenously administered to the mice. Thereafter, each mouse was euthanized, and its lung was then observed under a fluorescence microscope.

7-2. Colon Cancer Cell Lines

DLD1 cells or HT29 cells (cell count: $5\times10^6$) were suspended in 50% Matrigel (BD Biosciences), and the obtained suspension was then subcutaneously injected into the flank of 6-week-old female SCID mice. Thereafter, a change in the tumor was observed, and the size thereof was measured every 2 or 3 days. At a time point at which a tumor mass has reached 150 mm$^3$ after completion of the transplantation, $10^6$ TCID$_{50}$ of rMV-EGFP-SLAMblind was intratumorally administered to the mice every week three times. The volume of the tumor was calculated by the formula: (width×width×length)/2.

7-3. Breast Cancer Cell Lines

With regard to triple-negative breast cancer cell lines, HCC70 cells or MB-468 cells (cell count: $5\times10^6$) were suspended in 50% Matrigel (BD Biosciences), and the obtained suspension was then subcutaneously injected into 6-week-old female SCID mice. Thereafter, a change in the tumor was observed, and the size thereof was measured every 2 or 3 days. At a time point at which a tumor mass has grown to a sufficient size after transplantation of the triple-negative breast cancer cells, $10^6$ TCID$_{50}$ of rMV-EGFP-SLAMblind or rMV-V(-)-EGFP-SLAMblind was intratumorally administered to the mice every week in a total of three times. The volume of the tumor was calculated by the formula: (width×width×length)/2.

Human breast cancer cells MCF7 were transplanted into mice, and the tumor regression effects of intravenously administered rMV-EGFP-SLAMblind on the growing breast cancer tumor cells were then examined. In this case, MCF7 cells (cell count: $1.5\times10^6$) were suspended in 50% Matrigel (BD Biosciences), and the obtained suspension was then subcutaneously injected into 6-week-old female SCID mice. At a time point at which a tumor mass had grown to a sufficient size after transplantation of the MCF7 cells, $10^6$ TCID$_{50}$ of rMV-EGFP-SLAMblind was intravenously administered to the mice. Further, also at a time point of 4 days after the initial administration, rMV-EGFP-SLAMblind was administered to the mice. The volume of the tumor was calculated by the formula: (width×width×length)/2.

7-4. Dog Breast Cancer Cells

CF33 cells (cell count: $5\times10^6$) were suspended in 50% Matrigel (BD Biosciences), and the obtained suspension was then subcutaneously injected into 6-week-old female SCID mice. Thereafter, a change in the tumor was observed, and at a time point at which a tumor mass has grown to a sufficient size, $10^6$ TCID$_{50}$ of rMV-EGFP-SLAMblind rMV-V(-)-EGFP-SLAMblind was intratumorally administered to the mice. The volume of the tumor was calculated by the formula: (width×width×length)/2.

7-5. Pancreatic Cancer Cells

KLM1 cells (cell count: $1\times10^6$) were suspended in 50% Matrigel (BD Biosciences), and the obtained suspension was then transplanted subcutaneously into the right flank of C.B-17/Icr-SCID mice. Nineteen days after the transplantation, the mice were divided into two groups (7 mice in each group), and rMV-EGFP-SLAMblind was then inoculated in an amount of $1\times10^6$ into the tumor. Thereafter, 8, 14 and 37 days after the inoculation, the virus was inoculated into the tumor in the same manner as that for the first inoculation. After completion of the inoculation, the volume of the tumor was measured every two or three days. The volume of the tumor was calculated by the formula: (width×width×length)/2.

[Example 1] Effects on Human Lung Cancers

Infectivity of rMV-SLAMblind to PVRL4-Positive Lung Cancer Cells

The expression level of PVRL4 in lung cancer cell lines including 14 types of non-small cell lung cancers and 8 types of small cell lung cancers was examined by flow cytometry. As a result, it was found that PVRL4 was expressed in 8 types of non-small cell lung cancer cell lines (ABC1, NCI-H441, NCI-H2170, NCI-H358, Calu-3, PC14, A431 and NCI-H1666) and one type of small cell lung cancer cell line (SBC-2) (FIGS. 1 and 2).

Moreover, in order to analyze whether or not other molecules functioning as measles virus receptors would be expressed in these cell lines, the expression levels of CD46 and SLAM were examined. As a result, it was found that CD46 was expressed in all of the cell lines, but SLAM was not expressed (FIG. 1). When the cells were infected with rMV-EGFP-SLAMblind at moi=0.1 or 2, all of the cells, in which PVRL4 were expressed, emitted fluorescence in the case of infection at both moi, and formed syncytia (FIG. 3).

In Vitro Killing Effects of rMV-SLAMblind on Luna Cancer Cells

In order to examine whether or not PVRL4-expressing lung cancer cell lines would be killed as a result of infection with rMV-SLAMblind, the viability of 8 types of non-small cell lung cancer cell lines (ABC1, NCI-H441, NCI-H2170, Callu-3, NCI-H358, PC14, A431, and NCI-H1666) was analyzed after the infection of the cells with rMV-EGFP-SLAMblind. The viability of ABC1, NCI-H441, NCI-H2170, NCI-H358, Calu-3 and NCI-H1666 was reduced to 40% or less at a time point of 7 dpi (FIG. 4). On the other hand, ABC1, NCI-H441, H2170, H358 and Calu-3 had expressed a relatively high level of PVRL4 (FIG. 1), and these 5 types of cell lines were all killed as a result of infection with rMV-SLAMblind. The expression level of PVRL4 in NCI-H1666, PC14 and A431 had been low. Until a time point of 7 dpi, a clear decrease in the viability of PC14 and A431 was not observed after infection with rMV-SLAMblind, but the viability of NCI-H1666 was decreased.

The killing effects of rMV-EGFP-SLAMblind were almost correlated with the expression level of PVRL4.

In Vivo Antitumor Effects of rMV-SLAMblind on Lung Cancer-Derived Tumor

Subsequently, the in vivo antitumor effects of rMV-SLAMblind were examined using a mouse xenograft model. NCI-H441 was selected as a lung cancer cell line to be used in transplantation. NCI-H441 is a cell line, in which PVRL4 is highly expressed and a decrease in the viability of which is clearly found as a result of infection with rMV-EGFP-SLAMblind, and also, it has been reported that NCI-H441 can be transplanted into SCID mice. After the transplanted tumor had grown and had become a sufficient mass, $1 \times 10^6$ TCID$_{50}$ of rMV-EGFP-SLAMblind was intratumorally administered to the mouse three times. As a result, the growth of the tumor was significantly suppressed, when compared with the case of a control mouse (FIG. 5A). When virotherapy was carried out on a smaller tumor, the tumor was apparently reduced by a single administration (FIG. 5B). These results demonstrate that rMV-SLAMblind exhibits antitumor effects in vivo.

Intravenous Administration

Furthermore, in order to examine whether or not rMV-SLAMblind can target tumor that had grown in the lung, NCI-H441/CMV-Luc retaining a luciferase gene was intravenously administered to the mouse, so as to carry out xeno-transplantation. The growth of the tumor was monitored by measuring luminescence using Xenogen IVIS Imaging System 100. After a growing tumor had been clearly visualized, rMV-EGFP-SLAMblind was intravenously administered to the mouse over several administrations. As a result of the analysis using IVIS, luminescence derived from the transplanted tumor cells and fluorescence derived from viruses replicated in the tumor cells were observed in a single area. Since the resolution of fluorescence observed with IVIS was not so high, the mouse was euthanized and the lung thereof was then observed under a fluorescence microscope. As a result of the observation of the lung under the fluorescence microscope, it became clear that a plurality of growing tumors were present in the lung. The number of tumors was within the range of 16 to 36 in a single lung. Moreover, the fluorescence signals from rMV-SLAMblind-EGFP were dependent on administration of rMV-SLAMblind-EGFP, and were detected in many of these tumors (FIGS. 5C and 5D). These results demonstrate that a plurality of tumors existing in different sites in the lung can be infected with rMV-SLAMblind by the intravenous administration thereof.

Taking into consideration the after-mentioned results of the intravenous administration of rMV-SLAMblind to breast cancer, it is suggested that rMV-SLAMblind should be able to exhibit effective therapeutic effects also on metastatic cancers (i.e., cancers that have adhered to sites other than the primary lesion through the vein or the like, and have then grown therein), etc.

[Example 2] Effects on Human Colon Cancers

Infectivity of rMV-SLAMblind to PVRL4-Positive Colon Cancer Cells

The expression level of PVRL4 in colon cancer cell lines was examined by flow cytometry. The expression of PVRL4 was observed in CaCo-2, DLD1, HT29, LS174, RKO, SW48, SW480 and SW948, among 10 types of colon cancer cell lines (FIG. 6A). On the other hand, with regard to the expression of CD46 and SLAM, SLAM was not expressed in all of the cell lines, whereas CD46 was expressed in all of the cell lines (FIG. 6A).

Moreover, when the expression of the mRNA of PVRL4 was examined by RT-PCR, the expression of PVRL4 mRNA was matched with the expression of PVRL4 on the cell surface (FIGS. 6A and 6B).

In Vitro Killing Effects of rMV-SLAMblind on Colon Cancer Cells

Various types of cell lines were infected with rMV-EGFP-SLAMblind at moi=2, and the cells were then observed under a fluorescence microscope at a time point of 3 dpi. As a result, EGFP-derived fluorescence was observed over the entire cells, only in the case of PVRL4-positive cells (FIG. 7A). Subsequently, in order to examine the killing ability of rMV-EGFP-SLAMblind on PVRL4, a WST assay was carried out. When PVRL4-positive cells were infected with rMV-EGFP-SLAMblind and were then incubated, the viability of the cells was reduced over time (FIG. 7B). In contrast, the viability of PVRL4-negative cells was not changed even in the presence of rMV-EGFP-SLAMblind (FIG. 7C).

In Vivo Antitumor Effects of rMV-SLAMblind on Colon Cancer Cell-Derived Tumors

Subsequently, DLD1 cells and HT29 cells were each transplanted into mice, and then, the effects of rMV-EGFP-SLAMblind on growing tumors were analyzed. As shown in FIG. 8A, it was confirmed that when rMV-EGFP-SLAMblind was administered to the mice every week, the tumor generated as a result of transplantation of the DLD1 cells was reduced by approximately 55%, when compared with the tumor generated as a result of transplantation of the DLD1 cells, to which a medium was administered (control tumor). Likewise, it was also confirmed the tumor generated as a result of transplantation of the HT29 cells was reduced by approximately 60%, when compared with a control tumor (FIG. 8B). Twenty days after the initial infection, individual mice were euthanized, and the weight of each tumor was then measured. The weight of the tumor in a rMV-EGFP-SLAMblind administration group was apparently lower than the weight of the tumor in a control group, to which a medium had been administered (FIG. 8C).

Thereafter, one week after the final infection with rMV-EGFP-SLAMblind, whether or not the rMV-EGFP-SLAMblind remained in the tumor was examined. Based on the uptake status of 7-AAD, living cells that were not stained with 7-AAD were selected using a flow cytometer. Then, the ratio of EGFP-positive cells (cells in which rMV-EGFP-SLAMblind remained) was examined. As a result, 1% to 6% (average: 2.9%) of DLD1 cell-derived tumor cells were found to be EGFP-positive, and 0.2% to 2% (average: 1.0%) of HT29 cell-derived tumor cells were found to be EGFP-positive (FIG. 8D). In contrast, rMV-EGFP-SLAMblind-non-administered tumor cells, which had been treated with a medium, were found to be EGFP-negative (FIG. 8D).

From the aforementioned results, it could be confirmed that rMV-SLAMblind exhibits good antitumor effects on colon cancer cell-derived tumor. In particular, the DLD1 cell line is derived from refractory cancers showing resistance to an anti-EGFR antibody as a conventional molecular targeted drug. However, rMV-SLAMblind exhibited effective antitumor effects even on tumors into which such a DLD1 cell line had been transplanted, and thus, rMV-SLAMblind is considered to be also effective for the treatment of refractory cancers.

[Example 3] Effects on Human Triple-Negative Breast Cancers

Infectivity of rMV-SLAMblind to Triple-Negative Breast Cancer Cells

The expression level of PVRL4 in triple-negative breast cancer cell lines was examined by flow cytometry. As a result, it was found that PVRL4 was expressed in 9 types of cells (HCC1599, HCC1187, HCC70, MDA-MB-468, HCC38, HCC1143, HCC1937, BT-20 and HCC1806) (FIG. 9A). Then, the PVRL4-expressing HCC38 cells were injected with rMV-EGFP-SLAMblind at moi=2. As a result, the cells emitted fluorescence and formed syncytia (FIG. 9B).

In Vitro Killing Effects of rMV-SLAMblind and rMV-V(−)-SLAMblind on Triple Negative Cancer Cells In order to examine whether or not PVRL4-expressing cell lines would be killed as a result of infection with rMV-EGFP-SLAMblind or rMV-V(−)-EGFP-SLAMblind, the viability of a PVRL4-positive triple-negative breast cancer cell line, HCC70, was analyzed. As a result, the viability of the cells was reduced to approximately 10% to 20% at a time point of 7 dpi (FIG. 10A). On the other hand, rMV-EGFP-SLAMblind and rMV-V(−)-EGFP-SLAMblind did not exhibit killing effects on B95a cells (derived from marmoset B lymphocyte blasts) used as control cells (FIG. 10B).

In Vivo Antitumor Effects of rMV-SLAMblind and rMV-V(−)-SLAMblind on Triple Negative Cancer Cell-Derived Tumors Subsequently, the antitumor effects of rMV-EGFP-SLAMblind or rMV-V(−)-EGFP-SLAMblind on a triple-negative breast cancer cell-derived tumor was analyzed using SCID mouse xenograft models. HCC70 cells were selected as a triple-negative breast cancer cell line to be used in transplantation. After the transplanted tumor had started to grow, $1\times10^6$ $TCID_{50}$ of rMV-EGFP-SLAMblind or rMV-V(−)-EGFP-SLAMblind was intratumorally administered to the mice at time points indicated with the arrows in FIG. 11. As a result, in both cases of rMV-EGFP-SLAMblind and rMV-V(−)-EGFP-SLAMblind administrations, the growth of the tumor was apparently suppressed in comparison to control mice, (FIG. 11).

[Example 4] Human Breast Cancer-Derived Tumor Regression Effects of rMV-SLAMblind by Intravenous Administration Subsequently, whether or not intravenously administered rMV-EGFP-SLAMblind would exhibit tumor regression effects on a breast cancer (non-triple-negative breast cancer)-derived tumor was analyzed. MCF7 was selected as a breast cancer cell line to be used in transplantation. With regard to MCF7-derived tumor, it had been confirmed that the tumor was reduced by intratumoral administration of rMV-EGFP-SLAMblind (JP Patent Publication (Kokai) No. 2013-216609 A). After completion of the transplantation, when the tumor mass reached approximately 100 mm³, and at a time point of the 4th day after the initial administration, $1\times10^6$ $TCID_{50}$ of rMV-EGFP-SLAMblind was administered into the caudal vein of the mice, and the volume of the tumor was then measured over time (FIG. 12). As a result, the growth of the tumor was apparently suppressed in a rMV-EGFP-SLAMblind administration group, in comparison to a rMV-EGFP-SLAMblind non-administration group (control group) (FIG. 12).

From these results, it was found that rMV-SLAMblind has the effect of significantly suppressing tumor growth, even when it is intravenously administered.

[Example 5] Effects on Human Breast Cancer-Derived Cancer Stem Cells

Expression Level of PVRL4 on Surface of Cancer Stem Cells

In order to examine the expression status of PVRL4 on the surface of cancer stem cells (cancer stem like cells; CSC), a human cancer cell line HCC1187 was stained with antibodies reacting against CSC markers (CD44, CD24 and EpCAM), and thereafter, the expression of PVRL4 was analyzed by flow cytometry. The abundance percentage of CSC in the HCC1187 cell population was 4.9%. The percentage of cells expressing PVRL4 was 99.5% based on the HCC1187 cells as a whole, and was 99.7% based on the CSC cell fraction.

From these results, it was found that PVRL4 is expressed in cancer stem cells at the same level as in non-cancer stem cells.

Infectivity of rMV-SLAMblind to Breast Cancer-Derived Cancer Stem Cells

In order to examine the infectivity of the rMV-SLAMblind of the present invention to cancer stem cells, the human cancer cell line HCC1187 was stained with antibodies reacting against CSC markers (CD44, CD24 and EpCAM), and the stained cells were then sorted into cancer stem cells (CSCs) and non-cancer stem cells (NCSCs). The thus fractionated cells were infected with rMV-SLAMblind at moi=1, and were then observed under a fluorescence microscope (FIG. 13A). As a result, it was found that rMV-SLAMblind has infectivity to cancer stem cells.

In Vitro Killing Effects of rMV-SLAMblind on Cancer Stem Cells

Cancer stem cells sorted from the HCC1187 cell population were infected with rMV-EGFP-SLAMblind at moi=1, and the viability of the cells was then examined at time points of 1 dpi, 3 dpi, 5 dpi and 7 dpi. The viability of the cancer stem cells infected with rMV-SLAMblind was reduced, as in the case of non-cancer stem cells (FIG. 13B).

From the aforementioned results, it became clear that rMV-SLAMblind has infectivity also to cancer stem cells and has an ability to effectively kill the cancer stem cells.

[Example 6] Effects on Dog Breast Cancer

Infectivity of rMV-SLAMblind on Dog Breast Cancer Cells

A wild type MV, from which the rMV-SLAMblind was generated, is a virus causing infectivity to a human as a natural host. Thus, it has low infectivity to other animals, and even if dogs are experimentally infected with the MV, measles never occur in the dogs. On the other hand, in recent years, the number of dogs affected with breast cancer has increased, and thus, it has been desired to develop an effective method for treating dog breast cancer, as well as human breast cancer. Hence, the infectivity of rMV-SLAMblind to dog breast cancer cells was analyzed.

The expression level of PVRL4 in 9 types of dog breast cancer cell lines was examined by flow cytometry. As a result, it was found that PVRL4 was expressed in 4 types of cells (CF33, CTBp, CTBm and CHMm) (FIG. 14A). It is to be noted that CHMp and CHMm are cells derived from a single dog, and that CHMp is derived from a primary cancer whereas CHMm is derived from a metastatic cancer. When the two types of cells were compared with each other in terms of the expression level of PVRL4, the expression of PVRL4 was not observed in the primary cancer-derived CHMp, and the expression of PVRL4 was observed in the metastatic cancer-derived CHMm (FIG. 14A).

When the cell lines CF33, CTBp, CTBm and CHMm were infected with rMV-EGFP-SLAMblind at moi=2, these PVRL4-expressing cells emitted fluorescence and formed syncytia (FIG. 14B).

Moreover, two specimens of breast cancer cells (primary culture cell lines) collected from dogs with breast cancer were also examined in terms of the expression of PVRL4. As a result, PVRL4 was expressed in both of the two specimens, and the cells were infected with rMV-EGFP-SLAMblind at moi=0.1 and formed syncytia (FIG. 14C).

Subsequently, in order to compare the expression level of PVRL4 in a primary cancer-derived breast cancer cell line with that in a metastatic cancer-derived breast cancer cell line, the expression level of PVRL4 in CHMp cells (derived from a primary cancer) and that in CHMm cells (derived from a metastatic cancer) were examined by flow cytometry. As described above, the expression of PVRL4 could be confirmed in the metastatic cancer-derived CHMm, but it could not be confirmed in the primary cancer-derived CHMp (FIG. 15A). Furthermore, the infectivity of rMV-SLAMblind to the CHMp cells and the CHMm cells was also analyzed. As a result, the infectivity of rMV-SLAMblind to the primary cancer-derived CHMp cells was not found at all. In contrast, the metastatic cancer-derived CHMm cells were highly infected with rMV-SLAMblind, and the virus has grown, so that cell degeneration (fusion giant cells) was caused by killing the cells with the virus (FIG. 15B).

From the aforementioned results, it is considered that PVRL4 is expressed at a higher level in metastatic cancers than in primary cancers, and thus that the infectivity of rMV-SLAMblind to metastatic cancer cells is more significantly induced.

In Vitro Killing Effects of rMV-SLAMblind on Dog Breast Cancer Cells

In order to examine whether or not PVRL4-positive dog breast cancer cells would be killed by infection with rMV-EGFP-SLAMblind, the viability of 4 types of PVRL4-positive dog breast cancer cell lines (CF33, CTBp, CTBm and CHMm) was analyzed. As a result, it was found that the viability of CTBm was approximately 80% at a time point of 7 dpi, but the viability of CF33, CTBm and CHMm was reduced to approximately 40%. Accordingly, it was found that rMV-EGFP-SLAMblind exhibits effective killing effects also on dog breast cancer cells (FIG. 16). In particular, the infection of the primary cancer-derived CHMp with rMV-SLAMblind could not be confirmed and the killing effects of rMV-SLAMblind were hardly observed, whereas rMV-SLAMblind exhibited good killing effects on metastatic cancer-derived CHMm (FIG. 16).

In Vivo Antitumor Effects of rMV-SLAMblind on Dog Breast Cancer Cell-Derived Tumors Subsequently, the antitumor effects of rMV-SLAMblind on a dog breast cancer cell-derived tumor were analyzed using SCID mouse xenograft models. CF33 was selected as a dog breast cancer cell line to be used in transplantation. After completion of the transplantation, the time point at which the tumor mass reached a sufficient size was defined as 0 dpi, and $1 \times 10^6$ $TCID_{50}$ of rMV-EGFP-SLAMblind was intratumorally administered to the mice at time points of 0 dpi and 8 dpi. As a result, when rMV-EGFP-SLAMblind was administered to the mice, the growth of the tumor was clearly suppressed in comparison to a control (FIG. 17A).

Further, 50 days after the initial infection, the mice were euthanized, and the weight of the tumor was then measured. As a result, it was found that the weight of the tumor in a rMV-EGFP-SLAMblind administration group was apparently lighter than that in a control group, to which a medium had been administered (FIG. 17B).

[Example 7] Effects on Human Pancreatic Cancers

Expression Level of PVRL4 on Surface of Human Pancreatic Cancer Cells

The expression of PVRL4 in human-derived pancreatic cancer cell lines KLM1, PK1 and Capan-2 was analyzed by flow cytometry. As a result, the expression of PVRL4 could be confirmed in all of these three types of cells (FIG. 18A). In addition, the expression of SLAM and CD46 was examined in these three types of cells. As a result, the expression of SLAM was not observed in all of these cells, but the expression of CD46 was confirmed in all of these cells (FIG. 18B). It is to be noted that both SLAM and CD46 were expressed in CoBL cells and thus, CoBL demonstrated results as a positive control (FIG. 18B).

The KLM1 cell line and the PK1 cell line were derived from a single patient. KLM1 was obtained by performing xenotransplantation of the PK1 cells into a mouse, and then collecting the cells from the metastatic cancer portion. It was found that the KLM1 cells are a cancer cell line having higher metastatic ability and tumorigenicity than the PK1 cells, and that the expression level of PVRL4 is higher in the KLM1 cells than in the PK1 cells (FIG. 18A).

Infectivity and Killing Effects of rMV-SLAMblind on Human Pancreatic Cancer Cells The cell lines KLM1, PK1 and Capan-2 were infected with rMV-EGFP-SLAMblind at moi=1. As a result, two days after the infection, viral infection was observed in all of the cells (FIG. 19A).

Moreover, the viability of the KLM1 cells, PK1 cells and Capan-2 cells was analyzed, after the cells had been infected with rMV-EGFP-SLAMblind at moi=1. As a result, a decrease in the viability was observed in all of the cell lines (the white circles in FIG. 19B). That is to say, it was found that rMV-SLAMblind also exhibits good killing effects on pancreatic cancer cells.

Herein, referring to FIG. 19B, a decrease in the viability of the KLM1 cells was more significant than that of the PK1 cells. As a result of an analysis of using clinical samples from pancreatic cancer patients, it had been reported that PVRL4 is strongly expressed in a large tumor with a size of 4 cm or greater (Izumi et al., Surg Today, 2015 April, 45(4): 487-94.). Accordingly, it can be expected that the rMV-SLAMblind therapy will exhibit therapeutic effects on highly malignant pancreatic cancers such as metastatic cancers.

In Vivo Antitumor Effects of rMV-SLAMblind on Human Pancreatic Cancer Cell-Derived Tumors The antitumor effects of rMV-SLAMblind on a human pancreatic cancer cell-derived tumor were analyzed using SCID mouse xenograft models. KLM1 cells having high metastatic ability were selected as a human pancreatic cancer cell line to be used in transplantation.

$1 \times 10^6$ of KLM1 cells were subcutaneously transplanted into the right flank of C.B-17/Icr-SCID mice. On the 19th day after the transplantation, the mice were divided into two groups (7 mice in each group), and rMV-SLAMblind-EGFP was then inoculated at a density of $1 \times 10^6$ into the tumor of each mouse. For a control group, an equal amount of HBSS medium was inoculated into the tumor. On the 8th, 14th and 37th day after the inoculation, viral inoculation was carried out again in the same manner as that for the 1st inoculation. After completion of the inoculation, the size of the tumor was measured every two or three days (FIG. 20A). As a result, it was found that, when rMV-EGFP-SLAMblind was administered, the growth of the tumor was clearly suppressed in comparison to a control, into which a medium had been inoculated (FIG. 20A).

On the 70th day after the first viral inoculation, the mice in the medium inoculation group (mock) were euthanized, the tumor was then excised from each mouse, and the weight thereof was then measured. The mice in the rMV-SLAMblind inoculation group (dSLAM) were euthanized on the 84th day after the first viral inoculation (i.e., on the 47th day after the final inoculation), and the weight of the tumor was then measured (FIG. 20B). A significant difference was found between the size of the tumor in the rMV-SLAMblind inoculation group and that in the medium inoculation group. Thus, it was demonstrated that rMV-SLAMblind suppresses the growth of the KLM1 cells in the xenograft models.

Moreover, a frozen section was produced from the tumor excised from the rMV-SLAMblind administration mouse, and it was then observed under a fluorescence microscope. As a result, virus-encoded EGFP derived fluorescence was observed (FIG. 20C). Thereafter, viral isolation was attempted from the tumor mass of the rMV-SLAMblind administration mouse on the 47th day after the inoculation, and as a result, the virus was isolated. A mutation site introduced into the H gene of rMV-SLAMblind was analyzed by direct sequencing. As a result, a mutation for introducing SLAMblind was conserved.

INDUSTRIAL APPLICABILITY

The present invention provides a medicament or a pharmaceutical composition comprising an oncolytic recombinant measles virus, and in particular, the present medicament or pharmaceutical composition is able to effectively cause regression of difficult-to-treat cancers or metastatic cancer cells. Therefore, the present invention provides a technique extremely useful in the field of treating cancer.

---

The invention claimed is:

1. A pharmaceutical composition for use in the treatment of cancer, comprising:
rMV-V(−)-SLAM-blind.

2. The pharmaceutical composition according to claim 1, wherein the composition wounds and kills cancer stem cells.

3. The pharmaceutical composition according to claim 1, wherein the cancer is refractory cancer.

4. The pharmaceutical composition according to claim 1, wherein the cancer is metastatic cancer.

5. The pharmaceutical composition according to claim 1, wherein the cancer is triple-negative breast cancer, pancreatic cancer, lung cancer, or colon cancer.

6. The pharmaceutical composition according to claim 1, wherein the composition is configured for intravenous administration of the rMV-V(−)-SLAM-blind.

7. The pharmaceutical composition according to claim 1, wherein a therapeutic target of the composition is a dog.

8. A method of treating cancer, comprising:
administering rMV-V(−)-SLAM-blind to a subject in need of treatment of cancer.

9. The method according to claim 8, wherein the cancer is refractory cancer.

10. The method according to claim 8, wherein the cancer is metastatic cancer.

11. The method according to claim 8, wherein the cancer is triple-negative breast cancer, pancreatic cancer, lung cancer, or colon cancer.

12. The method according to claim 8, wherein the rMV-V(−)-SLAM-blind is administered intravenously.

13. The method according to claim 8, wherein the patient is a dog.

14. The method according to claim 8, wherein the patient is a human.

* * * * *

SEQUENCE LISTING

```
<160> NUMBER OF SEQ ID NOS: 13

<210> SEQ ID NO 1
<211> LENGTH: 15894
<212> TYPE: DNA
<213> ORGANISM: Measles virus
<220> FEATURE:
<221> NAME/KEY: CDS
<222> LOCATION: (108)..(1685)
<220> FEATURE:
<221> NAME/KEY: CDS
<222> LOCATION: (1807)..(3330)
<220> FEATURE:
<221> NAME/KEY: CDS
<222> LOCATION: (3438)..(4445)
<220> FEATURE:
<221> NAME/KEY: CDS
<222> LOCATION: (5458)..(7110)
<220> FEATURE:
<221> NAME/KEY: CDS
<222> LOCATION: (7271)..(9124)
<220> FEATURE:
<221> NAME/KEY: CDS
<222> LOCATION: (9234)..(15785)

<400> SEQUENCE: 1
accaaacaaa gttgggtaag gatagatcaa tcaatgatca tattctagta cacttaggat        60
tcaagatcct attatcaggg acaagagcag gattagggat atccgag atg gcc aca        116
                                                    Met Ala Thr
                                                      1 ctt ttg agg agc tta gca ttg ttc aaa aga aac aag gac aaa cca ccc        164
Leu Leu Arg Ser Leu Ala Leu Phe Lys Arg Asn Lys Asp Lys Pro Pro
      5                  10                  15 att aca tca gga tcc ggt gga gcc atc aga gga atc aaa cac att att        212
Ile Thr Ser Gly Ser Gly Gly Ala Ile Arg Gly Ile Lys His Ile Ile
 20                  25                  30                  35 ata gta cca att cct gga gat tcc tca att acc act cga tcc agg cta        260
Ile Val Pro Ile Pro Gly Asp Ser Ser Ile Thr Thr Arg Ser Arg Leu
                 40                  45                  50 ctg gac cgg ttg gtc agg tta att gga aac ccg gat gtg agc ggg ccc        308
Leu Asp Arg Leu Val Arg Leu Ile Gly Asn Pro Asp Val Ser Gly Pro
             55                  60                  65 aaa cta aca ggg gca ctc ata ggt ata tta tcc tta ttt gtg gag tct        356
Lys Leu Thr Gly Ala Leu Ile Gly Ile Leu Ser Leu Phe Val Glu Ser
```

```
                70                  75                  80
cca ggt caa ttg att cag agg atc acc gat gac cct gac gtt agc atc     404
Pro Gly Gln Leu Ile Gln Arg Ile Thr Asp Asp Pro Asp Val Ser Ile
 85                  90                  95 agg ctg tta gag gtt gtt cag agt gac cag tca caa tct ggc ctt acc     452
Arg Leu Leu Glu Val Val Gln Ser Asp Gln Ser Gln Ser Gly Leu Thr
100                 105                 110                 115 ttc gca tca aga ggt acc aac atg gag gat gag gcg gac caa tac ttt     500
Phe Ala Ser Arg Gly Thr Asn Met Glu Asp Glu Ala Asp Gln Tyr Phe
                120                 125                 130 tca cat gat gat cca agc aat agt gat caa tcc agg tcc gga tgg ttc     548
Ser His Asp Asp Pro Ser Asn Ser Asp Gln Ser Arg Ser Gly Trp Phe
            135                 140                 145 gag aac aag gaa atc tca gat att gaa gtg caa gac cct gag gga ttc     596
Glu Asn Lys Glu Ile Ser Asp Ile Glu Val Gln Asp Pro Glu Gly Phe
        150                 155                 160 aac atg att ctg ggt acc att cta gcc cag atc tgg gtc ttg ctc gca     644
Asn Met Ile Leu Gly Thr Ile Leu Ala Gln Ile Trp Val Leu Leu Ala
    165                 170                 175 aag gcg gtt acg gcc cca gac acg gca gct gat tcg gag cta aga agg     692
Lys Ala Val Thr Ala Pro Asp Thr Ala Ala Asp Ser Glu Leu Arg Arg
180                 185                 190                 195 tgg ata aag tac acc caa caa aga agg gta gtt ggt gaa ttt aga ttg     740
Trp Ile Lys Tyr Thr Gln Gln Arg Arg Val Val Gly Glu Phe Arg Leu
                200                 205                 210 gag aga aaa tgg ttg gat gtg gtg agg aac agg att gcc gag gac ctc     788
Glu Arg Lys Trp Leu Asp Val Val Arg Asn Arg Ile Ala Glu Asp Leu
            215                 220                 225 tct tta cgc cga ttc atg gtg gct cta atc ctg gat atc aag agg aca     836
Ser Leu Arg Arg Phe Met Val Ala Leu Ile Leu Asp Ile Lys Arg Thr
        230                 235                 240 ccc ggg aac aaa cct agg att gct gaa atg ata tgt gac att gat aca     884
Pro Gly Asn Lys Pro Arg Ile Ala Glu Met Ile Cys Asp Ile Asp Thr
    245                 250                 255 tat atc gta gag gca gga tta gcc agt ttt atc ctg act att aag ttt     932
Tyr Ile Val Glu Ala Gly Leu Ala Ser Phe Ile Leu Thr Ile Lys Phe
260                 265                 270                 275 ggg ata gaa act atg tat cct gct ctt gga ctg cat gaa ttt gct ggt     980
Gly Ile Glu Thr Met Tyr Pro Ala Leu Gly Leu His Glu Phe Ala Gly
                280                 285                 290 gag tta tcc aca ctt gag tcc ttg atg aat ctt tac cag caa atg gga    1028
Glu Leu Ser Thr Leu Glu Ser Leu Met Asn Leu Tyr Gln Gln Met Gly
            295                 300                 305 gaa act gca ccc tac atg gta atc cta gag aac tca att cag aac aag    1076
Glu Thr Ala Pro Tyr Met Val Ile Leu Glu Asn Ser Ile Gln Asn Lys
        310                 315                 320 ttc agt gca gga tca tac cct ctg ctc tgg agc tat gcc atg gga gta    1124
Phe Ser Ala Gly Ser Tyr Pro Leu Leu Trp Ser Tyr Ala Met Gly Val
    325                 330                 335 gga gtg gaa ctt gaa aac tcc atg gga ggt ttg aac ttt ggt cga tct    1172
Gly Val Glu Leu Glu Asn Ser Met Gly Gly Leu Asn Phe Gly Arg Ser
340                 345                 350                 355 tac ttt gat cca gca tat ttt aga tta ggg caa gag atg gtg agg agg    1220
Tyr Phe Asp Pro Ala Tyr Phe Arg Leu Gly Gln Glu Met Val Arg Arg
                360                 365                 370 tca gct gga aag gtc agt tcc aca ttg gca tcc gaa ctc ggt atc act    1268
Ser Ala Gly Lys Val Ser Ser Thr Leu Ala Ser Glu Leu Gly Ile Thr
            375                 380                 385 gcc gag gat gca agg ctt gtt tca gag att gca atg cat act act gag    1316
Ala Glu Asp Ala Arg Leu Val Ser Glu Ile Ala Met His Thr Thr Glu
```

-continued

```
                Ala Glu Asp Ala Arg Leu Val Ser Glu Ile Ala Met His Thr Thr Glu
                            390                 395                 400 gac agg atc agt aga gcg gtc gga ccc aga caa gcc caa gtg tca ttt         1364
Asp Arg Ile Ser Arg Ala Val Gly Pro Arg Gln Ala Gln Val Ser Phe
            405                 410                 415 cta cac ggt gat caa agt gag aat gag cta cca gga ttg ggg ggc aag         1412
Leu His Gly Asp Gln Ser Glu Asn Glu Leu Pro Gly Leu Gly Gly Lys
420                 425                 430                 435 gaa gat agg agg gtc aaa cag ggt cgg gga gaa gcc agg gag aac tac         1460
Glu Asp Arg Arg Val Lys Gln Gly Arg Gly Glu Ala Arg Glu Asn Tyr
                440                 445                 450 aga gaa acc ggt tcc agc aga gca agt gat gcg aga gct gcc cat cct         1508
Arg Glu Thr Gly Ser Ser Arg Ala Ser Asp Ala Arg Ala Ala His Pro
            455                 460                 465 cca acc agc atg ccc cta gac att gac act gca tcg gag tca ggc caa         1556
Pro Thr Ser Met Pro Leu Asp Ile Asp Thr Ala Ser Glu Ser Gly Gln
470                 475                 480 gat ccg cag gac agt caa agg tca gct gac gcc ctg ctc agg ctg caa         1604
Asp Pro Gln Asp Ser Gln Arg Ser Ala Asp Ala Leu Leu Arg Leu Gln
                485                 490                 495 gcc atg gca gga atc ttg gaa gaa caa ggc tca gac acg gac acc cct         1652
Ala Met Ala Gly Ile Leu Glu Glu Gln Gly Ser Asp Thr Asp Thr Pro
500                 505                 510                 515 agg gta tac aat gac aga gat ctt cta gac tag gtgcgagagg ccgaggacca       1705
Arg Val Tyr Asn Asp Arg Asp Leu Leu Asp
                520                 525 gaacaacatc cacctaccct ccatcattgt tataaaaaac ttaggaacca ggtccacaca        1765
gccgccagcc aaccaaccat ccactcccac gactggagcc a atg gca gaa gag cag       1821
                                            Met Ala Glu Glu Gln
                                                            530 gca cgc cat gtc aaa aac gga ctg gaa tgc atc cgg gct ctc aag gcc         1869
Ala Arg His Val Lys Asn Gly Leu Glu Cys Ile Arg Ala Leu Lys Ala
                535                 540                 545 gag ccc atc ggc tca ctg gcc gtc gag gaa gcc atg gca gca tgg tca         1917
Glu Pro Ile Gly Ser Leu Ala Val Glu Glu Ala Met Ala Ala Trp Ser
            550                 555                 560 gaa ata tca gac aac cca gga cag gac cga gcc acc tgc aag gaa gag         1965
Glu Ile Ser Asp Asn Pro Gly Gln Asp Arg Ala Thr Cys Lys Glu Glu
            565                 570                 575 gag gca ggc agt tcg ggt ctc agc aaa cca tgc ctc tca gca att gga         2013
Glu Ala Gly Ser Ser Gly Leu Ser Lys Pro Cys Leu Ser Ala Ile Gly
580                 585                 590 tca act gaa ggc ggt gca cct cgc atc cgc ggt cag gga tct gga gaa         2061
Ser Thr Glu Gly Gly Ala Pro Arg Ile Arg Gly Gln Gly Ser Gly Glu
595                 600                 605                 610 agc gat gac gac gct gaa act ttg gga atc ccc tca aga aat ctc cag         2109
Ser Asp Asp Asp Ala Glu Thr Leu Gly Ile Pro Ser Arg Asn Leu Gln
                615                 620                 625 gca tca agc act ggg tta cag tgt tat cat gtt tat gat cac agc ggt         2157
Ala Ser Ser Thr Gly Leu Gln Cys Tyr His Val Tyr Asp His Ser Gly
            630                 635                 640 gaa gcg gtt aag gga atc caa gat gct gac tct atc atg gtt caa tca         2205
Glu Ala Val Lys Gly Ile Gln Asp Ala Asp Ser Ile Met Val Gln Ser
            645                 650                 655 ggc ctt gat ggt gat agc acc ctc tca gga gga gac gat gaa tct gaa         2253
Gly Leu Asp Gly Asp Ser Thr Leu Ser Gly Gly Asp Asp Glu Ser Glu
660                 665                 670 aac agc gat gtg gat ctt ggc gaa cct gat acc gag gga tat gct atc         2301
Asn Ser Asp Val Asp Leu Gly Glu Pro Asp Thr Glu Gly Tyr Ala Ile
```

```
              675                 680                 685                 690
act gac cgg gga tct gct ccc atc tct atg ggg ttc agg gct tct gat          2349
Thr Asp Arg Gly Ser Ala Pro Ile Ser Met Gly Phe Arg Ala Ser Asp
                695                 700                 705 gtt gaa act gca gaa gga ggg gag atc cac gag ctc ctg aaa ctc caa          2397
Val Glu Thr Ala Glu Gly Gly Glu Ile His Glu Leu Leu Lys Leu Gln
        710                 715                 720 tcc aga ggc aac aac ttt ccg aag ctt ggg aaa act ctc aat gtt cct          2445
Ser Arg Gly Asn Asn Phe Pro Lys Leu Gly Lys Thr Leu Asn Val Pro
            725                 730                 735 ccg ccc ccg aac ccc agt agg gcc agc act tcc gag aca ccc att aaa          2493
Pro Pro Pro Asn Pro Ser Arg Ala Ser Thr Ser Glu Thr Pro Ile Lys
740                 745                 750 aag ggg aca gac gcg aga ttg gcc tca ttt gga acg gag atc gcg tct          2541
Lys Gly Thr Asp Ala Arg Leu Ala Ser Phe Gly Thr Glu Ile Ala Ser
755                 760                 765                 770 tta ttg aca ggt ggt gca acc caa tgt gct cga aag tca ccc tcg gaa          2589
Leu Leu Thr Gly Gly Ala Thr Gln Cys Ala Arg Lys Ser Pro Ser Glu
                775                 780                 785 cca tca ggg cca ggt gca cct gcg ggg aat gtc ccc gag tgt gtg agc          2637
Pro Ser Gly Pro Gly Ala Pro Ala Gly Asn Val Pro Glu Cys Val Ser
        790                 795                 800 aat gcc gca ctg ata cag gag tgg aca ccc gaa tct ggt acc aca atc          2685
Asn Ala Ala Leu Ile Gln Glu Trp Thr Pro Glu Ser Gly Thr Thr Ile
            805                 810                 815 tcc ccg aga tcc cag aat aat gaa gaa ggg gga gac tat tat gat gat          2733
Ser Pro Arg Ser Gln Asn Asn Glu Glu Gly Gly Asp Tyr Tyr Asp Asp
820                 825                 830 gag ctg ttc tcc gat gtc caa gac atc aaa aca gcc ttg gcc aaa ata          2781
Glu Leu Phe Ser Asp Val Gln Asp Ile Lys Thr Ala Leu Ala Lys Ile
835                 840                 845                 850 cac gag gat aat cag aag ata atc tcc aag cta gaa tca ttg ctg tta          2829
His Glu Asp Asn Gln Lys Ile Ile Ser Lys Leu Glu Ser Leu Leu Leu
                855                 860                 865 ttg aag gga gaa gtt gag tca atc aag aag cag atc aac agg caa aat          2877
Leu Lys Gly Glu Val Glu Ser Ile Lys Lys Gln Ile Asn Arg Gln Asn
        870                 875                 880 atc agc ata tcc acc ctg gaa gga cac ctc tca agc atc atg att gcc          2925
Ile Ser Ile Ser Thr Leu Glu Gly His Leu Ser Ser Ile Met Ile Ala
            885                 890                 895 att cct gga ctt ggg aag gat ccc aac gac ccc acc gca gat gtc gaa          2973
Ile Pro Gly Leu Gly Lys Asp Pro Asn Asp Pro Thr Ala Asp Val Glu
900                 905                 910 ctc aat ccc gac ctg aaa ccc atc ata ggc aga gat tca ggc cga gca          3021
Leu Asn Pro Asp Leu Lys Pro Ile Ile Gly Arg Asp Ser Gly Arg Ala
915                 920                 925                 930 ctg gcc gaa gtt ctc aag aag ccc gtt gcc agc cga caa ctc cag gga          3069
Leu Ala Glu Val Leu Lys Lys Pro Val Ala Ser Arg Gln Leu Gln Gly
                935                 940                 945 atg act aat gga cgg acc agt tcc aga gga cag ctg ctg aag gaa ttt          3117
Met Thr Asn Gly Arg Thr Ser Ser Arg Gly Gln Leu Leu Lys Glu Phe
        950                 955                 960 caa cta aag ccg atc ggg aaa aag gtg agc tca gcc gtc ggg ttt gtt          3165
Gln Leu Lys Pro Ile Gly Lys Lys Val Ser Ser Ala Val Gly Phe Val
            965                 970                 975 cct gac acc ggc cct gca tca cgc agt gta atc cgc tcc att ata aaa          3213
Pro Asp Thr Gly Pro Ala Ser Arg Ser Val Ile Arg Ser Ile Ile Lys
980                 985                 990 tcc agc cgg cta gag gag  gat cgg aag cgt tac  ctg atg act ctc            3258
```

```
Ser Ser Arg Leu Glu Glu  Asp Arg Lys Arg Tyr  Leu Met Thr Leu
995              1000                 1005 ctt  gat gat atc aaa gga  gcc aac gat ctt gcc  aag ttc cac cag     3303
Leu  Asp Asp Ile Lys Gly  Ala Asn Asp Leu Ala  Lys Phe His Gln
1010             1015                 1020 atg  ctg atg aag ata ata  atg aag tag ctacagctca acttacctgc        3350
Met  Leu Met Lys Ile Ile  Met Lys
1025             1030 caaccccatg ccagtcgacc taattagtac aacctaaatc cattataaaa aacttaggag  3410
caaagtgatt gcctcctaag ttccaca atg aca gag  atc tac gat ttc gac     3461
                           Met Thr Glu  Ile Tyr Asp Phe Asp
                                1035              1040 aag tcg gca tgg gac  atc aaa ggg tcg atc  gct ccg ata caa cct      3506
Lys Ser Ala Trp Asp  Ile Lys Gly Ser Ile  Ala Pro Ile Gln Pro
                1045                 1050                 1055 acc acc tac agt gat  ggc agg ctg gtg ccc  cag gtc aga gtc ata      3551
Thr Thr Tyr Ser Asp  Gly Arg Leu Val Pro  Gln Val Arg Val Ile
                1060                 1065                 1070 gat cct ggt cta ggt  gat agg aag gat gaa  tgc ttt atg tac atg      3596
Asp Pro Gly Leu Gly  Asp Arg Lys Asp Glu  Cys Phe Met Tyr Met
                1075                 1080                 1085 ttt ctg ctg ggg gtt  gtt gag gac agc gat  ccc cta ggg cct cca      3641
Phe Leu Leu Gly Val  Val Glu Asp Ser Asp  Pro Leu Gly Pro Pro
                1090                 1095                 1100 atc ggg cga gca ttc  ggg tcc ctg ccc tta  ggt gtt ggt aga ccc      3686
Ile Gly Arg Ala Phe  Gly Ser Leu Pro Leu  Gly Val Gly Arg Pro
                1105                 1110                 1115 aca gca aaa ccc gag  gaa ctc ctc aaa gag  gcc act gag ctt gac      3731
Thr Ala Lys Pro Glu  Glu Leu Leu Lys Glu  Ala Thr Glu Leu Asp
                1120                 1125                 1130 ata gtt gtt aga cgt  aca gca ggg ctc aat  gaa aaa ctg gtg ttc      3776
Ile Val Val Arg Arg  Thr Ala Gly Leu Asn  Glu Lys Leu Val Phe
                1135                 1140                 1145 tac aac aac acc cca  cta acc ctc ctc aca  cct tgg aga aag gtc      3821
Tyr Asn Asn Thr Pro  Leu Thr Leu Leu Thr  Pro Trp Arg Lys Val
                1150                 1155                 1160 cta aca aca ggg agt  gtc ttc aat gca aac  caa gtg tgc aat gcg      3866
Leu Thr Thr Gly Ser  Val Phe Asn Ala Asn  Gln Val Cys Asn Ala
                1165                 1170                 1175 gtt aat cta ata ccg  ctg gac acc ccg cag  agg ttc cgt gtt gtt      3911
Val Asn Leu Ile Pro  Leu Asp Thr Pro Gln  Arg Phe Arg Val Val
                1180                 1185                 1190 tat atg agc atc acc  cgt ctt tcg gat aac  ggg tat tac acc gtt      3956
Tyr Met Ser Ile Thr  Arg Leu Ser Asp Asn  Gly Tyr Tyr Thr Val
                1195                 1200                 1205 ccc aga aga atg ctg  gaa ttc aga tcg gtc  aat gca gtg gcc ttc      4001
Pro Arg Arg Met Leu  Glu Phe Arg Ser Val  Asn Ala Val Ala Phe
                1210                 1215                 1220 aac ctg cta gtg acc  ctt agg att gac aag  gca att ggc cct ggg      4046
Asn Leu Leu Val Thr  Leu Arg Ile Asp Lys  Ala Ile Gly Pro Gly
                1225                 1230                 1235 aag atc atc gac aat  gca gag caa ctt cct  gag gca aca ttt atg      4091
Lys Ile Ile Asp Asn  Ala Glu Gln Leu Pro  Glu Ala Thr Phe Met
                1240                 1245                 1250 gtc cac atc ggg aac  ttc agg aga aag aag  agt gaa gtc tac tct      4136
Val His Ile Gly Asn  Phe Arg Arg Lys Lys  Ser Glu Val Tyr Ser
                1255                 1260                 1265 gcc gat tat tgc aaa  atg aaa atc gaa aag  atg ggc ctg gtt ttt      4181
Ala Asp Tyr Cys Lys  Met Lys Ile Glu Lys  Met Gly Leu Val Phe
```

```
                    1270                    1275                    1280
    gca ctt ggt ggg ata ggg ggc acc agt ctt cac att aga agc aca          4226
    Ala Leu Gly Gly Ile Gly Gly Thr Ser Leu His Ile Arg Ser Thr
                        1285                    1290                    1295 ggc aaa atg agc aag act ctc cat gca caa ctc ggg ttc aag aag          4271
    Gly Lys Met Ser Lys Thr Leu His Ala Gln Leu Gly Phe Lys Lys
                    1300                    1305                    1310 acc tta tgt tac cca ctg atg gat atc aat gaa gac ctt aat cgg          4316
    Thr Leu Cys Tyr Pro Leu Met Asp Ile Asn Glu Asp Leu Asn Arg
                    1315                    1320                    1325 tta ctc tgg agg agc aga tgc aag ata gta aga atc cag gca gtt          4361
    Leu Leu Trp Arg Ser Arg Cys Lys Ile Val Arg Ile Gln Ala Val
                    1330                    1335                    1340 ttg cag cca tca gtt cct caa gaa ttc cgc att tac gac gac gtg          4406
    Leu Gln Pro Ser Val Pro Gln Glu Phe Arg Ile Tyr Asp Asp Val
                    1345                    1350                    1355 atc ata aat gat gac caa gga cta ttc aaa gtt ctg tag accgcagtgc       4455
    Ile Ile Asn Asp Asp Gln Gly Leu Phe Lys Val Leu
                    1360                    1365 ccagcaatac ccgaaaacga ccccctcat aatgacagcc agaaggcccg acaaaaaag      4515 cccctccag aagactccac ggaccaagcg agaggccagc cagcagccga cagcaagtgt     4575
ggacaccagg cggcccaagc acagaacagc cccgacacaa ggccaccacc agccatccca    4635
atctgcgtcc tcctcgtggg accccgagg accaatcctg aaggtcgctc cgaacacaga     4695
ccaccaaccg catccccaca gctcccggga aggaaccccc cagcaattgg aaggcccctc    4755
cccccctccc ccaacgcaag aaccccacaa ccgaaccgca caagcgaccg aggtgaccca    4815
accgcaggca tccgactcct tagacagatc ctctccccccc ggcatactaa acaaaactta   4875 gggcaagga acacacacac ccgacagaac ccagaccccg gccgcggca ccgcgccccc      4935 acccccgaa accagaggg agccccaac caaacccgcc ggcccccccg gtgcccacag       4995
gtaggcacac cgaccccga ccagaccag cacccagcca ccgacaatcc aagacggggg      5055 gccccccca aaaaaggcc cccaggggcc gacagccagc atcgcgagga agcacaccca      5115
ccccacacac gaccacggca accgaaccag agtccagacc accctgggcc accagctccc    5175
agactcggcc atcaccccgc aaaaaggaaa ggccacaacc cgcgcacccc agccccgatc    5235
cggcgggcag ccactcaacc cgaaccagca cccaagagcg atccttgggg accccaaa     5295 ccgcaaaaga catcagtatc ccacagcctc tccaagtccc ccggtctcct cctcttctcg    5355
aagggaccaa aagatcaatc caccacatcc gacgacactc aatttcccac ccccaaagga    5415
gacaccggga atcccagaat caagactcat ccagtgtcca tc atg ggt ctc aag       5469
                                                   Met Gly Leu Lys
                                                               1370 gtg aac gtc tct gcc ata ttc atg gca gta ctg tta act ctc caa          5514
    Val Asn Val Ser Ala Ile Phe Met Ala Val Leu Leu Thr Leu Gln
                    1375                    1380                    1385 aca ccc acc ggt caa atc cat tgg ggc aat ctc tct aag ata ggg          5559
    Thr Pro Thr Gly Gln Ile His Trp Gly Asn Leu Ser Lys Ile Gly
                    1390                    1395                    1400 gtg gta ggg ata gga agt gca agc tac aaa gtt atg act cgt tcc          5604
    Val Val Gly Ile Gly Ser Ala Ser Tyr Lys Val Met Thr Arg Ser
                    1405                    1410                    1415 agc cat caa tca ttg gtc ata aaa tta atg ccc aat ata act ctc          5649
    Ser His Gln Ser Leu Val Ile Lys Leu Met Pro Asn Ile Thr Leu
                    1420                    1425                    1430 ctc aat aac tgc acg agg gta gag atc gca gaa tac agg aga cta          5694
```

```
Leu Asn Asn Cys Thr Arg Val Glu Ile Ala Glu Tyr Arg Arg Leu
        1435                1440                1445 ctg aga aca gtt ttg gaa cca att aga gat gca ctt aat gca atg       5739
Leu Arg Thr Val Leu Glu Pro Ile Arg Asp Ala Leu Asn Ala Met
        1450                1455                1460 acc cag aat ata aga ccg gtt cag agt gta gct tca agt agg aga       5784
Thr Gln Asn Ile Arg Pro Val Gln Ser Val Ala Ser Ser Arg Arg
        1465                1470                1475 cac aag aga ttt gcg gga gta gtc ctg gca ggt gcg gcc cta ggc       5829
His Lys Arg Phe Ala Gly Val Val Leu Ala Gly Ala Ala Leu Gly
        1480                1485                1490 gtt gcc aca gct gct cag ata aca gcc ggc att gca ctt cat cag       5874
Val Ala Thr Ala Ala Gln Ile Thr Ala Gly Ile Ala Leu His Gln
        1495                1500                1505 tcc atg ctg aac tct caa gcc atc gac aat ctg aga gcg agc ctg       5919
Ser Met Leu Asn Ser Gln Ala Ile Asp Asn Leu Arg Ala Ser Leu
        1510                1515                1520 gaa act act aat cag gca att gag gca atc aga caa gca ggg cag       5964
Glu Thr Thr Asn Gln Ala Ile Glu Ala Ile Arg Gln Ala Gly Gln
        1525                1530                1535 gag atg ata ttg gct gct cag ggt gtc caa gac tac atc aat aat       6009
Glu Met Ile Leu Ala Ala Gln Gly Val Gln Asp Tyr Ile Asn Asn
        1540                1545                1550 gag ctg ata ccg tct atg aac caa cta tct tgt gat tta atc ggc       6054
Glu Leu Ile Pro Ser Met Asn Gln Leu Ser Cys Asp Leu Ile Gly
        1555                1560                1565 cag aag cta ggg ctc aaa ttg ctc aga tac tat aca gaa atc ctg       6099
Gln Lys Leu Gly Leu Lys Leu Leu Arg Tyr Tyr Thr Glu Ile Leu
        1570                1575                1580 tca tta ttt ggc ccc agc tta cgg gac ccc ata tct gcg gag ata       6144
Ser Leu Phe Gly Pro Ser Leu Arg Asp Pro Ile Ser Ala Glu Ile
        1585                1590                1595 tcc atc cag gct tcg agc tat gcg ctt gga gga gat atc aat aag       6189
Ser Ile Gln Ala Ser Ser Tyr Ala Leu Gly Gly Asp Ile Asn Lys
        1600                1605                1610 gtg tta gaa aag ctc gga tac agt gga ggt gat tta ctg ggc atc       6234
Val Leu Glu Lys Leu Gly Tyr Ser Gly Gly Asp Leu Leu Gly Ile
        1615                1620                1625 tta gag agc agg gga ata aag gcc cgg ata act cac gtc gac aca       6279
Leu Glu Ser Arg Gly Ile Lys Ala Arg Ile Thr His Val Asp Thr
        1630                1635                1640 gag tcc tac ttc att gta ctc agt ata gcc tat ccg acg ctg tcc       6324
Glu Ser Tyr Phe Ile Val Leu Ser Ile Ala Tyr Pro Thr Leu Ser
        1645                1650                1655 gag att aag ggg gtg att gtc cac cgg cta gag ggg gtc tcg tac       6369
Glu Ile Lys Gly Val Ile Val His Arg Leu Glu Gly Val Ser Tyr
        1660                1665                1670 aat ata ggc tct caa gag tgg tat acc act gtg ccc aag tat gtt       6414
Asn Ile Gly Ser Gln Glu Trp Tyr Thr Thr Val Pro Lys Tyr Val
        1675                1680                1685 gca acc caa ggg tac ctt atc tcg aat ttt gat gag tca tcg tgt       6459
Ala Thr Gln Gly Tyr Leu Ile Ser Asn Phe Asp Glu Ser Ser Cys
        1690                1695                1700 act ttc atg cca gag ggg act gtg tgc agc caa aat gcc ttg tac       6504
Thr Phe Met Pro Glu Gly Thr Val Cys Ser Gln Asn Ala Leu Tyr
        1705                1710                1715 ccg atg agt cct ctg ctc caa gaa tgc ctc cgg ggg tcc acc aag       6549
Pro Met Ser Pro Leu Leu Gln Glu Cys Leu Arg Gly Ser Thr Lys
        1720                1725                1730
```

```
tcc tgt gct cgt aca ctc gta tcc ggg tct ttt ggg aac cgg ttc    6594
Ser Cys Ala Arg Thr Leu Val Ser Gly Ser Phe Gly Asn Arg Phe
            1735            1740            1745 att tta tca caa ggg aac cta ata gcc aat tgt gca tca atc ctc    6639
Ile Leu Ser Gln Gly Asn Leu Ile Ala Asn Cys Ala Ser Ile Leu
            1750            1755            1760 tgc aag tgt tac aca aca gga acg atc att aat caa gac cct gac    6684
Cys Lys Cys Tyr Thr Thr Gly Thr Ile Ile Asn Gln Asp Pro Asp
            1765            1770            1775 aag atc cta aca tac att gct gcc gat cac tgc ccg gtg gtc gag    6729
Lys Ile Leu Thr Tyr Ile Ala Ala Asp His Cys Pro Val Val Glu
            1780            1785            1790 gtg aac ggc gtg acc atc caa gtc ggg agc agg agg tat ccg gac    6774
Val Asn Gly Val Thr Ile Gln Val Gly Ser Arg Arg Tyr Pro Asp
            1795            1800            1805 gcg gtg tac ctg cac aga att gac ctc ggt cct ccc ata tca ttg    6819
Ala Val Tyr Leu His Arg Ile Asp Leu Gly Pro Pro Ile Ser Leu
            1810            1815            1820 gag agg ttg gac gta ggg aca aat ctg ggg aat gca att gct aag    6864
Glu Arg Leu Asp Val Gly Thr Asn Leu Gly Asn Ala Ile Ala Lys
            1825            1830            1835 ttg gag gat gcc aag gaa ttg ttg gag tca tcg gac cag ata ttg    6909
Leu Glu Asp Ala Lys Glu Leu Leu Glu Ser Ser Asp Gln Ile Leu
            1840            1845            1850 agg agt atg aaa ggt tta tcg agc act agc ata gtt tac atc ctg    6954
Arg Ser Met Lys Gly Leu Ser Ser Thr Ser Ile Val Tyr Ile Leu
            1855            1860            1865 att gca gtg tgt ctt gga ggg ttg ata ggg atc ccc gct tta ata    6999
Ile Ala Val Cys Leu Gly Gly Leu Ile Gly Ile Pro Ala Leu Ile
            1870            1875            1880 tgt tgc tgc agg ggg cgc tgt aac aaa aag gga gaa caa gtt ggt    7044
Cys Cys Cys Arg Gly Arg Cys Asn Lys Lys Gly Glu Gln Val Gly
            1885            1890            1895 atg tca aga cca ggc cta aag cct gat ctt acg ggg aca tca aaa    7089
Met Ser Arg Pro Gly Leu Lys Pro Asp Leu Thr Gly Thr Ser Lys
            1900            1905            1910 tcc tat gta agg tcg ctc tga tcctctacaa ctcttgaaac acagatttcc   7140
Ser Tyr Val Arg Ser Leu
            1915 cacaagtctc ctcttcgtca tcaagcaacc accgcatcca gcatcaagcc cacttgaaat   7200 tgtctccggc ttccctctgg ccgaacgata tcggtagtta attaaaactt agggtgcaag   7260 atcatccaca atg tca cca caa cga gac cga ata aat gcc ttc tac aaa    7309
        Met Ser Pro Gln Arg Asp Arg Ile Asn Ala Phe Tyr Lys
            1920            1925            1930 gac aac cca cat cct aag gga agt agg ata gtt att aac aga gaa    7354
Asp Asn Pro His Pro Lys Gly Ser Arg Ile Val Ile Asn Arg Glu
            1935            1940            1945 cat ctt atg att gat aga cct tat gtt ttg ctg gct gtt cta ttc    7399
His Leu Met Ile Asp Arg Pro Tyr Val Leu Leu Ala Val Leu Phe
            1950            1955            1960 gtc atg ttt ctg agc ttg atc ggg ttg cta gcc atc gca ggc att    7444
Val Met Phe Leu Ser Leu Ile Gly Leu Leu Ala Ile Ala Gly Ile
            1965            1970            1975 aga ctc cat cgt gca gcc atc tac acc gca gag atc cat aag agc    7489
Arg Leu His Arg Ala Ala Ile Tyr Thr Ala Glu Ile His Lys Ser
            1980            1985            1990 ctc agc acc aat cta gat gta act aac tca atc gag cat cag gtc    7534
Leu Ser Thr Asn Leu Asp Val Thr Asn Ser Ile Glu His Gln Val
            1995            2000            2005
```

```
aag gac gtg ctg aca  cca ctc ttc aag atc  att ggt gat gaa gtg      7579
Lys Asp Val Leu Thr  Pro Leu Phe Lys Ile  Ile Gly Asp Glu Val
            2010              2015             2020 ggc ctg agg aca cct  cag aga ttc act gac  cta gtg aaa ttc atc      7624
Gly Leu Arg Thr Pro  Gln Arg Phe Thr Asp  Leu Val Lys Phe Ile
            2025              2030             2035 tct gac aaa att aaa  ttc ctt aat ccg gat  agg gag tac gac ttc      7669
Ser Asp Lys Ile Lys  Phe Leu Asn Pro Asp  Arg Glu Tyr Asp Phe
            2040              2045             2050 aga gat ctc act tgg  tgt atc aac ccg cca  gag aga atc aaa ttg      7714
Arg Asp Leu Thr Trp  Cys Ile Asn Pro Pro  Glu Arg Ile Lys Leu
            2055              2060             2065 gat tat gat caa tac  tgt gca gat gtg gct  gct gaa gaa ctc atg      7759
Asp Tyr Asp Gln Tyr  Cys Ala Asp Val Ala  Ala Glu Glu Leu Met
            2070              2075             2080 aat gca ttg gtg aac  tca act cta ctg gag  gcc agg gca acc aat      7804
Asn Ala Leu Val Asn  Ser Thr Leu Leu Glu  Ala Arg Ala Thr Asn
            2085              2090             2095 cag ttc cta gct gtc  tca aag gga aac tgc  tca ggg ccc act aca      7849
Gln Phe Leu Ala Val  Ser Lys Gly Asn Cys  Ser Gly Pro Thr Thr
            2100              2105             2110 atc aga ggt caa ttc  tca aac atg tcg ctg  tcc ctg ttg gac ttg      7894
Ile Arg Gly Gln Phe  Ser Asn Met Ser Leu  Ser Leu Leu Asp Leu
            2115              2120             2125 tat tta agt cga ggt  tac aat gta tcg tct  ata gtc act atg aca      7939
Tyr Leu Ser Arg Gly  Tyr Asn Val Ser Ser  Ile Val Thr Met Thr
            2130              2135             2140 tcc cag gga atg tac  ggg gga act tac cta  gtg gaa aag cct aat      7984
Ser Gln Gly Met Tyr  Gly Gly Thr Tyr Leu  Val Glu Lys Pro Asn
            2145              2150             2155 ctg agc agt aaa ggg  tca gag ttg tca caa  ctg agc atg cac cga      8029
Leu Ser Ser Lys Gly  Ser Glu Leu Ser Gln  Leu Ser Met His Arg
            2160              2165             2170 gtg ttt gaa gta ggg  gtt atc aga aat ccg  ggt ttg ggg gct ccg      8074
Val Phe Glu Val Gly  Val Ile Arg Asn Pro  Gly Leu Gly Ala Pro
            2175              2180             2185 gtg ttc cat atg aca  aac tat ttt gag caa  cca gtc agt aat gat      8119
Val Phe His Met Thr  Asn Tyr Phe Glu Gln  Pro Val Ser Asn Asp
            2190              2195             2200 ttc agc aac tgc atg  gtg gct ttg ggg gag  ctt aaa ttc gca gcc      8164
Phe Ser Asn Cys Met  Val Ala Leu Gly Glu  Leu Lys Phe Ala Ala
            2205              2210             2215 ctc tgt cac agg gaa  gat tct atc aca att  ccc tat cag ggg tca      8209
Leu Cys His Arg Glu  Asp Ser Ile Thr Ile  Pro Tyr Gln Gly Ser
            2220              2225             2230 ggg aaa ggt gtc agc  ttc cag ctc gtc aag  cta ggt gtc tgg aaa      8254
Gly Lys Gly Val Ser  Phe Gln Leu Val Lys  Leu Gly Val Trp Lys
            2235              2240             2245 tcc cca act gac atg  cga tcc tgg gtc ccc  cta tca acg gat gat      8299
Ser Pro Thr Asp Met  Arg Ser Trp Val Pro  Leu Ser Thr Asp Asp
            2250              2255             2260 cca gtg ata gat agg  ctt tac ctc tca tct  cac aga ggt gtt atc      8344
Pro Val Ile Asp Arg  Leu Tyr Leu Ser Ser  His Arg Gly Val Ile
            2265              2270             2275 gct gac aat caa gca  aaa tgg gct gtc ccg  aca aca cgg aca gat      8389
Ala Asp Asn Gln Ala  Lys Trp Ala Val Pro  Thr Thr Arg Thr Asp
            2280              2285             2290 gac aag ttg cga atg  gag aca tgc ttc cag  cag gcg tgt aag ggt      8434
Asp Lys Leu Arg Met  Glu Thr Cys Phe Gln  Gln Ala Cys Lys Gly
```

|  |  |
|---|---|
| ```
                       2295                2300                2305
aaa aac caa gca ctc tgc gag aat ccc gag tgg gca cca ttg aag
Lys Asn Gln Ala Leu Cys Glu Asn Pro Glu Trp Ala Pro Leu Lys
            2310                2315                2320 gat aac agg att cct tca tac ggg gtc ttg tct gtt aat ctg agt
Asp Asn Arg Ile Pro Ser Tyr Gly Val Leu Ser Val Asn Leu Ser
            2325                2330                2335 ctg aca gct gag ctt aaa atc aaa att gct tca gga ttc ggg cca
Leu Thr Ala Glu Leu Lys Ile Lys Ile Ala Ser Gly Phe Gly Pro
            2340                2345                2350 ttg atc aca cac ggt tca ggg atg gac cta tac aaa acc aac cac
Leu Ile Thr His Gly Ser Gly Met Asp Leu Tyr Lys Thr Asn His
            2355                2360                2365 aac aat gtg tat tgg ctg act atc ccg cca atg aag aac tta gcc
Asn Asn Val Tyr Trp Leu Thr Ile Pro Pro Met Lys Asn Leu Ala
            2370                2375                2380 tta ggt gta atc aac aca ttg gag tgg ata ccg aga ttc aag gtt
Leu Gly Val Ile Asn Thr Leu Glu Trp Ile Pro Arg Phe Lys Val
            2385                2390                2395 agt ccc aac ctc ttc act gtt cca atc aag gaa gca ggc gag gac
Ser Pro Asn Leu Phe Thr Val Pro Ile Lys Glu Ala Gly Glu Asp
            2400                2405                2410 tgc cat gcc cca aca tac cta cct gcg gag gtg gat ggt gat gtc
Cys His Ala Pro Thr Tyr Leu Pro Ala Glu Val Asp Gly Asp Val
            2415                2420                2425 aaa ctc agt tcc aat ctg gta att cta cct ggt cag gat ctc caa
Lys Leu Ser Ser Asn Leu Val Ile Leu Pro Gly Gln Asp Leu Gln
            2430                2435                2440 tat gtt ttg gca acc tac gat act tcc gca gtt gaa cat gct gtg
Tyr Val Leu Ala Thr Tyr Asp Thr Ser Ala Val Glu His Ala Val
            2445                2450                2455 gtt tat tat gtt tac agc cca agc cgc tca ttt tct tac ttt tat
Val Tyr Tyr Val Tyr Ser Pro Ser Arg Ser Phe Ser Tyr Phe Tyr
            2460                2465                2470 cct ttt agg ttg cct ata aag ggg gtc cca atc gaa tta caa gtg
Pro Phe Arg Leu Pro Ile Lys Gly Val Pro Ile Glu Leu Gln Val
            2475                2480                2485 gaa tgc ttc aca tgg gac aaa aaa ctc tgg tgc cgt cac ttc tgt
Glu Cys Phe Thr Trp Asp Lys Lys Leu Trp Cys Arg His Phe Cys
            2490                2495                2500 gtg ctt gcg gac tca gaa tct ggt gga cat atc act cac tct ggg
Val Leu Ala Asp Ser Glu Ser Gly Gly His Ile Thr His Ser Gly
            2505                2510                2515 atg gtg ggc atg gga gtc agc tgc aca gtc act cgg gaa gat gga
Met Val Gly Met Gly Val Ser Cys Thr Val Thr Arg Glu Asp Gly
            2520                2525                2530 acc aat cgc aga tag ggctgccagt gaaccgatca catgatgtca cccagacatc
Thr Asn Arg Arg aggcataccc actagtgtga aatagacatc agaattaaga aaaacgtagg gtccaagtgg tttcccgtt atg gac tcg cta tct gtc aac cag atc tta tac cct gaa
          Met Asp Ser Leu Ser Val Asn Gln Ile Leu Tyr Pro Glu
                    2535                2540                2545 gtt cac cta gat agc ccg ata gtt acc aat aag ata gta gct atc
Val His Leu Asp Ser Pro Ile Val Thr Asn Lys Ile Val Ala Ile
            2550                2555                2560 ctg gag tat gct cga gtc cct cac gct tac agc ctg gag gac cct
Leu Glu Tyr Ala Arg Val Pro His Ala Tyr Ser Leu Glu Asp Pro
            2565                2570                2575
``` | 8479<br><br>8524<br><br>8569<br><br>8614<br><br>8659<br><br>8704<br><br>8749<br><br>8794<br><br>8839<br><br>8884<br><br>8929<br><br>8974<br><br>9019<br><br>9064<br><br>9109<br><br>9164<br><br>9224<br><br>9272<br><br>9317<br><br>9362 |

-continued

| | | | | | | | | | | | | | | |
|---|---|---|---|---|---|---|---|---|---|---|---|---|---|---|
| aca | ctg | tgt | cag | aac | atc | aag | cac | cgc | cta | aaa | aac | gga | ttc | tcc | 9407 |
| Thr | Leu | Cys | Gln | Asn | Ile | Lys | His | Arg | Leu | Lys | Asn | Gly | Phe | Ser | |
| | | 2580 | | | | 2585 | | | | | 2590 | | | | |

| aac | caa | atg | att | ata | aac | aat | gtg | gaa | gtt | ggg | aat | gtc | atc | aag | 9452 |
|---|---|---|---|---|---|---|---|---|---|---|---|---|---|---|---|
| Asn | Gln | Met | Ile | Ile | Asn | Asn | Val | Glu | Val | Gly | Asn | Val | Ile | Lys | |
| | | 2595 | | | | 2600 | | | | | 2605 | | | | |

| tcc | aag | ctt | agg | agt | tat | ccg | gcc | cac | tct | cat | att | cca | tat | cca | 9497 |
|---|---|---|---|---|---|---|---|---|---|---|---|---|---|---|---|
| Ser | Lys | Leu | Arg | Ser | Tyr | Pro | Ala | His | Ser | His | Ile | Pro | Tyr | Pro | |
| | | 2610 | | | | 2615 | | | | | 2620 | | | | |

| aat | tgt | aat | cag | gat | tta | ttt | aac | ata | gaa | gac | aaa | gag | tca | aca | 9542 |
|---|---|---|---|---|---|---|---|---|---|---|---|---|---|---|---|
| Asn | Cys | Asn | Gln | Asp | Leu | Phe | Asn | Ile | Glu | Asp | Lys | Glu | Ser | Thr | |
| | | 2625 | | | | 2630 | | | | | 2635 | | | | |

| agg | aag | atc | cgt | gag | ctc | cta | aaa | aag | gga | aat | tcg | cta | tac | tcc | 9587 |
|---|---|---|---|---|---|---|---|---|---|---|---|---|---|---|---|
| Arg | Lys | Ile | Arg | Glu | Leu | Leu | Lys | Lys | Gly | Asn | Ser | Leu | Tyr | Ser | |
| | | 2640 | | | | 2645 | | | | | 2650 | | | | |

| aaa | gtc | agt | gat | aag | gtt | ttc | caa | tgc | ctg | agg | gac | act | aac | tca | 9632 |
|---|---|---|---|---|---|---|---|---|---|---|---|---|---|---|---|
| Lys | Val | Ser | Asp | Lys | Val | Phe | Gln | Cys | Leu | Arg | Asp | Thr | Asn | Ser | |
| | | 2655 | | | | 2660 | | | | | 2665 | | | | |

| cgg | ctt | ggc | cta | ggc | tcc | gaa | ttg | agg | gag | gac | atc | aag | gag | aaa | 9677 |
|---|---|---|---|---|---|---|---|---|---|---|---|---|---|---|---|
| Arg | Leu | Gly | Leu | Gly | Ser | Glu | Leu | Arg | Glu | Asp | Ile | Lys | Glu | Lys | |
| | | 2670 | | | | 2675 | | | | | 2680 | | | | |

| att | att | aac | ttg | gga | gtt | tac | atg | cac | agc | tcc | caa | tgg | ttt | gag | 9722 |
|---|---|---|---|---|---|---|---|---|---|---|---|---|---|---|---|
| Ile | Ile | Asn | Leu | Gly | Val | Tyr | Met | His | Ser | Ser | Gln | Trp | Phe | Glu | |
| | | 2685 | | | | 2690 | | | | | 2695 | | | | |

| ccc | ttt | ctg | ttt | tgg | ttt | aca | gtc | aag | act | gag | atg | agg | tca | gtg | 9767 |
|---|---|---|---|---|---|---|---|---|---|---|---|---|---|---|---|
| Pro | Phe | Leu | Phe | Trp | Phe | Thr | Val | Lys | Thr | Glu | Met | Arg | Ser | Val | |
| | | 2700 | | | | 2705 | | | | | 2710 | | | | |

| att | aaa | tca | caa | acc | cat | act | tgc | cat | agg | agg | aga | cac | aca | cct | 9812 |
|---|---|---|---|---|---|---|---|---|---|---|---|---|---|---|---|
| Ile | Lys | Ser | Gln | Thr | His | Thr | Cys | His | Arg | Arg | Arg | His | Thr | Pro | |
| | | 2715 | | | | 2720 | | | | | 2725 | | | | |

| gta | ttc | ttc | act | ggt | agt | tca | gtt | gag | ctg | tta | atc | tct | cgt | gac | 9857 |
|---|---|---|---|---|---|---|---|---|---|---|---|---|---|---|---|
| Val | Phe | Phe | Thr | Gly | Ser | Ser | Val | Glu | Leu | Leu | Ile | Ser | Arg | Asp | |
| | | 2730 | | | | 2735 | | | | | 2740 | | | | |

| ctt | gtt | gct | ata | atc | agt | aag | gag | tct | caa | cat | gta | tat | tac | ctg | 9902 |
|---|---|---|---|---|---|---|---|---|---|---|---|---|---|---|---|
| Leu | Val | Ala | Ile | Ile | Ser | Lys | Glu | Ser | Gln | His | Val | Tyr | Tyr | Leu | |
| | | 2745 | | | | 2750 | | | | | 2755 | | | | |

| acg | ttt | gaa | ctg | gtt | ttg | atg | tat | tgt | gat | gtc | ata | gag | ggg | agg | 9947 |
|---|---|---|---|---|---|---|---|---|---|---|---|---|---|---|---|
| Thr | Phe | Glu | Leu | Val | Leu | Met | Tyr | Cys | Asp | Val | Ile | Glu | Gly | Arg | |
| | | 2760 | | | | 2765 | | | | | 2770 | | | | |

| tta | atg | aca | gag | acc | gct | atg | acc | att | gat | gct | agg | tat | gca | gaa | 9992 |
|---|---|---|---|---|---|---|---|---|---|---|---|---|---|---|---|
| Leu | Met | Thr | Glu | Thr | Ala | Met | Thr | Ile | Asp | Ala | Arg | Tyr | Ala | Glu | |
| | | 2775 | | | | 2780 | | | | | 2785 | | | | |

| ctt | cta | gga | aga | gtc | aga | tac | atg | tgg | aaa | ctg | ata | gat | ggt | ttc | 10037 |
|---|---|---|---|---|---|---|---|---|---|---|---|---|---|---|---|
| Leu | Leu | Gly | Arg | Val | Arg | Tyr | Met | Trp | Lys | Leu | Ile | Asp | Gly | Phe | |
| | | 2790 | | | | 2795 | | | | | 2800 | | | | |

| ttc | cct | gca | ctc | ggg | aat | cca | act | tat | caa | att | gta | gcc | atg | ctg | 10082 |
|---|---|---|---|---|---|---|---|---|---|---|---|---|---|---|---|
| Phe | Pro | Ala | Leu | Gly | Asn | Pro | Thr | Tyr | Gln | Ile | Val | Ala | Met | Leu | |
| | | 2805 | | | | 2810 | | | | | 2815 | | | | |

| gag | cca | ctt | tca | ctt | gct | tac | ctg | caa | ctg | agg | gat | ata | aca | gta | 10127 |
|---|---|---|---|---|---|---|---|---|---|---|---|---|---|---|---|
| Glu | Pro | Leu | Ser | Leu | Ala | Tyr | Leu | Gln | Leu | Arg | Asp | Ile | Thr | Val | |
| | | 2820 | | | | 2825 | | | | | 2830 | | | | |

| gaa | ctc | aga | ggt | gct | ttc | ctt | aac | cac | tgc | ttt | act | gaa | ata | cat | 10172 |
|---|---|---|---|---|---|---|---|---|---|---|---|---|---|---|---|
| Glu | Leu | Arg | Gly | Ala | Phe | Leu | Asn | His | Cys | Phe | Thr | Glu | Ile | His | |
| | | 2835 | | | | 2840 | | | | | 2845 | | | | |

| gat | gtt | ctt | gac | caa | aac | ggg | ttt | tct | gat | gaa | ggt | act | tat | cat | 10217 |
|---|---|---|---|---|---|---|---|---|---|---|---|---|---|---|---|
| Asp | Val | Leu | Asp | Gln | Asn | Gly | Phe | Ser | Asp | Glu | Gly | Thr | Tyr | His | |
| | | 2850 | | | | 2855 | | | | | 2860 | | | | |

| gag | tta | att | gaa | gcc | cta | gat | tac | att | ttc | ata | act | gat | gac | ata | 10262 |
|---|---|---|---|---|---|---|---|---|---|---|---|---|---|---|---|
| Glu | Leu | Ile | Glu | Ala | Leu | Asp | Tyr | Ile | Phe | Ile | Thr | Asp | Asp | Ile | |
| | | 2865 | | | | 2870 | | | | | 2875 | | | | |

```
cat ctg aca ggg gag att ttc tca ttt ttc aga agt ttc ggc cac      10307
His Leu Thr Gly Glu Ile Phe Ser Phe Phe Arg Ser Phe Gly His
        2880                2885                2890 ccc aga ctt gaa gca gta acg gct gct gaa aat gtc agg aaa tac      10352
Pro Arg Leu Glu Ala Val Thr Ala Ala Glu Asn Val Arg Lys Tyr
        2895                2900                2905 atg aat cag cct aaa gtc att gtg tat gag act ctg atg aaa ggt      10397
Met Asn Gln Pro Lys Val Ile Val Tyr Glu Thr Leu Met Lys Gly
        2910                2915                2920 cat gcc ata ttt tgt gga atc ata atc aac ggc tat cgt gac agg      10442
His Ala Ile Phe Cys Gly Ile Ile Ile Asn Gly Tyr Arg Asp Arg
        2925                2930                2935 cac gga ggc agt tgg cca ccc ctg acc ctc ccc ctg cat gct gca      10487
His Gly Gly Ser Trp Pro Pro Leu Thr Leu Pro Leu His Ala Ala
        2940                2945                2950 gac aca atc cgg aat gct caa gct tca ggt gaa ggg tta aca cat      10532
Asp Thr Ile Arg Asn Ala Gln Ala Ser Gly Glu Gly Leu Thr His
        2955                2960                2965 gag cag tgc gtt gat aac tgg aaa tca ttt gct gga gtg aga ttt      10577
Glu Gln Cys Val Asp Asn Trp Lys Ser Phe Ala Gly Val Arg Phe
        2970                2975                2980 ggc tgt ttt atg cct ctt agc ctg gac agt gat ctg aca atg tac      10622
Gly Cys Phe Met Pro Leu Ser Leu Asp Ser Asp Leu Thr Met Tyr
        2985                2990                2995 cta aag gac aag gca ctt gct gct ctc caa agg gaa tgg gat tca      10667
Leu Lys Asp Lys Ala Leu Ala Ala Leu Gln Arg Glu Trp Asp Ser
        3000                3005                3010 gtt tac ccg aaa gag ttc ctg cgt tac gat cct ccc aag gga acc      10712
Val Tyr Pro Lys Glu Phe Leu Arg Tyr Asp Pro Pro Lys Gly Thr
        3015                3020                3025 ggg tca cgg agg ctt gta gat gtt ttc ctt aat gat tcg agc ttt      10757
Gly Ser Arg Arg Leu Val Asp Val Phe Leu Asn Asp Ser Ser Phe
        3030                3035                3040 gac cca tat gat atg ata atg tat gtc gta agt gga gcc tac ctc      10802
Asp Pro Tyr Asp Met Ile Met Tyr Val Val Ser Gly Ala Tyr Leu
        3045                3050                3055 cat gac cct gag ttc aac ctg tct tac agc ctg aaa gaa aag gag      10847
His Asp Pro Glu Phe Asn Leu Ser Tyr Ser Leu Lys Glu Lys Glu
        3060                3065                3070 atc aag gaa aca ggt aga ctt ttc gct aaa atg act tac aaa atg      10892
Ile Lys Glu Thr Gly Arg Leu Phe Ala Lys Met Thr Tyr Lys Met
        3075                3080                3085 agg gca tgc caa gtg atc gct gaa aat cta atc tca aac ggg att      10937
Arg Ala Cys Gln Val Ile Ala Glu Asn Leu Ile Ser Asn Gly Ile
        3090                3095                3100 ggc aag tat ttt aag gac aat ggg atg gcc aag gat gag cac gat      10982
Gly Lys Tyr Phe Lys Asp Asn Gly Met Ala Lys Asp Glu His Asp
        3105                3110                3115 ttg act aag gca ctc cac act ctg gct gtc tca gga gtc ccc aaa      11027
Leu Thr Lys Ala Leu His Thr Leu Ala Val Ser Gly Val Pro Lys
        3120                3125                3130 gat ctc aaa gaa agt cac agg ggg gga cca gtc tta aaa acc tac      11072
Asp Leu Lys Glu Ser His Arg Gly Gly Pro Val Leu Lys Thr Tyr
        3135                3140                3145 tcc cga agc cca gtc cac aca agt acc agg aac gtt aaa gca aaa      11117
Ser Arg Ser Pro Val His Thr Ser Thr Arg Asn Val Lys Ala Lys
        3150                3155                3160 aaa ggg ttt gta gga ttc cct cat gta att cgg cag aat caa gac      11162
Lys Gly Phe Val Gly Phe Pro His Val Ile Arg Gln Asn Gln Asp
```

```
                3165                3170                3175
act gat cat ccg gag aat ata gaa acc tac gag aca gtc agc gca    11207
Thr Asp His Pro Glu Asn Ile Glu Thr Tyr Glu Thr Val Ser Ala
        3180                3185                3190 ttt atc acg act gat ctc aag aag tac tgc ctt aat tgg aga tat    11252
Phe Ile Thr Thr Asp Leu Lys Lys Tyr Cys Leu Asn Trp Arg Tyr
        3195                3200                3205 gag acc atc agc tta ttt gca cag agg cta aat gag att tac gga    11297
Glu Thr Ile Ser Leu Phe Ala Gln Arg Leu Asn Glu Ile Tyr Gly
        3210                3215                3220 tta ccc tca ttt ttt cag tgg ctg cat aag agg ctt gaa acc tct    11342
Leu Pro Ser Phe Phe Gln Trp Leu His Lys Arg Leu Glu Thr Ser
        3225                3230                3235 gtc ctc tat gta agt gac cct cat tgc ccc ccc gac ctt gac gcc    11387
Val Leu Tyr Val Ser Asp Pro His Cys Pro Pro Asp Leu Asp Ala
        3240                3245                3250 cat gtc ccg tta tgc aaa gtc ccc aat gac caa atc ttc atc aag    11432
His Val Pro Leu Cys Lys Val Pro Asn Asp Gln Ile Phe Ile Lys
        3255                3260                3265 tac cct atg gga ggt ata gaa ggg tat tgt cag aag ctg tgg acc    11477
Tyr Pro Met Gly Gly Ile Glu Gly Tyr Cys Gln Lys Leu Trp Thr
        3270                3275                3280 atc agc acc att ccc tac tta tac ctg gct gct tat gag agc ggg    11522
Ile Ser Thr Ile Pro Tyr Leu Tyr Leu Ala Ala Tyr Glu Ser Gly
        3285                3290                3295 gta agg att gct tcg tta gtg caa ggg gac aat cag acc ata gcc    11567
Val Arg Ile Ala Ser Leu Val Gln Gly Asp Asn Gln Thr Ile Ala
        3300                3305                3310 gta aca aaa agg gta ccc agc aca tgg cct tac aac ctt aag aaa    11612
Val Thr Lys Arg Val Pro Ser Thr Trp Pro Tyr Asn Leu Lys Lys
        3315                3320                3325 cgg gaa gct gct aga gta act aga gat tac ttt gta att ctt agg    11657
Arg Glu Ala Ala Arg Val Thr Arg Asp Tyr Phe Val Ile Leu Arg
        3330                3335                3340 caa agg cta cat gac att ggc cat cac ctc aag gca aat gag aca    11702
Gln Arg Leu His Asp Ile Gly His His Leu Lys Ala Asn Glu Thr
        3345                3350                3355 att gtt tca tca cat ttt ttt gtc tat tca aaa gga ata tat tat    11747
Ile Val Ser Ser His Phe Phe Val Tyr Ser Lys Gly Ile Tyr Tyr
        3360                3365                3370 gat ggg cta ctt gtg tcc caa tca ctc aag agc atc gca aga tgt    11792
Asp Gly Leu Leu Val Ser Gln Ser Leu Lys Ser Ile Ala Arg Cys
        3375                3380                3385 gta ttc tgg tca gag act ata gtt gat gaa aca agg gca gca tgc    11837
Val Phe Trp Ser Glu Thr Ile Val Asp Glu Thr Arg Ala Ala Cys
        3390                3395                3400 agt aat att gct aca aca atg gct aaa agc atc gag aga ggt tat    11882
Ser Asn Ile Ala Thr Thr Met Ala Lys Ser Ile Glu Arg Gly Tyr
        3405                3410                3415 gac cgt tat ctt gca tat tcc ctg aac gtc cta aaa gtg ata cag    11927
Asp Arg Tyr Leu Ala Tyr Ser Leu Asn Val Leu Lys Val Ile Gln
        3420                3425                3430 caa att ttg atc tct ctt ggc ttc aca atc aat tca acc atg acc    11972
Gln Ile Leu Ile Ser Leu Gly Phe Thr Ile Asn Ser Thr Met Thr
        3435                3440                3445 cga gat gta gtc ata ccc ctc ctc aca aac aac gat ctc tta ata    12017
Arg Asp Val Val Ile Pro Leu Leu Thr Asn Asn Asp Leu Leu Ile
        3450                3455                3460 agg atg gca ctg ttg ccc gct cct att ggg ggg atg aat tat ctg    12062
```

```
              Arg Met Ala Leu Leu Pro Ala Pro Ile Gly Gly Met Asn Tyr Leu
                      3465                3470                3475 aat atg agc agg ctg ttt gtc aga aac atc ggt gat cca gta aca            12107
Asn Met Ser Arg Leu Phe Val Arg Asn Ile Gly Asp Pro Val Thr
            3480                3485                3490 tca tca att gct gat ctc aag aga atg att ctc gca tca cta atg            12152
Ser Ser Ile Ala Asp Leu Lys Arg Met Ile Leu Ala Ser Leu Met
            3495                3500                3505 cct gaa gag acc ctc cat caa gta atg aca caa caa ccg ggg gac            12197
Pro Glu Glu Thr Leu His Gln Val Met Thr Gln Gln Pro Gly Asp
            3510                3515                3520 tct tca ttc cta gac tgg gct agc gac cct tac tca gca aat ctt            12242
Ser Ser Phe Leu Asp Trp Ala Ser Asp Pro Tyr Ser Ala Asn Leu
            3525                3530                3535 gta tgc gtc cag agc atc act aga ctc ctc aag aac ata act gca            12287
Val Cys Val Gln Ser Ile Thr Arg Leu Leu Lys Asn Ile Thr Ala
            3540                3545                3550 agg ttt gtc cta atc cat agt cca aac cca atg tta aaa ggg tta            12332
Arg Phe Val Leu Ile His Ser Pro Asn Pro Met Leu Lys Gly Leu
            3555                3560                3565 ttc cat gat gac agt aaa gaa gag gac gag aga ctg gcg gca ttc            12377
Phe His Asp Asp Ser Lys Glu Glu Asp Glu Arg Leu Ala Ala Phe
            3570                3575                3580 ctc atg gac agg cat att ata gta cct agg gca gct cat gaa atc            12422
Leu Met Asp Arg His Ile Ile Val Pro Arg Ala Ala His Glu Ile
            3585                3590                3595 ctg gat cat agt gtc aca ggg gca aga gag tct att gca ggc atg            12467
Leu Asp His Ser Val Thr Gly Ala Arg Glu Ser Ile Ala Gly Met
            3600                3605                3610 cta gat acc aca aaa ggc ctg att cga gcc agc atg agg aag ggg            12512
Leu Asp Thr Thr Lys Gly Leu Ile Arg Ala Ser Met Arg Lys Gly
            3615                3620                3625 ggg tta acc tct cga gtg ata acc aga ttg tcc aat tat gac tat            12557
Gly Leu Thr Ser Arg Val Ile Thr Arg Leu Ser Asn Tyr Asp Tyr
            3630                3635                3640 gaa caa ttt aga gca ggg atg gtg cta ttg aca gga aga aag aga            12602
Glu Gln Phe Arg Ala Gly Met Val Leu Leu Thr Gly Arg Lys Arg
            3645                3650                3655 aat gtc ctc att gac aaa gag tca tgt tca gtg cag ctg gct aga            12647
Asn Val Leu Ile Asp Lys Glu Ser Cys Ser Val Gln Leu Ala Arg
            3660                3665                3670 gcc cta aga agc cat atg tgg gca aga cta gct cga gga cgg cct            12692
Ala Leu Arg Ser His Met Trp Ala Arg Leu Ala Arg Gly Arg Pro
            3675                3680                3685 att tac ggc ctt gag gtc cct gat gta cta gaa tct atg cga ggc            12737
Ile Tyr Gly Leu Glu Val Pro Asp Val Leu Glu Ser Met Arg Gly
            3690                3695                3700 cac ctt att cgg cgt cat gag aca tgt gtc atc tgc gag tgt gga            12782
His Leu Ile Arg Arg His Glu Thr Cys Val Ile Cys Glu Cys Gly
            3705                3710                3715 tca gtc aac tac gga tgg ttt ttt gtc ccc tcg ggt tgc caa ctg            12827
Ser Val Asn Tyr Gly Trp Phe Phe Val Pro Ser Gly Cys Gln Leu
            3720                3725                3730 gat gat att gac aag gaa aca tca tcc ttg aga gtc cca tat att            12872
Asp Asp Ile Asp Lys Glu Thr Ser Ser Leu Arg Val Pro Tyr Ile
            3735                3740                3745 ggt tct acc act gat gag aga aca gac atg aag ctc gca ttc gta            12917
Gly Ser Thr Thr Asp Glu Arg Thr Asp Met Lys Leu Ala Phe Val
            3750                3755                3760
```

```
aga gcc cca agt aga tcc ttg cga tct gcc gtt aga ata gca aca      12962
Arg Ala Pro Ser Arg Ser Leu Arg Ser Ala Val Arg Ile Ala Thr
        3765            3770            3775 gtg tac tca tgg gct tac ggt gat gat gat agc tct tgg aac gaa      13007
Val Tyr Ser Trp Ala Tyr Gly Asp Asp Asp Ser Ser Trp Asn Glu
        3780            3785            3790 gcc tgg ttg ttg gca agg caa agg gcc aat gtg agc ctg gag gag      13052
Ala Trp Leu Leu Ala Arg Gln Arg Ala Asn Val Ser Leu Glu Glu
        3795            3800            3805 cta agg gtg atc act ccc atc tcg act tcg act aat tta gcg cat      13097
Leu Arg Val Ile Thr Pro Ile Ser Thr Ser Thr Asn Leu Ala His
        3810            3815            3820 agg ttg agg gat cgt agc act caa gtg aaa tac tca ggt aca tcc      13142
Arg Leu Arg Asp Arg Ser Thr Gln Val Lys Tyr Ser Gly Thr Ser
        3825            3830            3835 ctt gtc cga gtg gca agg tat acc aca atc tcc aac gac aat ctc      13187
Leu Val Arg Val Ala Arg Tyr Thr Thr Ile Ser Asn Asp Asn Leu
        3840            3845            3850 tca ttt gtc ata tca gat aag aag gtt gat act aac ttt ata tac      13232
Ser Phe Val Ile Ser Asp Lys Lys Val Asp Thr Asn Phe Ile Tyr
        3855            3860            3865 caa caa gga atg ctt cta ggg ttg ggt gtt tta gaa aca ttg ttt      13277
Gln Gln Gly Met Leu Leu Gly Leu Gly Val Leu Glu Thr Leu Phe
        3870            3875            3880 cga ctc gag aaa gat act gga tca tct aac acg gta tta cat ctt      13322
Arg Leu Glu Lys Asp Thr Gly Ser Ser Asn Thr Val Leu His Leu
        3885            3890            3895 cac gtc gaa aca gat tgt tgc gtg atc ccg atg ata gat cat ccc      13367
His Val Glu Thr Asp Cys Cys Val Ile Pro Met Ile Asp His Pro
        3900            3905            3910 agg ata ccc agc tcc cgc aag cta gag ctg agg gca gag cta tgt      13412
Arg Ile Pro Ser Ser Arg Lys Leu Glu Leu Arg Ala Glu Leu Cys
        3915            3920            3925 acc aac cca ttg ata tat gat aat gca cct tta att gac aga gat      13457
Thr Asn Pro Leu Ile Tyr Asp Asn Ala Pro Leu Ile Asp Arg Asp
        3930            3935            3940 gca aca agg cta tac acc cag agc cat agg agg cac ctt gtg gaa      13502
Ala Thr Arg Leu Tyr Thr Gln Ser His Arg Arg His Leu Val Glu
        3945            3950            3955 ttt gtt aca tgg tcc aca ccc caa cta tat cac att cta gct aag      13547
Phe Val Thr Trp Ser Thr Pro Gln Leu Tyr His Ile Leu Ala Lys
        3960            3965            3970 tcc aca gca cta tct atg att gac ctg gta aca aaa ttt gag aag      13592
Ser Thr Ala Leu Ser Met Ile Asp Leu Val Thr Lys Phe Glu Lys
        3975            3980            3985 gac cat atg aat gaa att tca gct ctc ata ggg gat gac gat atc      13637
Asp His Met Asn Glu Ile Ser Ala Leu Ile Gly Asp Asp Asp Ile
        3990            3995            4000 aat agt ttc ata act gag ttt ctg ctt ata gag cca aga tta ttc      13682
Asn Ser Phe Ile Thr Glu Phe Leu Leu Ile Glu Pro Arg Leu Phe
        4005            4010            4015 acc atc tac ttg ggc cag tgt gca gcc atc aat tgg gca ttt gat      13727
Thr Ile Tyr Leu Gly Gln Cys Ala Ala Ile Asn Trp Ala Phe Asp
        4020            4025            4030 gta cat tat cat aga cca tca ggg aaa tat cag atg ggt gag ctg      13772
Val His Tyr His Arg Pro Ser Gly Lys Tyr Gln Met Gly Glu Leu
        4035            4040            4045 ttg tct tcg ttc ctt tct aga atg agc aaa gga gtg ttt aag gtg      13817
Leu Ser Ser Phe Leu Ser Arg Met Ser Lys Gly Val Phe Lys Val
        4050            4055            4060
```

-continued

| | | | | | | | | | | | | |
|---|---|---|---|---|---|---|---|---|---|---|---|---|
| ctt | gtc | aat | gct | cta | agc | cac | cca | aag | atc | tac | aag | aaa | ttc | tgg | 13862 |
| Leu | Val | Asn | Ala | Leu | Ser | His | Pro | Lys | Ile | Tyr | Lys | Lys | Phe | Trp | |
| | | 4065 | | | | 4070 | | | | 4075 | | | | | |

| cat | tgt | ggt | att | ata | gag | cct | atc | cat | ggt | cct | tca | ctt | gat | gct | 13907 |
| His | Cys | Gly | Ile | Ile | Glu | Pro | Ile | His | Gly | Pro | Ser | Leu | Asp | Ala | |
| | 4080 | | | | | 4085 | | | | | 4090 | | | | |

| caa | aac | ttg | cac | aca | act | gtg | tgc | aac | atg | gtt | tac | aca | tgc | tat | 13952 |
| Gln | Asn | Leu | His | Thr | Thr | Val | Cys | Asn | Met | Val | Tyr | Thr | Cys | Tyr | |
| | 4095 | | | | | 4100 | | | | | 4105 | | | | |

| atg | acc | tac | ctc | gac | ctg | ttg | ttg | aat | gaa | gag | tta | gaa | gag | ttc | 13997 |
| Met | Thr | Tyr | Leu | Asp | Leu | Leu | Leu | Asn | Glu | Glu | Leu | Glu | Glu | Phe | |
| 4110 | | | | | 4115 | | | | | 4120 | | | | | |

| aca | ttt | ctt | ttg | tgt | gaa | agc | gat | gag | gat | gta | gta | ccg | gac | aga | 14042 |
| Thr | Phe | Leu | Leu | Cys | Glu | Ser | Asp | Glu | Asp | Val | Val | Pro | Asp | Arg | |
| | 4125 | | | | | 4130 | | | | | 4135 | | | | |

| ttc | gac | aac | atc | cag | gca | aaa | cac | ttg | tgt | gtt | ctg | gca | gat | ttg | 14087 |
| Phe | Asp | Asn | Ile | Gln | Ala | Lys | His | Leu | Cys | Val | Leu | Ala | Asp | Leu | |
| | 4140 | | | | | 4145 | | | | | 4150 | | | | |

| tac | tgt | caa | ccg | ggg | acc | tgc | cca | ccg | att | cga | ggt | cta | agg | ccg | 14132 |
| Tyr | Cys | Gln | Pro | Gly | Thr | Cys | Pro | Pro | Ile | Arg | Gly | Leu | Arg | Pro | |
| | 4155 | | | | | 4160 | | | | | 4165 | | | | |

| gta | gag | aaa | tgt | gca | gtt | cta | acc | gat | cat | atc | aag | aca | gag | gct | 14177 |
| Val | Glu | Lys | Cys | Ala | Val | Leu | Thr | Asp | His | Ile | Lys | Thr | Glu | Ala | |
| 4170 | | | | | 4175 | | | | | 4180 | | | | | |

| agg | tta | tct | cca | gca | gga | tct | tcg | tgg | aac | ata | aat | cca | att | att | 14222 |
| Arg | Leu | Ser | Pro | Ala | Gly | Ser | Ser | Trp | Asn | Ile | Asn | Pro | Ile | Ile | |
| | 4185 | | | | | 4190 | | | | | 4195 | | | | |

| gta | gac | cat | tac | tca | tgc | tct | ctg | act | tat | ctc | cgt | cga | gga | tct | 14267 |
| Val | Asp | His | Tyr | Ser | Cys | Ser | Leu | Thr | Tyr | Leu | Arg | Arg | Gly | Ser | |
| | 4200 | | | | | 4205 | | | | | 4210 | | | | |

| atc | aaa | cag | ata | aga | ttg | aga | gtt | gat | cca | gga | ttc | att | ttt | gac | 14312 |
| Ile | Lys | Gln | Ile | Arg | Leu | Arg | Val | Asp | Pro | Gly | Phe | Ile | Phe | Asp | |
| 4215 | | | | | 4220 | | | | | 4225 | | | | | |

| gcc | ctc | gct | gag | gta | aat | gtc | agt | cag | cca | aag | gtc | ggc | agc | aac | 14357 |
| Ala | Leu | Ala | Glu | Val | Asn | Val | Ser | Gln | Pro | Lys | Val | Gly | Ser | Asn | |
| | 4230 | | | | | 4235 | | | | | 4240 | | | | |

| aac | atc | tca | aat | atg | agc | atc | aag | gat | ttc | aga | cct | cca | cac | gat | 14402 |
| Asn | Ile | Ser | Asn | Met | Ser | Ile | Lys | Asp | Phe | Arg | Pro | Pro | His | Asp | |
| 4245 | | | | | 4250 | | | | | 4255 | | | | | |

| gat | gtt | gca | aaa | ttg | ctc | aaa | gat | atc | aac | aca | agc | aag | cac | aat | 14447 |
| Asp | Val | Ala | Lys | Leu | Leu | Lys | Asp | Ile | Asn | Thr | Ser | Lys | His | Asn | |
| | 4260 | | | | | 4265 | | | | | 4270 | | | | |

| ctt | ccc | att | tca | ggg | ggt | agt | ctc | gcc | aat | tat | gaa | atc | cat | gct | 14492 |
| Leu | Pro | Ile | Ser | Gly | Gly | Ser | Leu | Ala | Asn | Tyr | Glu | Ile | His | Ala | |
| | 4275 | | | | | 4280 | | | | | 4285 | | | | |

| ttc | cgc | aga | atc | ggg | tta | aac | tca | tct | gct | tgc | tac | aaa | gct | gtt | 14537 |
| Phe | Arg | Arg | Ile | Gly | Leu | Asn | Ser | Ser | Ala | Cys | Tyr | Lys | Ala | Val | |
| | 4290 | | | | | 4295 | | | | | 4300 | | | | |

| gag | ata | tca | aca | tta | att | agg | aga | tgc | ctt | gag | cca | ggg | gaa | gac | 14582 |
| Glu | Ile | Ser | Thr | Leu | Ile | Arg | Arg | Cys | Leu | Glu | Pro | Gly | Glu | Asp | |
| | | 4305 | | | | 4310 | | | | 4315 | | | | | |

| ggc | ttg | ttc | ttg | ggt | gag | ggg | tcg | ggt | tct | atg | ttg | atc | act | tat | 14627 |
| Gly | Leu | Phe | Leu | Gly | Glu | Gly | Ser | Gly | Ser | Met | Leu | Ile | Thr | Tyr | |
| 4320 | | | | | 4325 | | | | | 4330 | | | | | |

| aag | gag | ata | cta | aaa | cta | aac | aag | tgc | ttc | tat | aat | agt | ggg | gtt | 14672 |
| Lys | Glu | Ile | Leu | Lys | Leu | Asn | Lys | Cys | Phe | Tyr | Asn | Ser | Gly | Val | |
| | 4335 | | | | | 4340 | | | | | 4345 | | | | |

| tcc | gcc | aat | tct | aga | tct | ggt | caa | agg | gaa | tta | gca | ccc | tat | ccc | 14717 |
| Ser | Ala | Asn | Ser | Arg | Ser | Gly | Gln | Arg | Glu | Leu | Ala | Pro | Tyr | Pro | |

```
                    4350               4355               4360 tcc gaa gtt ggc ctt gtc gaa cac aga atg gga gta ggt aat att        14762
Ser Glu Val Gly Leu Val Glu His Arg Met Gly Val Gly Asn Ile
        4365               4370               4375 gtc aag gtg ctc ttt aac ggg agg ccc gaa gtc acg tgg gta ggc        14807
Val Lys Val Leu Phe Asn Gly Arg Pro Glu Val Thr Trp Val Gly
        4380               4385               4390 agt ata gat tgc ttc aat ttc ata gtc agt aat atc cct acc tct        14852
Ser Ile Asp Cys Phe Asn Phe Ile Val Ser Asn Ile Pro Thr Ser
        4395               4400               4405 agt gtg ggg ttt atc cat tca gat ata gag acc tta cct aac aaa        14897
Ser Val Gly Phe Ile His Ser Asp Ile Glu Thr Leu Pro Asn Lys
        4410               4415               4420 gat act ata gag aag cta gag gaa ttg gca gcc atc tta tcg atg        14942
Asp Thr Ile Glu Lys Leu Glu Glu Leu Ala Ala Ile Leu Ser Met
        4425               4430               4435 gct cta ctc ctt ggc aaa ata gga tca ata ctg gtg att aag ctt        14987
Ala Leu Leu Leu Gly Lys Ile Gly Ser Ile Leu Val Ile Lys Leu
        4440               4445               4450 atg cct ttc agc ggg gat ttt gtt cag gga ttt ata agc tat gta        15032
Met Pro Phe Ser Gly Asp Phe Val Gln Gly Phe Ile Ser Tyr Val
        4455               4460               4465 ggg tct cat tat aga gaa gtg aac ctt gtc tac cct agg tac agc        15077
Gly Ser His Tyr Arg Glu Val Asn Leu Val Tyr Pro Arg Tyr Ser
        4470               4475               4480 aac ttc ata tct act gaa tct tat tta gtt ttg aca gat ctc aaa        15122
Asn Phe Ile Ser Thr Glu Ser Tyr Leu Val Leu Thr Asp Leu Lys
        4485               4490               4495 gct aac cgg cta atg aat cct gaa aag atc aag cag cag ata att        15167
Ala Asn Arg Leu Met Asn Pro Glu Lys Ile Lys Gln Gln Ile Ile
        4500               4505               4510 gaa tca tct gtg cgg act tca cct gga ctt ata ggt cac atc cta        15212
Glu Ser Ser Val Arg Thr Ser Pro Gly Leu Ile Gly His Ile Leu
        4515               4520               4525 tcc att aag caa cta agc tgc ata caa gca att gtg gga ggc gca        15257
Ser Ile Lys Gln Leu Ser Cys Ile Gln Ala Ile Val Gly Gly Ala
        4530               4535               4540 gtt agt aga ggt gat atc aac cct att ctg aaa aaa ctt aca cct        15302
Val Ser Arg Gly Asp Ile Asn Pro Ile Leu Lys Lys Leu Thr Pro
        4545               4550               4555 ata gag cag gtg ctg atc agt tgc ggg ttg gca att aac gga cct        15347
Ile Glu Gln Val Leu Ile Ser Cys Gly Leu Ala Ile Asn Gly Pro
        4560               4565               4570 aaa ctg tgc aaa gaa tta atc cac cat gat gtt gcc tca ggg caa        15392
Lys Leu Cys Lys Glu Leu Ile His His Asp Val Ala Ser Gly Gln
        4575               4580               4585 gat gga ttg ctt aac tct ata ctc atc ctc tac agg gag ttg gca        15437
Asp Gly Leu Leu Asn Ser Ile Leu Ile Leu Tyr Arg Glu Leu Ala
        4590               4595               4600 aga ttc aaa gac aac caa aga agt caa caa ggg atg ttc cac gct        15482
Arg Phe Lys Asp Asn Gln Arg Ser Gln Gln Gly Met Phe His Ala
        4605               4610               4615 tac ccc gta ttg gta agt agt agg caa cga gaa ctt gta tct agg        15527
Tyr Pro Val Leu Val Ser Ser Arg Gln Arg Glu Leu Val Ser Arg
        4620               4625               4630 atc act cgc aaa ttt tgg ggg cat att ctt ctt tac tcc ggg aac        15572
Ile Thr Arg Lys Phe Trp Gly His Ile Leu Leu Tyr Ser Gly Asn
        4635               4640               4645 aga aag ttg ata aat cgg ttt atc cag aat ctc aag tcc ggt tat        15617
```

-continued

```
                Arg Lys Leu Ile Asn Arg Phe Ile Gln Asn Leu Lys Ser Gly Tyr
                    4650                4655                4660 cta gta cta gac tta cac cag aat atc ttc gtt aag aat cta tcc          15662
Leu Val Leu Asp Leu His Gln Asn Ile Phe Val Lys Asn Leu Ser
    4665                4670                4675 aag tca gag aaa cag att att atg acg ggg ggt tta aaa cgt gag          15707
Lys Ser Glu Lys Gln Ile Ile Met Thr Gly Gly Leu Lys Arg Glu
    4680                4685                4690 tgg gtt ttt aag gta aca gtc aag gag acc aaa gaa tgg tac aag          15752
Trp Val Phe Lys Val Thr Val Lys Glu Thr Lys Glu Trp Tyr Lys
    4695                4700                4705 tta gtc gga tac agc gct ctg att aag gat taa ttggttgaac               15795
Leu Val Gly Tyr Ser Ala Leu Ile Lys Asp
    4710                4715 tccggaaccc taatcctgcc ctaggtagtt aggcattatt tgcaatatat taaagaaaac   15855
tttgaaaata cgaagtttct attcccagct ttgtctggt                           15894

<210> SEQ ID NO 2
<211> LENGTH: 525
<212> TYPE: PRT
<213> ORGANISM: Measles virus

<400> SEQUENCE: 2

Met Ala Thr Leu Leu Arg Ser Leu Ala Leu Phe Lys Arg Asn Lys Asp
1               5                   10                  15

Lys Pro Pro Ile Thr Ser Gly Ser Gly Gly Ala Ile Arg Gly Ile Lys
            20                  25                  30

His Ile Ile Ile Val Pro Ile Pro Gly Asp Ser Ser Ile Thr Thr Arg
        35                  40                  45

Ser Arg Leu Leu Asp Arg Leu Val Arg Leu Ile Gly Asn Pro Asp Val
    50                  55                  60

Ser Gly Pro Lys Leu Thr Gly Ala Leu Ile Gly Ile Leu Ser Leu Phe
65                  70                  75                  80

Val Glu Ser Pro Gly Gln Leu Ile Gln Arg Ile Thr Asp Asp Pro Asp
                85                  90                  95

Val Ser Ile Arg Leu Leu Glu Val Val Gln Ser Asp Gln Ser Gln Ser
            100                 105                 110

Gly Leu Thr Phe Ala Ser Arg Gly Thr Asn Met Glu Asp Glu Ala Asp
        115                 120                 125

Gln Tyr Phe Ser His Asp Asp Pro Ser Asn Ser Asp Gln Ser Arg Ser
    130                 135                 140

Gly Trp Phe Glu Asn Lys Glu Ile Ser Asp Ile Glu Val Gln Asp Pro
145                 150                 155                 160

Glu Gly Phe Asn Met Ile Leu Gly Thr Ile Leu Ala Gln Ile Trp Val
                165                 170                 175

Leu Leu Ala Lys Ala Val Thr Ala Pro Asp Thr Ala Ala Asp Ser Glu
            180                 185                 190

Leu Arg Arg Trp Ile Lys Tyr Thr Gln Gln Arg Arg Val Val Gly Glu
        195                 200                 205

Phe Arg Leu Glu Arg Lys Trp Leu Asp Val Val Arg Asn Arg Ile Ala
    210                 215                 220

Glu Asp Leu Ser Leu Arg Arg Phe Met Val Ala Leu Ile Leu Asp Ile
225                 230                 235                 240

Lys Arg Thr Pro Gly Asn Lys Pro Arg Ile Ala Glu Met Ile Cys Asp
                245                 250                 255
```

```
Ile Asp Thr Tyr Ile Val Glu Ala Gly Leu Ala Ser Phe Ile Leu Thr
            260                 265                 270

Ile Lys Phe Gly Ile Glu Thr Met Tyr Pro Ala Leu Gly Leu His Glu
        275                 280                 285

Phe Ala Gly Glu Leu Ser Thr Leu Glu Ser Leu Met Asn Leu Tyr Gln
    290                 295                 300

Gln Met Gly Glu Thr Ala Pro Tyr Met Val Ile Leu Glu Asn Ser Ile
305                 310                 315                 320

Gln Asn Lys Phe Ser Ala Gly Ser Tyr Pro Leu Leu Trp Ser Tyr Ala
                325                 330                 335

Met Gly Val Gly Val Glu Leu Glu Asn Ser Met Gly Gly Leu Asn Phe
            340                 345                 350

Gly Arg Ser Tyr Phe Asp Pro Ala Tyr Phe Arg Leu Gly Gln Glu Met
        355                 360                 365

Val Arg Arg Ser Ala Gly Lys Val Ser Ser Thr Leu Ala Ser Glu Leu
    370                 375                 380

Gly Ile Thr Ala Glu Asp Ala Arg Leu Val Ser Glu Ile Ala Met His
385                 390                 395                 400

Thr Thr Glu Asp Arg Ile Ser Arg Ala Val Gly Pro Arg Gln Ala Gln
                405                 410                 415

Val Ser Phe Leu His Gly Asp Gln Ser Glu Asn Glu Leu Pro Gly Leu
            420                 425                 430

Gly Gly Lys Glu Asp Arg Arg Val Lys Gln Gly Arg Gly Glu Ala Arg
        435                 440                 445

Glu Asn Tyr Arg Glu Thr Gly Ser Ser Arg Ala Ser Asp Ala Arg Ala
    450                 455                 460

Ala His Pro Pro Thr Ser Met Pro Leu Asp Ile Asp Thr Ala Ser Glu
465                 470                 475                 480

Ser Gly Gln Asp Pro Gln Asp Ser Gln Arg Ser Ala Asp Ala Leu Leu
                485                 490                 495

Arg Leu Gln Ala Met Ala Gly Ile Leu Glu Glu Gln Gly Ser Asp Thr
            500                 505                 510

Asp Thr Pro Arg Val Tyr Asn Asp Arg Asp Leu Leu Asp
        515                 520                 525

<210> SEQ ID NO 3
<211> LENGTH: 507
<212> TYPE: PRT
<213> ORGANISM: Measles virus

<400> SEQUENCE: 3

Met Ala Glu Glu Gln Ala Arg His Val Lys Asn Gly Leu Glu Cys Ile
1               5                   10                  15

Arg Ala Leu Lys Ala Glu Pro Ile Gly Ser Leu Ala Val Glu Glu Ala
            20                  25                  30

Met Ala Ala Trp Ser Glu Ile Ser Asp Asn Pro Gly Gln Asp Arg Ala
        35                  40                  45

Thr Cys Lys Glu Glu Glu Ala Gly Ser Ser Gly Leu Ser Lys Pro Cys
    50                  55                  60

Leu Ser Ala Ile Gly Ser Thr Glu Gly Gly Ala Pro Arg Ile Arg Gly
65                  70                  75                  80

Gln Gly Ser Gly Glu Ser Asp Asp Asp Ala Glu Thr Leu Gly Ile Pro
                85                  90                  95

Ser Arg Asn Leu Gln Ala Ser Ser Thr Gly Leu Gln Cys Tyr His Val
            100                 105                 110
```

Tyr Asp His Ser Gly Glu Ala Val Lys Gly Ile Gln Asp Ala Asp Ser
            115                 120                 125

Ile Met Val Gln Ser Gly Leu Asp Gly Asp Ser Thr Leu Ser Gly Gly
130                 135                 140

Asp Asp Glu Ser Glu Asn Ser Asp Val Asp Leu Gly Glu Pro Asp Thr
145                 150                 155                 160

Glu Gly Tyr Ala Ile Thr Asp Arg Gly Ser Ala Pro Ile Ser Met Gly
                165                 170                 175

Phe Arg Ala Ser Asp Val Glu Thr Ala Glu Gly Glu Ile His Glu
                180                 185                 190

Leu Leu Lys Leu Gln Ser Arg Gly Asn Asn Phe Pro Lys Leu Gly Lys
            195                 200                 205

Thr Leu Asn Val Pro Pro Pro Asn Pro Ser Arg Ala Ser Thr Ser
210                 215                 220

Glu Thr Pro Ile Lys Lys Gly Thr Asp Ala Arg Leu Ala Ser Phe Gly
225                 230                 235                 240

Thr Glu Ile Ala Ser Leu Leu Thr Gly Gly Ala Thr Gln Cys Ala Arg
                245                 250                 255

Lys Ser Pro Ser Glu Pro Ser Gly Pro Gly Ala Pro Ala Gly Asn Val
            260                 265                 270

Pro Glu Cys Val Ser Asn Ala Ala Leu Ile Gln Glu Trp Thr Pro Glu
            275                 280                 285

Ser Gly Thr Thr Ile Ser Pro Arg Ser Gln Asn Asn Glu Glu Gly Gly
            290                 295                 300

Asp Tyr Tyr Asp Asp Glu Leu Phe Ser Asp Val Gln Asp Ile Lys Thr
305                 310                 315                 320

Ala Leu Ala Lys Ile His Glu Asp Asn Gln Lys Ile Ile Ser Lys Leu
                325                 330                 335

Glu Ser Leu Leu Leu Leu Lys Gly Glu Val Glu Ser Ile Lys Lys Gln
            340                 345                 350

Ile Asn Arg Gln Asn Ile Ser Ile Ser Thr Leu Glu Gly His Leu Ser
            355                 360                 365

Ser Ile Met Ile Ala Ile Pro Gly Leu Gly Lys Asp Pro Asn Asp Pro
            370                 375                 380

Thr Ala Asp Val Glu Leu Asn Pro Asp Leu Lys Pro Ile Ile Gly Arg
385                 390                 395                 400

Asp Ser Gly Arg Ala Leu Ala Glu Val Leu Lys Pro Val Ala Ser
                405                 410                 415

Arg Gln Leu Gln Gly Met Thr Asn Gly Arg Thr Ser Arg Gly Gln
            420                 425                 430

Leu Leu Lys Glu Phe Gln Leu Lys Pro Ile Gly Lys Lys Val Ser Ser
            435                 440                 445

Ala Val Gly Phe Val Pro Asp Thr Gly Pro Ala Ser Arg Ser Val Ile
450                 455                 460

Arg Ser Ile Ile Lys Ser Ser Arg Leu Glu Glu Asp Arg Lys Arg Tyr
465                 470                 475                 480

Leu Met Thr Leu Leu Asp Asp Ile Lys Gly Ala Asn Asp Leu Ala Lys
                485                 490                 495

Phe His Gln Met Leu Met Lys Ile Ile Met Lys
                500                 505

<210> SEQ ID NO 4
<211> LENGTH: 335

<212> TYPE: PRT
<213> ORGANISM: Measles virus

<400> SEQUENCE: 4

```
Met Thr Glu Ile Tyr Asp Phe Asp Lys Ser Ala Trp Asp Ile Lys Gly
1               5                   10                  15

Ser Ile Ala Pro Ile Gln Pro Thr Thr Tyr Ser Asp Gly Arg Leu Val
            20                  25                  30

Pro Gln Val Arg Val Ile Asp Pro Gly Leu Gly Asp Arg Lys Asp Glu
        35                  40                  45

Cys Phe Met Tyr Met Phe Leu Leu Gly Val Val Glu Asp Ser Asp Pro
    50                  55                  60

Leu Gly Pro Pro Ile Gly Arg Ala Phe Gly Ser Leu Pro Leu Gly Val
65                  70                  75                  80

Gly Arg Pro Thr Ala Lys Pro Glu Glu Leu Leu Lys Glu Ala Thr Glu
                85                  90                  95

Leu Asp Ile Val Val Arg Arg Thr Ala Gly Leu Asn Glu Lys Leu Val
            100                 105                 110

Phe Tyr Asn Asn Thr Pro Leu Thr Leu Leu Thr Pro Trp Arg Lys Val
        115                 120                 125

Leu Thr Thr Gly Ser Val Phe Asn Ala Asn Gln Val Cys Asn Ala Val
130                 135                 140

Asn Leu Ile Pro Leu Asp Thr Pro Gln Arg Phe Arg Val Val Tyr Met
145                 150                 155                 160

Ser Ile Thr Arg Leu Ser Asp Asn Gly Tyr Tyr Thr Val Pro Arg Arg
                165                 170                 175

Met Leu Glu Phe Arg Ser Val Asn Ala Val Ala Phe Asn Leu Leu Val
            180                 185                 190

Thr Leu Arg Ile Asp Lys Ala Ile Gly Pro Gly Lys Ile Ile Asp Asn
        195                 200                 205

Ala Glu Gln Leu Pro Glu Ala Thr Phe Met Val His Ile Gly Asn Phe
    210                 215                 220

Arg Arg Lys Lys Ser Glu Val Tyr Ser Ala Asp Tyr Cys Lys Met Lys
225                 230                 235                 240

Ile Glu Lys Met Gly Leu Val Phe Ala Leu Gly Gly Ile Gly Gly Thr
                245                 250                 255

Ser Leu His Ile Arg Ser Thr Gly Lys Met Ser Lys Thr Leu His Ala
            260                 265                 270

Gln Leu Gly Phe Lys Lys Thr Leu Cys Tyr Pro Leu Met Asp Ile Asn
        275                 280                 285

Glu Asp Leu Asn Arg Leu Leu Trp Arg Ser Arg Cys Lys Ile Val Arg
    290                 295                 300

Ile Gln Ala Val Leu Gln Pro Ser Val Pro Gln Glu Phe Arg Ile Tyr
305                 310                 315                 320

Asp Asp Val Ile Ile Asn Asp Asp Gln Gly Leu Phe Lys Val Leu
                325                 330                 335
```

<210> SEQ ID NO 5
<211> LENGTH: 550
<212> TYPE: PRT
<213> ORGANISM: Measles virus

<400> SEQUENCE: 5

```
Met Gly Leu Lys Val Asn Val Ser Ala Ile Phe Met Ala Val Leu Leu
1               5                   10                  15
```

-continued

```
Thr Leu Gln Thr Pro Thr Gly Gln Ile His Trp Gly Asn Leu Ser Lys
         20                  25                  30

Ile Gly Val Val Gly Ile Gly Ser Ala Ser Tyr Lys Val Met Thr Arg
             35                  40                  45

Ser Ser His Gln Ser Leu Val Ile Lys Leu Met Pro Asn Ile Thr Leu
 50                  55                  60

Leu Asn Asn Cys Thr Arg Val Glu Ile Ala Glu Tyr Arg Arg Leu Leu
 65                  70                  75                  80

Arg Thr Val Leu Glu Pro Ile Arg Asp Ala Leu Asn Ala Met Thr Gln
                 85                  90                  95

Asn Ile Arg Pro Val Gln Ser Val Ala Ser Ser Arg Arg His Lys Arg
            100                 105                 110

Phe Ala Gly Val Val Leu Ala Gly Ala Ala Leu Gly Val Ala Thr Ala
            115                 120                 125

Ala Gln Ile Thr Ala Gly Ile Ala Leu His Gln Ser Met Leu Asn Ser
130                 135                 140

Gln Ala Ile Asp Asn Leu Arg Ala Ser Leu Glu Thr Thr Asn Gln Ala
145                 150                 155                 160

Ile Glu Ala Ile Arg Gln Ala Gly Gln Glu Met Ile Leu Ala Ala Gln
                165                 170                 175

Gly Val Gln Asp Tyr Ile Asn Asn Glu Leu Ile Pro Ser Met Asn Gln
            180                 185                 190

Leu Ser Cys Asp Leu Ile Gly Gln Lys Leu Gly Leu Lys Leu Leu Arg
            195                 200                 205

Tyr Tyr Thr Glu Ile Leu Ser Leu Phe Gly Pro Ser Leu Arg Asp Pro
210                 215                 220

Ile Ser Ala Glu Ile Ser Ile Gln Ala Ser Ser Tyr Ala Leu Gly Gly
225                 230                 235                 240

Asp Ile Asn Lys Val Leu Glu Lys Leu Gly Tyr Ser Gly Gly Asp Leu
                245                 250                 255

Leu Gly Ile Leu Glu Ser Arg Gly Ile Lys Ala Arg Ile Thr His Val
            260                 265                 270

Asp Thr Glu Ser Tyr Phe Ile Val Leu Ser Ile Ala Tyr Pro Thr Leu
            275                 280                 285

Ser Glu Ile Lys Gly Val Ile Val His Arg Leu Glu Gly Val Ser Tyr
290                 295                 300

Asn Ile Gly Ser Gln Glu Trp Tyr Thr Thr Val Pro Lys Tyr Val Ala
305                 310                 315                 320

Thr Gln Gly Tyr Leu Ile Ser Asn Phe Asp Glu Ser Ser Cys Thr Phe
                325                 330                 335

Met Pro Glu Gly Thr Val Cys Ser Gln Asn Ala Leu Tyr Pro Met Ser
            340                 345                 350

Pro Leu Leu Gln Glu Cys Leu Arg Gly Ser Thr Lys Ser Cys Ala Arg
            355                 360                 365

Thr Leu Val Ser Gly Ser Phe Gly Asn Arg Phe Ile Leu Ser Gln Gly
370                 375                 380

Asn Leu Ile Ala Asn Cys Ala Ser Ile Leu Cys Lys Cys Tyr Thr Thr
385                 390                 395                 400

Gly Thr Ile Ile Asn Gln Asp Pro Asp Lys Ile Leu Thr Tyr Ile Ala
                405                 410                 415

Ala Asp His Cys Pro Val Val Glu Val Asn Gly Val Thr Ile Gln Val
            420                 425                 430

Gly Ser Arg Arg Tyr Pro Asp Ala Val Tyr Leu His Arg Ile Asp Leu
```

```
        435                 440                 445

Gly Pro Pro Ile Ser Leu Glu Arg Leu Asp Val Gly Thr Asn Leu Gly
    450                 455                 460

Asn Ala Ile Ala Lys Leu Glu Asp Ala Lys Glu Leu Leu Glu Ser Ser
465                 470                 475                 480

Asp Gln Ile Leu Arg Ser Met Lys Gly Leu Ser Ser Thr Ser Ile Val
                485                 490                 495

Tyr Ile Leu Ile Ala Val Cys Leu Gly Gly Leu Ile Gly Ile Pro Ala
            500                 505                 510

Leu Ile Cys Cys Cys Arg Gly Arg Cys Asn Lys Lys Gly Glu Gln Val
        515                 520                 525

Gly Met Ser Arg Pro Gly Leu Lys Pro Asp Leu Thr Gly Thr Ser Lys
    530                 535                 540

Ser Tyr Val Arg Ser Leu
545                 550

<210> SEQ ID NO 6
<211> LENGTH: 617
<212> TYPE: PRT
<213> ORGANISM: Measles virus

<400> SEQUENCE: 6

Met Ser Pro Gln Arg Asp Arg Ile Asn Ala Phe Tyr Lys Asp Asn Pro
1               5                   10                  15

His Pro Lys Gly Ser Arg Ile Val Ile Asn Arg Glu His Leu Met Ile
            20                  25                  30

Asp Arg Pro Tyr Val Leu Leu Ala Val Leu Phe Val Met Phe Leu Ser
        35                  40                  45

Leu Ile Gly Leu Leu Ala Ile Ala Gly Ile Arg Leu His Arg Ala Ala
    50                  55                  60

Ile Tyr Thr Ala Glu Ile His Lys Ser Leu Ser Thr Asn Leu Asp Val
65                  70                  75                  80

Thr Asn Ser Ile Glu His Gln Val Lys Asp Val Leu Thr Pro Leu Phe
                85                  90                  95

Lys Ile Ile Gly Asp Glu Val Gly Leu Arg Thr Pro Gln Arg Phe Thr
            100                 105                 110

Asp Leu Val Lys Phe Ile Ser Asp Lys Ile Lys Phe Leu Asn Pro Asp
        115                 120                 125

Arg Glu Tyr Asp Phe Arg Asp Leu Thr Trp Cys Ile Asn Pro Pro Glu
    130                 135                 140

Arg Ile Lys Leu Asp Tyr Asp Gln Tyr Cys Ala Asp Val Ala Ala Glu
145                 150                 155                 160

Glu Leu Met Asn Ala Leu Val Asn Ser Thr Leu Leu Glu Ala Arg Ala
                165                 170                 175

Thr Asn Gln Phe Leu Ala Val Ser Lys Gly Asn Cys Ser Gly Pro Thr
            180                 185                 190

Thr Ile Arg Gly Gln Phe Ser Asn Met Ser Leu Ser Leu Leu Asp Leu
        195                 200                 205

Tyr Leu Ser Arg Gly Tyr Asn Val Ser Ser Ile Val Thr Met Thr Ser
    210                 215                 220

Gln Gly Met Tyr Gly Gly Thr Tyr Leu Val Glu Lys Pro Asn Leu Ser
225                 230                 235                 240

Ser Lys Gly Ser Glu Leu Ser Gln Leu Ser Met His Arg Val Phe Glu
                245                 250                 255
```

```
Val Gly Val Ile Arg Asn Pro Gly Leu Gly Ala Pro Val Phe His Met
            260                 265                 270

Thr Asn Tyr Phe Glu Gln Pro Val Ser Asn Asp Phe Ser Asn Cys Met
            275                 280                 285

Val Ala Leu Gly Glu Leu Lys Phe Ala Ala Leu Cys His Arg Glu Asp
            290                 295                 300

Ser Ile Thr Ile Pro Tyr Gln Gly Ser Gly Lys Gly Val Ser Phe Gln
305                 310                 315                 320

Leu Val Lys Leu Gly Val Trp Lys Ser Pro Thr Asp Met Arg Ser Trp
                325                 330                 335

Val Pro Leu Ser Thr Asp Asp Pro Val Ile Asp Arg Leu Tyr Leu Ser
            340                 345                 350

Ser His Arg Gly Val Ile Ala Asp Asn Gln Ala Lys Trp Ala Val Pro
            355                 360                 365

Thr Thr Arg Thr Asp Asp Lys Leu Arg Met Glu Thr Cys Phe Gln Gln
            370                 375                 380

Ala Cys Lys Gly Lys Asn Gln Ala Leu Cys Glu Asn Pro Glu Trp Ala
385                 390                 395                 400

Pro Leu Lys Asp Asn Arg Ile Pro Ser Tyr Gly Val Leu Ser Val Asn
                405                 410                 415

Leu Ser Leu Thr Ala Glu Leu Lys Ile Lys Ile Ala Ser Gly Phe Gly
            420                 425                 430

Pro Leu Ile Thr His Gly Ser Gly Met Asp Leu Tyr Lys Thr Asn His
            435                 440                 445

Asn Asn Val Tyr Trp Leu Thr Ile Pro Pro Met Lys Asn Leu Ala Leu
450                 455                 460

Gly Val Ile Asn Thr Leu Glu Trp Ile Pro Arg Phe Lys Val Ser Pro
465                 470                 475                 480

Asn Leu Phe Thr Val Pro Ile Lys Glu Ala Gly Glu Asp Cys His Ala
                485                 490                 495

Pro Thr Tyr Leu Pro Ala Glu Val Asp Gly Asp Val Lys Leu Ser Ser
            500                 505                 510

Asn Leu Val Ile Leu Pro Gly Gln Asp Leu Gln Tyr Val Leu Ala Thr
            515                 520                 525

Tyr Asp Thr Ser Ala Val Glu His Ala Val Val Tyr Tyr Val Tyr Ser
530                 535                 540

Pro Ser Arg Ser Phe Ser Tyr Phe Tyr Pro Phe Arg Leu Pro Ile Lys
545                 550                 555                 560

Gly Val Pro Ile Glu Leu Gln Val Glu Cys Phe Thr Trp Asp Lys Lys
                565                 570                 575

Leu Trp Cys Arg His Phe Cys Val Leu Ala Asp Ser Glu Ser Gly Gly
            580                 585                 590

His Ile Thr His Ser Gly Met Val Gly Met Gly Val Ser Cys Thr Val
            595                 600                 605

Thr Arg Glu Asp Gly Thr Asn Arg Arg
610                 615

<210> SEQ ID NO 7
<211> LENGTH: 2183
<212> TYPE: PRT
<213> ORGANISM: Measles virus

<400> SEQUENCE: 7

Met Asp Ser Leu Ser Val Asn Gln Ile Leu Tyr Pro Glu Val His Leu
1               5                   10                  15
```

-continued

Asp Ser Pro Ile Val Thr Asn Lys Ile Val Ala Ile Leu Glu Tyr Ala
         20                  25                  30

Arg Val Pro His Ala Tyr Ser Leu Glu Asp Pro Thr Leu Cys Gln Asn
         35                  40                  45

Ile Lys His Arg Leu Lys Asn Gly Phe Ser Asn Gln Met Ile Ile Asn
     50                  55                  60

Asn Val Glu Val Gly Asn Val Ile Lys Ser Lys Leu Arg Ser Tyr Pro
65                  70                  75                  80

Ala His Ser His Ile Pro Tyr Pro Asn Cys Asn Gln Asp Leu Phe Asn
                 85                  90                  95

Ile Glu Asp Lys Glu Ser Thr Arg Lys Ile Arg Glu Leu Leu Lys Lys
             100                 105                 110

Gly Asn Ser Leu Tyr Ser Lys Val Ser Asp Lys Val Phe Gln Cys Leu
             115                 120                 125

Arg Asp Thr Asn Ser Arg Leu Gly Leu Gly Ser Glu Leu Arg Glu Asp
     130                 135                 140

Ile Lys Glu Lys Ile Ile Asn Leu Gly Val Tyr Met His Ser Ser Gln
145                 150                 155                 160

Trp Phe Glu Pro Phe Leu Phe Trp Phe Thr Val Lys Thr Glu Met Arg
                 165                 170                 175

Ser Val Ile Lys Ser Gln Thr His Thr Cys His Arg Arg His Thr
             180                 185                 190

Pro Val Phe Phe Thr Gly Ser Ser Val Glu Leu Leu Ile Ser Arg Asp
         195                 200                 205

Leu Val Ala Ile Ile Ser Lys Glu Ser Gln His Val Tyr Tyr Leu Thr
         210                 215                 220

Phe Glu Leu Val Leu Met Tyr Cys Asp Val Ile Glu Gly Arg Leu Met
225                 230                 235                 240

Thr Glu Thr Ala Met Thr Ile Asp Ala Arg Tyr Ala Glu Leu Leu Gly
             245                 250                 255

Arg Val Arg Tyr Met Trp Lys Leu Ile Asp Gly Phe Phe Pro Ala Leu
             260                 265                 270

Gly Asn Pro Thr Tyr Gln Ile Val Ala Met Leu Glu Pro Leu Ser Leu
             275                 280                 285

Ala Tyr Leu Gln Leu Arg Asp Ile Thr Val Glu Leu Arg Gly Ala Phe
         290                 295                 300

Leu Asn His Cys Phe Thr Glu Ile His Asp Val Leu Asp Gln Asn Gly
305                 310                 315                 320

Phe Ser Asp Glu Gly Thr Tyr His Glu Leu Ile Glu Ala Leu Asp Tyr
                 325                 330                 335

Ile Phe Ile Thr Asp Asp Ile His Leu Thr Gly Glu Ile Phe Ser Phe
             340                 345                 350

Phe Arg Ser Phe Gly His Pro Arg Leu Glu Ala Val Thr Ala Ala Glu
         355                 360                 365

Asn Val Arg Lys Tyr Met Asn Gln Pro Lys Val Ile Val Tyr Glu Thr
         370                 375                 380

Leu Met Lys Gly His Ala Ile Phe Cys Gly Ile Ile Asn Gly Tyr
385                 390                 395                 400

Arg Asp Arg His Gly Gly Ser Trp Pro Pro Leu Thr Leu Pro Leu His
                 405                 410                 415

Ala Ala Asp Thr Ile Arg Asn Ala Gln Ala Ser Gly Glu Gly Leu Thr
             420                 425                 430

-continued

```
His Glu Gln Cys Val Asp Asn Trp Lys Ser Phe Ala Gly Val Arg Phe
            435                 440                 445
Gly Cys Phe Met Pro Leu Ser Leu Asp Ser Asp Leu Thr Met Tyr Leu
450                 455                 460
Lys Asp Lys Ala Leu Ala Ala Leu Gln Arg Glu Trp Asp Ser Val Tyr
465                 470                 475                 480
Pro Lys Glu Phe Leu Arg Tyr Asp Pro Lys Gly Thr Gly Ser Arg
                485                 490                 495
Arg Leu Val Asp Val Phe Leu Asn Asp Ser Ser Phe Asp Pro Tyr Asp
            500                 505                 510
Met Ile Met Tyr Val Val Ser Gly Ala Tyr Leu His Asp Pro Glu Phe
            515                 520                 525
Asn Leu Ser Tyr Ser Leu Lys Glu Lys Glu Ile Lys Glu Thr Gly Arg
530                 535                 540
Leu Phe Ala Lys Met Thr Tyr Lys Met Arg Ala Cys Gln Val Ile Ala
545                 550                 555                 560
Glu Asn Leu Ile Ser Asn Gly Ile Gly Lys Tyr Phe Lys Asp Asn Gly
                565                 570                 575
Met Ala Lys Asp Glu His Asp Leu Thr Lys Ala Leu His Thr Leu Ala
            580                 585                 590
Val Ser Gly Val Pro Lys Asp Leu Lys Glu Ser His Arg Gly Gly Pro
            595                 600                 605
Val Leu Lys Thr Tyr Ser Arg Ser Pro Val His Thr Ser Thr Arg Asn
            610                 615                 620
Val Lys Ala Lys Lys Gly Phe Val Gly Phe Pro His Val Ile Arg Gln
625                 630                 635                 640
Asn Gln Asp Thr Asp His Pro Glu Asn Ile Glu Thr Tyr Glu Thr Val
                645                 650                 655
Ser Ala Phe Ile Thr Thr Asp Leu Lys Lys Tyr Cys Leu Asn Trp Arg
            660                 665                 670
Tyr Glu Thr Ile Ser Leu Phe Ala Gln Arg Leu Asn Glu Ile Tyr Gly
            675                 680                 685
Leu Pro Ser Phe Phe Gln Trp Leu His Lys Arg Leu Glu Thr Ser Val
690                 695                 700
Leu Tyr Val Ser Asp Pro His Cys Pro Pro Asp Leu Asp Ala His Val
705                 710                 715                 720
Pro Leu Cys Lys Val Pro Asn Asp Gln Ile Phe Ile Lys Tyr Pro Met
                725                 730                 735
Gly Gly Ile Glu Gly Tyr Cys Gln Lys Leu Trp Thr Ile Ser Thr Ile
            740                 745                 750
Pro Tyr Leu Tyr Leu Ala Ala Tyr Glu Ser Gly Val Arg Ile Ala Ser
            755                 760                 765
Leu Val Gln Gly Asp Asn Gln Thr Ile Ala Val Thr Lys Arg Val Pro
770                 775                 780
Ser Thr Trp Pro Tyr Asn Leu Lys Lys Arg Glu Ala Ala Arg Val Thr
785                 790                 795                 800
Arg Asp Tyr Phe Val Ile Leu Arg Gln Arg Leu His Asp Ile Gly His
                805                 810                 815
His Leu Lys Ala Asn Glu Thr Ile Val Ser Ser His Phe Phe Val Tyr
            820                 825                 830
Ser Lys Gly Ile Tyr Tyr Asp Gly Leu Leu Val Ser Gln Ser Leu Lys
            835                 840                 845
Ser Ile Ala Arg Cys Val Phe Trp Ser Glu Thr Ile Val Asp Glu Thr
```

-continued

```
            850                 855                 860
Arg Ala Ala Cys Ser Asn Ile Ala Thr Thr Met Ala Lys Ser Ile Glu
865                 870                 875                 880
Arg Gly Tyr Asp Arg Tyr Leu Ala Tyr Ser Leu Asn Val Leu Lys Val
                885                 890                 895
Ile Gln Gln Ile Leu Ile Ser Leu Gly Phe Thr Ile Asn Ser Thr Met
                    900                 905                 910
Thr Arg Asp Val Val Ile Pro Leu Leu Thr Asn Asn Asp Leu Leu Ile
                915                 920                 925
Arg Met Ala Leu Leu Pro Ala Pro Ile Gly Gly Met Asn Tyr Leu Asn
            930                 935                 940
Met Ser Arg Leu Phe Val Arg Asn Ile Gly Asp Pro Val Thr Ser Ser
945                 950                 955                 960
Ile Ala Asp Leu Lys Arg Met Ile Leu Ala Ser Leu Met Pro Glu Glu
                965                 970                 975
Thr Leu His Gln Val Met Thr Gln Gln Pro Gly Asp Ser Ser Phe Leu
                980                 985                 990
Asp Trp Ala Ser Asp Pro Tyr Ser  Ala Asn Leu Val Cys  Val Gln Ser
        995                 1000                1005
Ile Thr  Arg Leu Leu Lys Asn  Ile Thr Ala Arg Phe  Val Leu Ile
    1010                1015                1020
His Ser  Pro Asn Pro Met Leu  Lys Gly Leu Phe His  Asp Asp Ser
    1025                1030                1035
Lys Glu  Glu Asp Glu Arg Leu  Ala Ala Phe Leu Met  Asp Arg His
    1040                1045                1050
Ile Ile  Val Pro Arg Ala Ala  His Glu Ile Leu Asp  His Ser Val
    1055                1060                1065
Thr Gly  Ala Arg Glu Ser Ile  Ala Gly Met Leu Asp  Thr Thr Lys
    1070                1075                1080
Gly Leu  Ile Arg Ala Ser Met  Arg Lys Gly Gly Leu  Thr Ser Arg
    1085                1090                1095
Val Ile  Thr Arg Leu Ser Asn  Tyr Asp Tyr Glu Gln  Phe Arg Ala
    1100                1105                1110
Gly Met  Val Leu Leu Thr Gly  Arg Lys Arg Asn Val  Leu Ile Asp
    1115                1120                1125
Lys Glu  Ser Cys Ser Val Gln  Leu Ala Arg Ala Leu  Arg Ser His
    1130                1135                1140
Met Trp  Ala Arg Leu Ala Arg  Gly Arg Pro Ile Tyr  Gly Leu Glu
    1145                1150                1155
Val Pro  Asp Val Leu Glu Ser  Met Arg Gly His Leu  Ile Arg Arg
    1160                1165                1170
His Glu  Thr Cys Val Ile Cys  Glu Cys Gly Ser Val  Asn Tyr Gly
    1175                1180                1185
Trp Phe  Phe Val Pro Ser Gly  Cys Gln Leu Asp Asp  Ile Asp Lys
    1190                1195                1200
Glu Thr  Ser Ser Leu Arg Val  Pro Tyr Ile Gly Ser  Thr Thr Asp
    1205                1210                1215
Glu Arg  Thr Asp Met Lys Leu  Ala Phe Val Arg Ala  Pro Ser Arg
    1220                1225                1230
Ser Leu  Arg Ser Ala Val Arg  Ile Ala Thr Val Tyr  Ser Trp Ala
    1235                1240                1245
Tyr Gly  Asp Asp Asp Ser Ser  Trp Asn Glu Ala Trp  Leu Leu Ala
    1250                1255                1260
```

-continued

Arg Gln Arg Ala Asn Val Ser Leu Glu Glu Leu Arg Val Ile Thr
1265                1270                1275

Pro Ile Ser Thr Ser Thr Asn Leu Ala His Arg Leu Arg Asp Arg
1280                1285                1290

Ser Thr Gln Val Lys Tyr Ser Gly Thr Ser Leu Val Arg Val Ala
1295                1300                1305

Arg Tyr Thr Thr Ile Ser Asn Asp Asn Leu Ser Phe Val Ile Ser
1310                1315                1320

Asp Lys Lys Val Asp Thr Asn Phe Ile Tyr Gln Gln Gly Met Leu
1325                1330                1335

Leu Gly Leu Gly Val Leu Glu Thr Leu Phe Arg Leu Glu Lys Asp
1340                1345                1350

Thr Gly Ser Ser Asn Thr Val Leu His Leu His Val Glu Thr Asp
1355                1360                1365

Cys Cys Val Ile Pro Met Ile Asp His Pro Arg Ile Pro Ser Ser
1370                1375                1380

Arg Lys Leu Glu Leu Arg Ala Glu Leu Cys Thr Asn Pro Leu Ile
1385                1390                1395

Tyr Asp Asn Ala Pro Leu Ile Asp Arg Asp Ala Thr Arg Leu Tyr
1400                1405                1410

Thr Gln Ser His Arg Arg His Leu Val Glu Phe Val Thr Trp Ser
1415                1420                1425

Thr Pro Gln Leu Tyr His Ile Leu Ala Lys Ser Thr Ala Leu Ser
1430                1435                1440

Met Ile Asp Leu Val Thr Lys Phe Glu Lys Asp His Met Asn Glu
1445                1450                1455

Ile Ser Ala Leu Ile Gly Asp Asp Asp Ile Asn Ser Phe Ile Thr
1460                1465                1470

Glu Phe Leu Leu Ile Glu Pro Arg Leu Phe Thr Ile Tyr Leu Gly
1475                1480                1485

Gln Cys Ala Ala Ile Asn Trp Ala Phe Asp Val His Tyr His Arg
1490                1495                1500

Pro Ser Gly Lys Tyr Gln Met Gly Glu Leu Leu Ser Ser Phe Leu
1505                1510                1515

Ser Arg Met Ser Lys Gly Val Phe Lys Val Leu Val Asn Ala Leu
1520                1525                1530

Ser His Pro Lys Ile Tyr Lys Lys Phe Trp His Cys Gly Ile Ile
1535                1540                1545

Glu Pro Ile His Gly Pro Ser Leu Asp Ala Gln Asn Leu His Thr
1550                1555                1560

Thr Val Cys Asn Met Val Tyr Thr Cys Tyr Met Thr Tyr Leu Asp
1565                1570                1575

Leu Leu Leu Asn Glu Glu Leu Glu Glu Phe Thr Phe Leu Leu Cys
1580                1585                1590

Glu Ser Asp Glu Asp Val Val Pro Asp Arg Phe Asp Asn Ile Gln
1595                1600                1605

Ala Lys His Leu Cys Val Leu Ala Asp Leu Tyr Cys Gln Pro Gly
1610                1615                1620

Thr Cys Pro Pro Ile Arg Gly Leu Arg Pro Val Glu Lys Cys Ala
1625                1630                1635

Val Leu Thr Asp His Ile Lys Thr Glu Ala Arg Leu Ser Pro Ala
1640                1645                1650

```
Gly Ser Ser Trp Asn Ile Asn Pro Ile Ile Val Asp His Tyr Ser
    1655                1660                1665

Cys Ser Leu Thr Tyr Leu Arg Arg Gly Ser Ile Lys Gln Ile Arg
    1670                1675                1680

Leu Arg Val Asp Pro Gly Phe Ile Phe Asp Ala Leu Ala Glu Val
    1685                1690                1695

Asn Val Ser Gln Pro Lys Val Gly Ser Asn Asn Ile Ser Asn Met
    1700                1705                1710

Ser Ile Lys Asp Phe Arg Pro Pro His Asp Val Ala Lys Leu
    1715                1720                1725

Leu Lys Asp Ile Asn Thr Ser Lys His Asn Leu Pro Ile Ser Gly
    1730                1735                1740

Gly Ser Leu Ala Asn Tyr Glu Ile His Ala Phe Arg Arg Ile Gly
    1745                1750                1755

Leu Asn Ser Ser Ala Cys Tyr Lys Ala Val Glu Ile Ser Thr Leu
    1760                1765                1770

Ile Arg Arg Cys Leu Glu Pro Gly Glu Asp Gly Leu Phe Leu Gly
    1775                1780                1785

Glu Gly Ser Gly Ser Met Leu Ile Thr Tyr Lys Glu Ile Leu Lys
    1790                1795                1800

Leu Asn Lys Cys Phe Tyr Asn Ser Gly Val Ser Ala Asn Ser Arg
    1805                1810                1815

Ser Gly Gln Arg Glu Leu Ala Pro Tyr Pro Ser Glu Val Gly Leu
    1820                1825                1830

Val Glu His Arg Met Gly Val Gly Asn Ile Val Lys Val Leu Phe
    1835                1840                1845

Asn Gly Arg Pro Glu Val Thr Trp Val Gly Ser Ile Asp Cys Phe
    1850                1855                1860

Asn Phe Ile Val Ser Asn Ile Pro Thr Ser Ser Val Gly Phe Ile
    1865                1870                1875

His Ser Asp Ile Glu Thr Leu Pro Asn Lys Asp Thr Ile Glu Lys
    1880                1885                1890

Leu Glu Glu Leu Ala Ala Ile Leu Ser Met Ala Leu Leu Leu Gly
    1895                1900                1905

Lys Ile Gly Ser Ile Leu Val Ile Lys Leu Met Pro Phe Ser Gly
    1910                1915                1920

Asp Phe Val Gln Gly Phe Ile Ser Tyr Val Gly Ser His Tyr Arg
    1925                1930                1935

Glu Val Asn Leu Val Tyr Pro Arg Tyr Ser Asn Phe Ile Ser Thr
    1940                1945                1950

Glu Ser Tyr Leu Val Leu Thr Asp Leu Lys Ala Asn Arg Leu Met
    1955                1960                1965

Asn Pro Glu Lys Ile Lys Gln Gln Ile Ile Glu Ser Ser Val Arg
    1970                1975                1980

Thr Ser Pro Gly Leu Ile Gly His Ile Leu Ser Ile Lys Gln Leu
    1985                1990                1995

Ser Cys Ile Gln Ala Ile Val Gly Gly Ala Val Ser Arg Gly Asp
    2000                2005                2010

Ile Asn Pro Ile Leu Lys Lys Leu Thr Pro Ile Glu Gln Val Leu
    2015                2020                2025

Ile Ser Cys Gly Leu Ala Ile Asn Gly Pro Lys Leu Cys Lys Glu
    2030                2035                2040

Leu Ile His His Asp Val Ala Ser Gly Gln Asp Gly Leu Leu Asn
```

```
                         2045                2050                2055

Ser Ile Leu Ile Leu Tyr Arg Glu Leu Ala Arg Phe Lys Asp Asn
    2060                2065                2070

Gln Arg Ser Gln Gln Gly Met Phe His Ala Tyr Pro Val Leu Val
    2075                2080                2085

Ser Ser Arg Gln Arg Glu Leu Val Ser Arg Ile Thr Arg Lys Phe
    2090                2095                2100

Trp Gly His Ile Leu Leu Tyr Ser Gly Asn Arg Lys Leu Ile Asn
    2105                2110                2115

Arg Phe Ile Gln Asn Leu Lys Ser Gly Tyr Leu Val Leu Asp Leu
    2120                2125                2130

His Gln Asn Ile Phe Val Lys Asn Leu Ser Lys Ser Glu Lys Gln
    2135                2140                2145

Ile Ile Met Thr Gly Gly Leu Lys Arg Glu Trp Val Phe Lys Val
    2150                2155                2160

Thr Val Lys Glu Thr Lys Glu Trp Tyr Lys Leu Val Gly Tyr Ser
    2165                2170                2175

Ala Leu Ile Lys Asp
    2180

<210> SEQ ID NO 8
<211> LENGTH: 20
<212> TYPE: DNA
<213> ORGANISM: Artificial Sequence
<220> FEATURE:
<223> OTHER INFORMATION: Synthetic primer

<400> SEQUENCE: 8
acatcctcca cgtgtccttc                                                20

<210> SEQ ID NO 9
<211> LENGTH: 20
<212> TYPE: DNA
<213> ORGANISM: Artificial Sequence
<220> FEATURE:
<223> OTHER INFORMATION: Synthetic primer

<400> SEQUENCE: 9
caaagtgtcc ccatccactc                                                20

<210> SEQ ID NO 10
<211> LENGTH: 22
<212> TYPE: DNA
<213> ORGANISM: Artificial Sequence
<220> FEATURE:
<223> OTHER INFORMATION: Synthetic primer

<400> SEQUENCE: 10
cacccactcc tccacctttg ac                                             22

<210> SEQ ID NO 11
<211> LENGTH: 22
<212> TYPE: DNA
<213> ORGANISM: Artificial Sequence
<220> FEATURE:
<223> OTHER INFORMATION: Synthetic primer

<400> SEQUENCE: 11
gtccaccacc ctgttgctgt ag                                             22

<210> SEQ ID NO 12
```

```
<211> LENGTH: 24
<212> TYPE: DNA
<213> ORGANISM: Artificial Sequence
<220> FEATURE:
<223> OTHER INFORMATION: Synthetic primer

<400> SEQUENCE: 12
ggtcagttcc ttattcaagt ctgc                                             24

<210> SEQ ID NO 13
<211> LENGTH: 23
<212> TYPE: DNA
<213> ORGANISM: Artificial Sequence
<220> FEATURE:
<223> OTHER INFORMATION: Synthetic primer

<400> SEQUENCE: 13
gctaaaatct cccatgtcaa cag                                              23
```